(12) United States Patent
Cashman et al.

(10) Patent No.: US 10,223,681 B2
(45) Date of Patent: *Mar. 5, 2019

(54) VETERINARY KIOSK WITH INTEGRATED VETERINARY MEDICAL DEVICES

(71) Applicant: Rite Aid Hdqtrs. Corp., Camp Hill, PA (US)

(72) Inventors: Steve Cashman, Powell, OH (US); John Scott Churran, Westerville, OH (US)

(73) Assignee: Rite Aid Hdqtrs. Corp., Camp Hill, PA (US)

( * ) Notice: Subject to any disclaimer, the term of this patent is extended or adjusted under 35 U.S.C. 154(b) by 156 days.

This patent is subject to a terminal disclaimer.

(21) Appl. No.: 13/967,424

(22) Filed: Aug. 15, 2013

(65) Prior Publication Data

US 2014/0052463 A1 Feb. 20, 2014

Related U.S. Application Data

(60) Provisional application No. 61/683,469, filed on Aug. 15, 2012.

(51) Int. Cl.
*G06Q 20/18* (2012.01)
*G06Q 50/22* (2018.01)
*G06Q 10/10* (2012.01)
*G16H 80/00* (2018.01)
*G16H 40/60* (2018.01)
(Continued)

(52) U.S. Cl.
CPC ......... *G06Q 20/18* (2013.01); *G06F 19/3418* (2013.01); *G06Q 10/1095* (2013.01); *G06Q 50/22* (2013.01); *G16H 40/20* (2018.01); *G16H 40/60* (2018.01); *G16H 80/00* (2018.01)

(58) Field of Classification Search
None
See application file for complete search history.

(56) References Cited

U.S. PATENT DOCUMENTS 3,838,545 A 10/1974 Kump
4,312,359 A 1/1982 Olson
(Continued)

FOREIGN PATENT DOCUMENTS

CN 2706553 Y 6/2005
CN 1884776 A 12/2006
(Continued)

OTHER PUBLICATIONS

Spacelabs Medical Inc. Website, Vita-State Health Screening Product Nos. 90550 and 90555 (May 26, 1998).
(Continued)

*Primary Examiner* — Jonathan Ng
*Assistant Examiner* — William G Lultschik
(74) *Attorney, Agent, or Firm* — Pepper Hamilton LLP

(57) ABSTRACT

A veterinary kiosk designed to provide tele-med services, check-in services, and/or prescription services for a user and an animal. The veterinary kiosk can include a user video conferencing system that is designed to enable the user to have a real-time or near real-time tele-conference with a veterinary provider located remotely from the veterinary kiosk. A method of providing veterinary services via a modular veterinary kiosk with one or more integrated veterinary medical devices.

9 Claims, 7 Drawing Sheets

(51) Int. Cl.
  *G16H 40/20* (2018.01)
  *G06F 19/00* (2018.01)

(56) References Cited

U.S. PATENT DOCUMENTS

| | | | |
|---|---|---|---|
| 4,718,428 A | 1/1988 | Russel | |
| 4,884,514 A | 12/1989 | Shockey et al. | |
| 4,933,873 A * | 6/1990 | Kaufman | G06F 19/3462 |
| | | | 600/300 |
| 5,036,779 A | 8/1991 | Capraro | |
| 5,058,871 A * | 10/1991 | Congin | A61G 13/0018 |
| | | | 5/610 |
| D334,985 S | 4/1993 | D'Agostino et al. | |
| D344,140 S | 2/1994 | Webster | |
| 5,307,263 A | 4/1994 | Brown | |
| 5,346,297 A * | 9/1994 | Colson, Jr. | E05B 47/023 |
| | | | 312/215 |
| 5,393,964 A | 2/1995 | Hamilton et al. | |
| 5,441,047 A | 8/1995 | David et al. | |
| D371,844 S | 7/1996 | Sadritabarizi et al. | |
| 5,544,649 A | 8/1996 | David et al. | |
| 5,558,638 A | 9/1996 | Leonaggeo et al. | |
| 5,619,991 A | 4/1997 | Sloane | |
| 5,660,176 A | 8/1997 | Iliff | |
| 5,704,366 A | 1/1998 | Tacklind et al. | |
| 5,727,353 A | 3/1998 | Getz et al. | |
| 5,801,755 A | 9/1998 | Echerer | |
| 5,810,747 A | 9/1998 | Brudny et al. | |
| 5,857,967 A | 1/1999 | Frid et al. | |
| 5,867,821 A | 2/1999 | Ballantyne | |
| 5,868,669 A | 2/1999 | Iliff | |
| 5,897,493 A | 4/1999 | Brown | |
| 5,910,107 A | 6/1999 | Iliff | |
| 5,960,403 A | 10/1999 | Brown | |
| 5,974,124 A | 10/1999 | Schlueter, Jr. et al. | |
| 5,987,519 A | 11/1999 | Peifer et al. | |
| 5,997,476 A | 12/1999 | Brown | |
| 6,007,459 A | 12/1999 | Burgess | |
| 6,014,432 A | 1/2000 | Modney | |
| 6,022,315 A | 2/2000 | Iliff | |
| 6,038,465 A | 3/2000 | Melton, Jr. | |
| 6,044,382 A | 3/2000 | Martino | |
| 6,046,761 A | 4/2000 | Echerer | |
| 6,071,236 A | 6/2000 | Iliff | |
| 6,101,478 A | 8/2000 | Brown | |
| 6,113,540 A | 9/2000 | Iliff | |
| 6,190,313 B1 | 2/2001 | Hinkle | |
| 6,205,716 B1 | 3/2001 | Peltz | |
| 6,206,829 B1 | 3/2001 | Iliff | |
| 6,224,548 B1 | 5/2001 | Gopinathan et al. | |
| 6,248,064 B1 | 6/2001 | Gopinathan et al. | |
| 6,248,065 B1 | 6/2001 | Brown | |
| 6,270,455 B1 | 8/2001 | Brown | |
| 6,295,767 B1 | 10/2001 | Barnhill et al. | |
| 6,302,844 B1 | 10/2001 | Walker et al. | |
| 6,336,136 B1 | 1/2002 | Harris | |
| 6,368,273 B1 | 4/2002 | Brown | |
| 6,369,847 B1 | 4/2002 | James et al. | |
| 6,381,577 B1 | 4/2002 | Brown | |
| 6,403,897 B1 | 6/2002 | Bluth et al. | |
| 6,428,124 B1 | 8/2002 | Bluth et al. | |
| 6,449,001 B1 | 9/2002 | Levy et al. | |
| 6,511,435 B1 | 1/2003 | Bluth et al. | |
| 6,540,673 B2 | 4/2003 | Gopinathan et al. | |
| 6,594,607 B2 | 7/2003 | Lavery | |
| 6,595,918 B2 | 7/2003 | Gopinathan et al. | |
| 6,602,469 B1 | 8/2003 | Maus et al. | |
| 6,638,218 B2 | 10/2003 | Bulat | |
| 6,641,532 B2 | 11/2003 | Iliff | |
| 6,668,375 B1 | 12/2003 | Brown | |
| 6,692,436 B1 | 2/2004 | Bluth et al. | |
| 6,725,209 B1 | 4/2004 | Iliff | |
| 6,731,324 B2 | 5/2004 | Levy | |
| 6,748,353 B1 | 6/2004 | Iliff | |
| 6,790,178 B1 | 9/2004 | Mault et al. | |
| 6,850,889 B1 | 2/2005 | Zayas, Jr. | |
| 6,968,375 B1 | 11/2005 | Brown | |
| 7,011,629 B2 | 3/2006 | Bulat | |
| D521,155 S | 5/2006 | Shipard | |
| D526,065 S | 8/2006 | Shipard | |
| 7,112,175 B2 | 9/2006 | Gopinathan et al. | |
| 7,188,151 B2 | 3/2007 | Kumar et al. | |
| 7,223,236 B2 | 5/2007 | Brown | |
| 7,252,636 B2 | 8/2007 | Brown | |
| 7,287,031 B1 | 10/2007 | Karpf et al. | |
| 7,297,109 B2 | 11/2007 | Brown | |
| 7,297,111 B2 | 11/2007 | Iliff | |
| 7,300,402 B2 | 11/2007 | Iliff | |
| 7,310,668 B2 | 12/2007 | Brown | |
| 7,320,030 B2 | 1/2008 | Brown | |
| D577,127 S | 9/2008 | Ronco | |
| 7,435,222 B2 | 10/2008 | Gopinathan et al. | |
| 7,516,192 B2 | 4/2009 | Brown | |
| 7,533,171 B2 | 5/2009 | Brown | |
| 7,587,469 B2 | 9/2009 | Brown | |
| 7,613,620 B2 | 11/2009 | Salwan | |
| 7,624,028 B1 | 11/2009 | Brown | |
| 7,673,952 B2 | 3/2010 | Jeansonne et al. | |
| 7,691,059 B2 | 4/2010 | Bulat | |
| 7,707,270 B2 | 4/2010 | Brown | |
| 7,730,177 B2 | 6/2010 | Brown | |
| 7,734,718 B2 | 6/2010 | Brown | |
| 7,753,845 B2 | 7/2010 | Gopinathan et al. | |
| 7,761,312 B2 | 7/2010 | Brown | |
| 7,818,183 B2 | 10/2010 | Schoenberg | |
| 7,822,625 B2 | 10/2010 | Brown | |
| 7,831,444 B2 | 11/2010 | Brown | |
| 7,860,725 B2 | 12/2010 | Gopinathan et al. | |
| 7,870,249 B2 | 1/2011 | Brown | |
| 7,877,271 B2 | 1/2011 | Brown | |
| 7,904,310 B2 | 3/2011 | Brown | |
| 7,912,733 B2 | 3/2011 | Clements et al. | |
| RE42,288 E | 4/2011 | Degioanni | |
| 7,921,186 B2 | 4/2011 | Brown | |
| D638,551 S | 5/2011 | Gann | |
| 7,941,323 B2 | 5/2011 | Brown | |
| 7,941,326 B2 | 5/2011 | Brown | |
| 7,941,327 B2 | 5/2011 | Brown | |
| 7,949,383 B2 | 5/2011 | Cable et al. | |
| 7,970,620 B2 | 6/2011 | Brown | |
| 7,970,633 B2 | 6/2011 | Bulat | |
| 7,979,284 B2 | 7/2011 | Brown | |
| 7,987,100 B2 | 7/2011 | Brown | |
| 8,005,691 B2 | 8/2011 | Kumar et al. | |
| 8,015,025 B2 | 9/2011 | Brown | |
| 8,015,138 B2 | 9/2011 | Iliff | |
| 8,027,809 B2 | 9/2011 | Brown | |
| 8,078,407 B1 | 12/2011 | Brown | |
| 8,078,431 B2 | 12/2011 | Brown | |
| 8,095,340 B2 | 1/2012 | Brown | |
| 8,096,083 B2 | 1/2012 | Ma et al. | |
| 8,140,663 B2 | 3/2012 | Brown | |
| D664,667 S | 7/2012 | Krymov et al. | |
| 8,260,630 B2 | 9/2012 | Brown | |
| 8,285,560 B2 | 10/2012 | Gopinathan et al. | |
| 8,321,284 B2 | 11/2012 | Clements et al. | |
| 8,337,409 B2 | 12/2012 | Iliff | |
| 2001/0011224 A1 | 8/2001 | Brown | |
| 2003/0028399 A1 | 2/2003 | Davis et al. | |
| 2003/0069753 A1 | 4/2003 | Brown | |
| 2003/0088441 A1 | 5/2003 | McNerney | |
| 2003/0163351 A1 | 8/2003 | Brown et al. | |
| 2003/0179290 A1 * | 9/2003 | Frazzitta | G07F 19/20 |
| | | | 348/61 |
| 2004/0006496 A1 | 1/2004 | Nickerson | |
| 2004/0019259 A1 | 1/2004 | Brown | |
| 2004/0019261 A1 | 1/2004 | Gopinathan et al. | |
| 2004/0019505 A1 | 1/2004 | Berenguer | |
| 2004/0107116 A1 | 6/2004 | Brown | |
| 2004/0230458 A1 | 11/2004 | Takayama et al. | |
| 2004/0249778 A1 | 12/2004 | Iliff | |
| 2005/0071916 A1 | 4/2005 | Rooke et al. | |
| 2005/0075907 A1 | 4/2005 | Rao | |
| 2005/0211768 A1 | 9/2005 | Stillman | |

(56) References Cited

U.S. PATENT DOCUMENTS

| | | |
|---|---|---|
| 2005/0228883 A1 | 10/2005 | Brown |
| 2005/0256739 A1 | 11/2005 | Brown |
| 2006/0010014 A1 | 1/2006 | Brown |
| 2006/0200319 A1 | 2/2006 | Brown |
| 2006/0069753 A1 | 3/2006 | Brown |
| 2006/0080152 A1 | 4/2006 | Brown |
| 2006/0083066 A1 | 4/2006 | Hasegawa et al. |
| 2006/0189853 A1 | 8/2006 | Brown |
| 2006/0217056 A1 | 9/2006 | Gomi et al. |
| 2006/0235722 A1 | 10/2006 | Brown |
| 2006/0241975 A1 | 10/2006 | Brown |
| 2006/0259201 A1 | 11/2006 | Brown |
| 2006/0259332 A1 | 11/2006 | Brown |
| 2006/0271214 A1 | 11/2006 | Brown |
| 2006/0285660 A1 | 12/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0293572 A1 | 12/2006 | Bulat |
| 2007/0011320 A1 | 1/2007 | Brown |
| 2007/0016445 A1 | 1/2007 | Brown |
| 2007/0021984 A1 | 1/2007 | Brown |
| 2007/0061167 A1 | 3/2007 | Brown |
| 2007/0073113 A1 | 3/2007 | Squilla et al. |
| 2007/0118588 A1 | 5/2007 | Brown |
| 2007/0130287 A1 | 6/2007 | Kumar et al. |
| 2007/0156893 A1 | 7/2007 | Brown |
| 2007/0168242 A1 | 7/2007 | Brown |
| 2007/0168504 A1 | 7/2007 | Brown |
| 2007/0213605 A1 | 9/2007 | Brown |
| 2007/0265869 A1 | 11/2007 | Ryckman et al. |
| 2007/0299321 A1 | 12/2007 | Brown |
| 2008/0051638 A1 | 2/2008 | Iliff |
| 2008/0051640 A1 | 2/2008 | Iliff |
| 2008/0052119 A1 | 2/2008 | Iliff |
| 2008/0052318 A1 | 2/2008 | Iliff |
| 2008/0059247 A1 | 3/2008 | Iliff |
| 2008/0162393 A1 | 7/2008 | Iliff |
| 2008/0213128 A1 | 9/2008 | Rudy et al. |
| 2009/0012942 A1 | 1/2009 | Thorneycroft et al. |
| 2009/0083066 A1 | 3/2009 | Bailey et al. |
| 2009/0143652 A1 | 6/2009 | Warburton et al. |
| 2009/0167388 A1 | 7/2009 | Poisner et al. |
| 2009/0167838 A1 | 7/2009 | Poisner et al. |
| 2009/0240115 A1 | 9/2009 | Bluth |
| 2009/0240116 A1 | 9/2009 | Bluth |
| 2009/0240524 A1 | 9/2009 | Bluth |
| 2009/0240527 A1 | 9/2009 | Bluth |
| 2009/0240528 A1 | 9/2009 | Bluth |
| 2009/0240702 A1 | 9/2009 | Bluth |
| 2009/0241177 A1 | 9/2009 | Bluth |
| 2010/0030580 A1 | 2/2010 | Salwan |
| 2010/0146300 A1 | 6/2010 | Brown |
| 2010/0274835 A1 | 10/2010 | Brown |
| 2010/0332250 A1 | 12/2010 | Simpson et al. |
| 2011/0004487 A1 | 1/2011 | Schoenberg |
| 2011/0009707 A1 | 1/2011 | Kaundinya et al. |
| 2011/0106557 A1 | 5/2011 | Gazula |
| 2011/0122995 A1 | 5/2011 | Ferro, Jr. |
| 2011/0161475 A1 | 6/2011 | Raghavendran et al. |
| 2011/0191117 A1 | 8/2011 | Hashim-Waris |
| 2011/0288888 A1 | 11/2011 | Gazula |
| 2011/0295417 A1* | 12/2011 | Smith, III ............... G07F 9/006 700/235 |
| 2012/0004525 A1 | 1/2012 | Brown |
| 2012/0130647 A1 | 5/2012 | Brown |
| 2012/0130739 A1 | 5/2012 | Crane |
| 2012/0179479 A1 | 7/2012 | Waterson et al. |
| 2012/0185278 A1 | 7/2012 | Brown |
| 2012/0203466 A1 | 8/2012 | Brown |
| 2012/0253837 A1 | 10/2012 | Cashman |
| 2013/0013333 A1 | 1/2013 | Gopinathan et al. |

FOREIGN PATENT DOCUMENTS

| | | |
|---|---|---|
| CN | 101065056 A | 10/2007 |
| DE | 10129835 | 2/2003 |
| EP | 0219395 | 4/1987 |
| EP | 0342859 | 11/1989 |
| EP | 0423553 | 10/1990 |
| EP | 0959607 | 11/1999 |
| GB | 2477173 | 12/2011 |
| JP | 09-173302 | 8/1997 |
| WO | 96/08910 | 3/1996 |
| WO | 98/20439 | 5/1998 |
| WO | 98/20793 | 5/1998 |
| WO | 98/40835 | 9/1998 |
| WO | 99/30264 | 6/1999 |
| WO | WO 2005029387 A1 * | 3/2005 |
| WO | 2011026146 A2 | 3/2011 |
| WO | WO 2011/161320 | 12/2011 |

OTHER PUBLICATIONS

Kurunganti, Usha, "The Effects of the Information Highway on Health Care in New Brunswick" Proceedings of the IEEE 21st Annual North East Bioengineering Conference; pp. 132-133 (May 22-25, 1995).

Jones, Mary Gardiner, "Telemedicine and the National Information Structure: Are the Realities of Health Care Being Ignored?" J Am Med Inform Assoc; 4:399-412 (1997).

Cardioanalysis Systems, "Owners Manual/Assembly Instructions" (Apr. 1992).

Glass et al., "Nurse and Automatic Machine-Measured Blood Pressure Readings: A comparative Study" Public Health Reports, 95:382-385.

Holfelder et al., "A Networked Multimedia Retrival Management System for Distributed Kiosk Application" IEEE, pp. 342-351 (May 1994).

Warner et al., "Distributed Medical Intelligence" Healthcare in the Information Age, pp. 80-83 (1996).

Warner et al., "Webification of Medication: Interventional Informations Through the WWW" www.pulsar.org/archive/febweb/papers/mww3.htmPage (Oct. 2007).

U.S. Searching Authority, International Search Report and Written Opinion for corresponding application No. PCT/US2013/055040.

Chinese Office Action dated Sep. 14, 2016 in corresponding Chinese Patent Application No. 201510300366.5.

Chinese Office Action dated Oct. 11, 2016 in corresponding Chinese Patent Application No. 201380018091.5.

\* cited by examiner

VETERINARY KIOSK WITH INTEGRATED VETERINARY MEDICAL DEVICES

The present invention claims priority on U.S. Patent Application Ser. No. 61/683,469 filed Aug. 15, 2012, which is incorporated herein by reference.

The present invention is directed to veterinary services, more particularly to a method and device for providing veterinary services to animals, and even more particularly to a method and device for providing veterinary services to animals at locations that traditionally have not provided veterinary services.

The present invention is in the technical field of telemedicine. More particularly, the present invention is in the technical field of a partially- or fully-enclosed modular telemedicine kiosk for providing veterinary services to animals.

BACKGROUND OF THE INVENTION

Veterinary services are traditionally provided to animals at a veterinarian's office or other veterinary facility. Typically, an animal's owner contacts his/her veterinary provider when the animal requires some type of veterinary assistance. The veterinary provider then sets an appointment time and date for the animal to see the veterinary provider. Many times, the time and date of the appointment is inconvenient for the animal's owner. Furthermore, the user or user seeking veterinary assistance desires or needs immediate veterinary assistance, thus cannot wait for the time and date set by the veterinary provider. In such situations, the animal goes to the emergency room of an animal hospital.

The costs associated with visiting a veterinary provider can be costly depending on the type of insurance, if any, the user carries. When an animal visits the emergency room of an animal hospital, the veterinary costs can be substantially higher and insurance coverage may be limited to various types of visits. Insurance coverage and cost of the visit may also vary depending on the animal hospital or clinic.

In many communities, clients are not readily available, thus limiting the number of veterinary providers. The animal must either visit a distant veterinary provider or go to a distant animal hospital.

In view of the current state of veterinary services, there is a need for providing veterinary services in a more convenient, timely and cost-effective manner.

SUMMARY OF THE INVENTION

The present invention is directed to a method and apparatus for providing veterinary services, diagnoses, health, and/or wellness advice to animals (e.g., cats, dogs, birds, etc.) in a convenient, desirable, timely and cost effective manner. The novel medical apparatus of the present invention and the novel method for providing veterinary services, diagnoses, health advice, and/or wellness advice addresses the current deficiencies that exist for providing veterinary services to animals.

In one non-limiting aspect of the invention, there is provided a method and apparatus for providing veterinary services, diagnoses, health, and/or wellness advice to individuals that includes a remote medical service arrangement wherein the user (e.g., pet owner, etc.) can receive various types of medical advice and services remotely from one or more veterinary providers (e.g., veterinarian, veterinarian assistant, animal psychologist, animal psychiatrist, animal specialist, etc.). Traditionally, the animal and the user was required to go to an animal medical facility (e.g., animal hospital, animal clinic, veterinarian's office, etc.) to personally meet with and be diagnosed by the veterinary provider. The present invention is directed to a method wherein veterinary services, diagnoses, health advice, and/or wellness advice can be dispensed by a veterinary provider at a location that is remote from the animal and the user. The present invention can be used to provide any type of veterinary service. The method and device of the present invention can be used to provide initial screening, treatment, and/or follow-up treatment for an animal. The method and device of the present invention can be used in many situations as an alternative for an animal having to visit an animal medical facility. However, it can be appreciated that the device of the present invention could be located in a lobby or special region of an animal medical facility. In one non-limiting arrangement of the present invention, there is provided an audio and/or video link between one or more veterinary providers located at one or more locations (e.g., animal hospital, animal clinic, veterinarian's office, veterinarian's home, etc.) and the animal and the user are located at some other location (e.g., shopping mall, shopping center, drug store, grocery store, department store, warehouse store, discount retailer, discount department store, truck trailer, mobile office, mobile home, office space location, etc.) that is remote from the one or more veterinary providers. The novel method of the present invention for providing veterinary services, diagnoses, health advice, and/or wellness advice enables a veterinary provider to provide veterinary services, diagnoses, health advice, and/or wellness advice to the animal and/or user without the animal and user having to physically visit the veterinary provider and/or having to go to the veterinary provider's office or place of work. As can be appreciated, the audio and/or video link that is used by the veterinary providers can enable the veterinary providers to provide veterinary services, diagnoses, health advice, and/or wellness advice at a single remote location or a plurality of remote locations. When the audio and/or video link enables the veterinary provider to provide veterinary services, diagnoses, health advice, and/or wellness advice to a plurality of remote locations, a single veterinary provider and/or a plurality of veterinary providers can be used to provide veterinary services, diagnoses, health advice, and/or wellness advice to users that are located at a variety of different remote locations. When a plurality of veterinary providers is used, the veterinary providers can be located at the same or different locations. As can be appreciated, the novel method for providing veterinary services allows for more flexibility for a user to obtain veterinary services, diagnoses, health advice, and/or wellness advice. The site at which the user obtains the veterinary services, diagnoses, health advice, and/or wellness advice via the method and device of the present invention can be located in a) non-traditional locations that are more convenient to the user (e.g., pet store, shopping mall, public park, department store, retail store, grocery store, museum, office building, business office, business facility, big box stores, government base or facility, drug stores, boat, airplane, train, etc.), and/or b) traditional locations (e.g., animal hospital, animal clinic, veterinarian's office, etc.) so as to provide easier and/or more convenient access to such veterinary services, diagnoses, health advice, and/or wellness advice. The geographic location for the device of the present invention can be in a single neighborhood, multiple neighborhoods, a single town or city, multiple towns or cities, a single state or province, multiple states or provinces, a single country, or multiple countries. The novel method can also be used to provide veterinary services, diagnoses, health advice, and/or wellness advice at standard times (e.g., 9 am-5 pm Monday through Friday, etc.) and/or non-standard times (e.g., early morning hours, evening hours, weekend hours, holiday hours, etc.) to enable a user to obtain veterinary services, diagnoses, health advice, and/or wellness advice that are more convenient and timely to the user.

In another and/or alternative non-limiting aspect of the invention, there is provided a remote veterinary service arrangement wherein a user can receive various types of medical advice and services remotely from one or more veterinary providers. In one non-limiting arrangement there is provided an audio and/or video link between one or more veterinary providers located at one or more locations and the animal and/or user is located at some other location that is remote from the one or more veterinary providers. The audio/video link can be facilitated by the design of the veterinary kiosk such as, but not limited to, high definition video and/or high quality sound; however, this is not required.

In still another and/or alternative non-limiting aspect of the invention, the novel method of the present invention can be used to provide a variety of different veterinary services, diagnoses, health advice, and/or wellness advice. One or more of the veterinary devices aiding in the providing of services to animals can be integrated with the kiosk. However, as can be appreciated, one non-limiting aspect of the invention is that one or more of the veterinary medical devices may not be fully integrated into the kiosk. In another non-limiting aspect of the invention, one or more of the devices may be located in software-controlled medical device cabinets; however, this is not required. The devices use to aid in the provision of veterinary services may or may not be digital; and may include, but are not limited to, one or more devices selected from the group of an otoscope, a dermascope, a stethoscope, a thermometer, a blood pressure monitor, and/or electronic lift table with or without an integrated scale; however, additional devices or no devices can be included in the kiosk. As can be appreciated, the size and design of the lift table, when used, are non-limiting. As can be appreciated, other or additional devices may be added or subtracted based upon the veterinary healthcare services offered through the kiosk. The size, shape, configuration, and look of the veterinary kiosk are non-limiting. In one non-limiting embodiment of the invention, the veterinary kiosk provides a private or semi-private environment for a user to communicate with a veterinary healthcare provider that is located remotely from the kiosk. The kiosk can include a monitor screen allowing the user to interact with the remote veterinary healthcare provider; however, this is not required. Alternatively or additionally, the kiosk may contain a touch screen and/or data input terminal to aid in the interaction with the remote veterinary healthcare provider which may be attached to one of the walls on the interior of the kiosk; however this is not required. One non-limiting configuration of a kiosk that can be used is disclosed in United States Patent Publication US-2013-0173287, which is fully incorporated herein by reference.

In yet another and/or alternative non-limiting aspect of the invention, the novel method and apparatus for providing veterinary services, diagnoses, health, and/or wellness advice to individuals can be used to provide a variety of different veterinary services, diagnoses, health advice, and/or wellness advice. The veterinary services and/or healthcare services that can be provided can include, but are not limited to, 1) providing advice and/or recommendations about a medical condition, 2) diagnosing and/or treating a medical condition, 3) providing referral services for a medical condition, 4) prescribing medicine for a medical condition, 5) periodically monitoring a medical condition, 6) providing follow-up checks for a medical condition, 7) providing routine check-up services, 8) providing advice, counseling, and/or recommendations about medical and/or health matters, 9) providing a course of treatment for a medical condition, 8) providing health counseling, 10) providing health information, 12) providing wellness counseling, and/or 13) providing wellness information. As can be appreciated, other or additional services can be provided to the user. In essence, any type of medical condition, medical concern, health concern, wellness concern, etc. can be addressed in whole or part by the novel method and apparatus for providing veterinary services of the present invention. Hereinafter, these services will be collectively referred to as 'veterinary services'.

As can be appreciated, the type of services provided to a user will depend on the specific medical condition, medical concern or need, wellness concern or need, and/or health concern or need of the animal and/or user. In many instances, the veterinary provider will be able to diagnose, address, advise, consult and/or treat the specific medical condition or need, medical concern or need, wellness concern or need, health concern or need, etc. of the animal and/or user. In some instances, the specific medical condition or need, medical concern or need, wellness concern or need, health concern or need, etc. of the animal and/or user may be too complicated and/or complex to address via an audio and/or video link, thus the veterinary provider in such situations may have to refer the user to an animal hospital, an animal clinic, a veterinarian's office, etc. for further counseling, treatment and/or diagnosis, or some other location or professional that can address the animal and/or user's needs and/or requirements.

In still another and/or alternative non-limiting aspect of the invention, the novel method and apparatus for providing veterinary services, diagnoses, health, and/or wellness advice to individuals can include the use of a veterinary kiosk to enable the user to conveniently communicate with one or more veterinary providers. One or more veterinary kiosks can be used in the present invention. Generally, a plurality of veterinary kiosks which are located at one or more locations are used in the method of the present invention; however, it can be appreciated that a single veterinary kiosk can be used in accordance with the present invention. Typically, one or more veterinary providers provide services to one or more veterinary kiosks. The size, shape, configuration and look of the veterinary kiosk are non-limiting. In one non-limiting embodiment of the invention, the veterinary kiosk provides a private or semi-private environment for the animal and/or user to communicate with one or more veterinary providers that are located remotely from the veterinary kiosk. In one non-limiting arrangement, the veterinary kiosk includes an enclosure that is designed to enable the animal and/or user to enter the enclosure and the user to communicate with the veterinary provider in a private or semi-private manner while in the enclosure of the veterinary kiosk. The size, shape and configuration of the enclosure of the veterinary kiosk are non-limiting. In another and/or alternative non-limiting arrangement, the veterinary kiosk includes one or more walls that form all or a portion of the sides of the enclosure of the veterinary kiosk. The enclosure may include one or more doors or entry points to enable an animal and the user to enter and/or exit the enclosure. In another and/or alternative non-limiting arrangement, the veterinary kiosk typically includes a floor and/or a ceiling. The ceiling, when included, can include a portion that is partially or fully transparent; however, this is not required. In another and/or alternative non-limiting arrangement, the veterinary kiosk can have a modular configuration to enable the parts of the veterinary kiosk to be set up in various configurations to enable the veterinary kiosk to be used in various types of spaces and/or to be set up in various types of configurations; however, this is not required. The veterinary kiosk can be formed of any number of materials (e.g., plastic, foam, metal, wood, composite materials, fiber board, etc.). The one or more walls of the veterinary kiosk can be designed to be interchangeable to enable the door, when used, to be positioned on various locations on the veterinary kiosk; however, this is not required. The veterinary kiosk can include a floor and/or ceiling to provide for increased privacy for the animal and/or user when the animal and/or user is inside the room, cavity or enclosure of the veterinary kiosk; however, this is not required. The veterinary kiosk can include one or more tables, ledges, benches, and/or seats in the interior and/or exterior of the veterinary kiosk; however, this is not required. Such table, ledge, bench, and/or seat, when used, can be designed to be connected in multiple locations on the exterior and/or interior of the veterinary kiosk; however, this is not required. The modular configuration of the veterinary kiosk can be such that it can be easily assembled and/or disassembled so that the veterinary kiosk can be easily brought into a location and easily set up, and/or be easily removed from a location; however, this is not required.

In yet another and/or alternative non-limiting aspect of the invention, the novel method and apparatus for providing veterinary services, diagnoses, health, and/or wellness advice to an animal and/or user can include the use of a veterinary kiosk that includes one or more data input terminals. The one or more data input terminals can be located on one or more locations on the exterior of the veterinary kiosk; however, this is not required. Alternatively or additionally, the one or more data input terminals can be located on one or more locations in the interior or enclosure of the veterinary kiosk; however, this is not required. The one or more data input terminals can include a video display to display information regarding identification and/or data entry, a camera and/or video camera used to collect information for identification and/or data entry, a key pad or key board for identification and/or data entry, a touch screen for identification and/or data entry, microphone and voice recognition software for identification and/or data entry, fingerprint scanner for identification and/or data entry, retina scanner for identification and/or data entry, and/or face and/or body scanners for identification and/or data entry. As can be appreciated, other or additional devices can be included on the veterinary kiosk to display and/or obtain information regarding identification and/or data entry. The veterinary kiosk can be used by the user to enter/convey basic information about the animal and/or user. Such information includes, but is not limited to, a) user's name, b) user's address, c) user's responsible party contact information (e.g., home address, work address, phone number, email address, pager number, work number, etc.), d) user's age, e) user's sex, f) animal's name, g) type of animal, h) breed of animal, i) age of animal, j) sex of animal, k) medical history of animal, l) animal's weight, m) current medicines used by animal, n) reason(s) for visit by user, o) animal's current symptoms, p) user insurance information, q) user payment information, r) user's current veterinarian, s) desired veterinary provider for visit, t) animal's allergy information, u) information about a prior visit, v) medical records information, and/or w) pharmacy information. As can be appreciated, other or additional information can be input/conveyed by the user.

In still another and/or alternative non-limiting aspect of the invention, the novel method and apparatus for providing veterinary services, diagnoses, health, and/or wellness advice to individuals can include a medial kiosk that can be designed to provide information to the user prior to and/or during the inputting/conveying of information by the user to the veterinary kiosk. In one non-limiting embodiment of the invention, the veterinary kiosk can include audio and/or visual instructions and/or displays used to provide a) information about the veterinary kiosk, b) how to use the veterinary kiosk, c) how to properly input/convey information to the veterinary kiosk, d) provide instructions to and/or interact with the user during the inputting/conveying of information by the user to the veterinary kiosk, e) the wait time for the user's use of the veterinary kiosk, f) a list of users waiting to use the veterinary kiosk, g) available veterinary providers, h) types of medical issues that can be addressed by use of the veterinary kiosk, i) insurance providers that can be used to partially or fully pay for a visit in the veterinary kiosk, j) payment options for use of the veterinary kiosk, k) information regarding when the veterinary kiosk is available in the future, and/or l) information regarding whether the veterinary kiosk is in use or is available. In another and/or alternative non-limiting embodiment of the invention, the veterinary kiosk can include light indicators, sound indicators, and/or digital displays to provide information regarding whether the veterinary kiosk is in use or is available; however, this is not required. In still another and/or alternative non-limiting embodiment of the invention, the veterinary kiosk can include a notification system to a user that the veterinary kiosk is available or will soon be available; however, this is not required. Such notification can be sent via email, text, phone, pager, internet, digital display, etc. Such notification system can be useful when the veterinary kiosk is not currently available to the user. The user can input the information into the veterinary kiosk and then go home, run other errands, etc., and then be later notified when the veterinary kiosk is available or will soon be available. The veterinary kiosk and/or notification system can also be used to inform the user when and/or where other veterinary kiosks are available; however, this is not required. This service, when available, can be used to inform the user that a nearby veterinary kiosk has a shorter wait period or is currently available, thus providing the user with the option of traveling to another available veterinary kiosk instead of waiting for the current veterinary kiosk to become available; however, this is not required. This service, when available, can also be used to inform the user when a prescription is ready for pickup and/or for conveying prescription information to the user; however, this is not required. This service, when available, can also be used to inform the user when a follow-up visit is due and/or scheduled; however, this is not required. As can be appreciated, the notification system can be used for other or additional services.

In yet another and/or alternative non-limiting aspect of the invention, the novel method and apparatus for providing veterinary services, diagnoses, health, and/or wellness advice to animals and/or the user can include a scheduling system for use of the veterinary kiosk. The schedule system allows a user to schedule an appointment with a veterinary provider when the user uses the veterinary kiosk. The scheduling system can be used to 1) enable a user to select a particular veterinary provider, 2) make an appointment on a veterinary kiosk at a particular time and place, 3) enable a user to select a veterinary provider or type of veterinary provider based on the particular need of the user (e.g., select a veterinary provider that specializes in potty training, select a veterinary provider that specializes in discipline issues, select a veterinary provider that specializes in orthopedic issues of animals, etc.), 4) locate available locations of veterinary kiosks, 5) enable a user to enter basic information about the animal and/or user, 6) check a past, current or future appointment of the animal and/or user regarding use of the veterinary kiosk, 7) enter a partial or full payment for use of the veterinary kiosk, and 8) enter medical insurance information, etc. The scheduling system can be designed to be accessed by a user on a data entry device on a veterinary kiosk, via a computer or smart device (e.g., smart phone, tablet, IPad™, etc.), and/or by phone. The scheduling system can optionally be designed to enable a user to request assistance if there a question regarding the use of the scheduling system.

In still yet another and/or alternative non-limiting aspect of the invention, the novel method and apparatus for providing veterinary services, diagnoses, health, and/or wellness advice to animals and/or the user can include one of more software applications (e.g., user registration application, attendant application, user appointment application, veterinary provider application, administrator application, user portal, veterinary provider portal, etc.). For example, the User Appointment or Registration Application can include the screens the user navigates through during the user registration process; however, this is not required. These screens can optionally appear on the registration station of the exterior of the veterinary kiosk. The Attendant Application can include screens that the veterinary attendant, when used, navigates through during the user appointment; however, this is not required. These screens can optionally appear on a laptop, computer screen, tablet, smart phone, etc. located with the veterinary attendant and/or at or near the attendant desk on the exterior of the veterinary kiosk; however, this is not required. The User Appointment or Registration Application can include screens through which the user navigates during the user consultation; however, this is not required. These screens can optionally appear on the veterinary provider screen and/or user screen in the interior of the veterinary kiosk. The Veterinary Provider Application can include the screens the veterinary provider navigates through during the user appointment; however, this is not required. These screens can optionally appear on the veterinary provider's computer, laptop, tablet, smart phone, etc. at his/her remote location. As can be appreciated, other or additional software and/or hardware applications can be used with the veterinary kiosk of the present invention. The User Appointment or Registration Application can allow the user to select a language to be displayed (e.g., English, Spanish, German, French, Chinese, Japanese, etc.); however, this is not required.

In another and/or alternative non-limiting aspect of the invention, the novel method and apparatus for providing veterinary services, diagnoses, health, and/or wellness advice to individuals can include the use of a user Appointment or Registration Application. The User Appointment or Registration Application can include one or more navigational buttons (e.g., back, next, cancel, request assistance, etc.) for use by the user during the registration process; however, this is not required. For example, the Back button can be designed to allow the user to return to the previous screen, the Next button can be designed to allow the user to proceed to the next screen, the Cancel button can be designed to allow the user to cancel a process and return to the beginning of the process (e.g., user receives a pop-up box asking them if they are sure they want to cancel and return to the beginning of the process. They may choose "Yes" or "No". "Yes" returns them to the beginning of the process. "No" returns them to the screen they were on when they hit the "Cancel" button), and the Request Assistance button can be designed to allow the user to request assistance from the Attendant (e.g., the user can receive a pop-up box notifying them that the attendant will be with them in a moment and the attendant also receive a notice that the user requires assistance. The notice provided to the attendant can optionally be color coded and/or generate a certain sound to indicate the source and/or seriousness of the request by a user and/or veterinary provider, etc.). The User Appointment or Registration Application can include a process through which the user identifies themselves as a new and/or returning user and either schedules an appointment at one or more veterinary kiosks or registers for an existing appointment at one or more veterinary kiosks. The veterinary kiosk can optionally be staffed by a medical assistant or attendant at all times. During the user registration process, the medical assistant or attendant responsibilities, when used, can include welcoming the user, offering assistance, validating animal and/or user identification, initiating/finalizing the user consultation, and/or completing the sanitization process. As can be appreciated, the medical assistant or attendant can have other or additional responsibilities (e.g., check operation of veterinary kiosk, report a malfunction of a veterinary kiosk, monitor appointment status of veterinary kiosk, assist the user in the veterinary kiosk, reload software, etc.). The User Appointment or Registration Application can optionally be designed to enable a user to register and schedule appointments through one or more methods (e.g., on-line registration, calling a registration location, visiting a veterinary kiosk, etc.).

During the user registration process, the User Appointment or Registration Application can include scheduling software that provides a scheduling system for a user to register with one or more veterinary kiosks. The scheduling system can be designed to be accessed by a user on a data entry device on a veterinary kiosk, via a computer or phone or smart device, and/or by phone. The user registration system can be designed to 1) schedule a new appointment for a new user, 2) schedule an appointment for a returning user, and/or 3) welcome a user that has already scheduled an appointment. In one non-limiting arrangement, the user registration system generally asks if the user is a returning user, a new user, if the animal is a new or returning animal, or if the user requires assistance. The user registration system generally provides the user with a privacy policy associated with the use of the veterinary kiosk; however, this is not required. When a privacy policy is presented to the user, the user generally must acknowledge or accept the privacy policy before the user can proceed further with the registration process; however, this is not required. The user registration system generally provides the user with terms of service policy associated with the use of the veterinary kiosk; however, this is not required. When the terms of service policy is presented to the user, the user generally must acknowledge or accept the terms of service policy before the user can proceed further with the registration process; however, this is not required. The user registration system generally asks why the user is using the user registration system (e.g., Veterinary kiosk tour, Veterinary kiosk demo, Veterinary kiosk payment demo, check-in for a veterinary visit, etc.). The user registration system generally asks the user to enter a password, phone number, pin number, name, email address, address, date or birth, sex, or the like to identify the user; however, this is not required. The user registration system generally asks the user to verify if the user is at least a certain age (e.g., at least a responsible adult, etc.) before veterinary services can be provided by the veterinary kiosk; however, this is not required. The user registration system generally asks the user to identify one or more symptoms that the animal of the user is experiencing for which the user is seeking veterinary assistance; however, this is not required. The user registration system may optionally ask one or more follow-up questions after the user enters the one or more symptoms and/or may inform the user to seek an in-person visit by a veterinary provider; however, this is not required. The user registration system may optionally ask the user to identify one or more known allergies of the animal of the user; however, this is not required. The user registration system may optionally ask the user to identify one or more known medical conditions of the animal of the user; however, this is not required. The user registration system may optionally ask the user to identify one or more past medical procedures that have been performed on the animal of the user; however, this is not required. The user registration system may optionally ask the user to identify one or more medications the animal of the user is taking; however, this is not required. The user registration system may optionally ask the user if the user has medical insurance; however, this is not required. If medical insurance is inquired about and the user indicates that he/she has medical insurance, the user registration system may optionally ask the user to enter in the medical insurance information (e.g., insurer name, ID number, policy number, etc.) and/or to scan the insurance card; however, this is not required. The user registration system may optionally ask the user to make a co-pay based on the medical insurance or to fully pay for the medical visit; however, this is not required. Such payments, if any, can be by cash, check, debit card, credit card, smart device, etc.). For debit and credit cards and smart devices, the veterinary kiosk may include a card reader or scanner or RFID system, and/or may include a key pad to enter the charge or credit information; however, this is not required. A medical assistant or attendant of the veterinary kiosk can optionally assist the user with the payment of services and/or with any other check-in step of the user registration system; however, this is not required. For example, the user registration system may include a button or other request arrangement to signal to a medical assistance or attendant, if used, that the user need assistance with one or more steps of the registration process; however, this is not required. Once the user is registered, the user registration system will list one or more days and/or times that the veterinary kiosk is available for use by the user; however, this is not required. The time intervals can be spaced by a certain time period (e.g., every twenty minutes, every thirty minutes, etc.); however, this is not required. The user registration system can verify that an appointment has been made by the user once all of the required information and optional payment has been made; however, this is not required. Such verification can be merely displayed on the user registration system, printed out for the user, emailed or texted to the user or left on a voicemail of the user; however, this is not required. If the user is a returning user, the user may merely need to enter the ID information to access the information that user had previously entered and then optionally update such information; however, this is not required. A returning user may be asked about the new visit (e.g., follow-up, new symptoms, etc.); however, this is not required. The returning user may optionally be asked to update insurance information, reenter insurance information, etc. and then optionally make the required copay or full payment. If the returning user is merely returning to a scheduled appointment, the user may need to enter the ID information and verify that the user is present and is checked-in or cancelling the scheduled appointment; however, this is not required. A medical assistant or attendant can optionally provide assistance to a user during any step of the check-in or registration process or recheck-in process; however, this is not required. The information entered and/or scanned regarding the user can optionally be saved to a file for current and/or later access by the user, veterinary provider, medical assistant, etc.; however, this is not required. Such stored information is generally saved on a database, server, etc. that is located remote to the veterinary kiosk; however, this is not required.

In still another and/or alternative non-limiting aspect of the invention, the novel method and apparatus for providing veterinary services, diagnoses, health, and/or wellness advice to individuals can include the use of one or more medical assistants or attendants with the veterinary kiosk; however, this is not required. In one non-limiting embodiment of the invention, the veterinary kiosk can have one or more attendants assist a user during the use of the veterinary kiosk (e.g., assist in check-in procedures, assist check-out procedures, assist in entering/exiting the veterinary kiosk, answering questions about the veterinary kiosk, assist the user about the use of the kiosk, assist the user during examination of the animal of the user by the veterinary provider, assist in maintaining privacy/security of a user while using the veterinary kiosk, assist user during payment of veterinary services, assist user in obtaining a prescription, assist in answering general questions about the veterinary kiosk, assist the remote veterinary provider during the examination of the animal of the user, assist in using one or more medical devices on the animal of the user, cleaning the veterinary kiosk, maintaining the systems of the veterinary kiosk, resetting the veterinary kiosk for use by another user, assist in processing of payments and/or insurance information of a user, monitor proper use of the veterinary kiosk, etc.); however, this is not required. Such attendant, when used, can be a veterinary provider or non-veterinary provider. The assistant may or may not have any formal medical education. The one or more attendants, when used, can also or alternatively clean and/or sanitize various regions of the veterinary kiosk prior to and/or after being used by a user and/or set up the veterinary kiosk for a new user; however, this is not required. For example, prior to and/or after one or more users have entered the veterinary kiosk, the one or more attendants can clean/sanitize one or more exterior surfaces and/or regions of the veterinary kiosk (e.g., veterinary kiosk door, veterinary kiosk check-in terminal, veterinary kiosk desk top, veterinary kiosk exterior walls, veterinary kiosk touch screen, veterinary kiosk monitors, seating/tables in waiting area near veterinary kiosk, etc.); however, this is not required. In an another and/or additional example, prior to and/or after one or more users have entered the veterinary kiosk, the one or more attendants can clean/sanitize one or more interior surfaces of the veterinary kiosk (e.g., veterinary kiosk door, veterinary kiosk floor, veterinary kiosk bench, veterinary kiosk chair, veterinary kiosk user terminal, veterinary kiosk interior desk top, veterinary kiosk interior walls, veterinary kiosk touch screen, veterinary kiosk monitors, veterinary kiosk instrument doors, medical devices/instruments used by and/or touched by user when in the veterinary kiosk, any other surface in the interior of the veterinary kiosk, etc.); however, this is not required.

In still another and/or additional example, prior to and/or after one or more users have entered the veterinary kiosk, the one or more attendants can set up the veterinary kiosk for a user (e.g., clean/sanitize interior surfaces of veterinary kiosk; clean/sanitize medical devices/instruments used and/or touched by a prior user; reposition medical devices/instruments into device storage areas; replace disposable components on medical devices/instruments; replenish paper in a printer; clear a paper jam in a printer; replace batteries for one or more electronic components; close medical device/instrument compartments doors in the veterinary kiosk; retract one or more medical devices back into ceiling or wall; remove one or more medical devices form the kiosk; reset user touch screen for next user in the veterinary kiosk; fix, repair and/or replace non-operating, damaged or broken medical devices/instruments in the veterinary kiosk; fix, repair and/or replace electronic components, computers, fans, light bulbs, UV bulbs, UV devices, etc. in the interior and/or exterior of the veterinary kiosk; refill cleaning and/or sanitizing fluid; etc.); however, this is not required. In yet another and/or additional example, the one or more attendants can be used to assist one or more users in the veterinary kiosk. Generally, such assistance will occur only after requested by the user in the veterinary kiosk or by the veterinary provider that is assisting the user and/or animal while in the veterinary kiosk; however, this is not required. For instance, the one or more attendants can assist a user in the veterinary kiosk if the one or more attendants hear a verbal request from the user, receive notice (e.g., light indicator activated by user, sound indicator activated by user, hear user talking via a speaker to attendant, hear user talking through walls of veterinary kiosk, receive a notice from the veterinary provider [e.g., phone call, email, light indicator, etc.], etc.); however, this is not required. The one or more medical assistants can be positioned at a desk or table that is positioned adjacent to or connected to the exterior of the veterinary kiosk; however, this is not required. The medical assistant can be provided with a computer, tablet, smart phone, etc. to monitor the appointment for the veterinary kiosk, to cancel an appointment, to reschedule and appointment, to indicate if a user missed an appointment or is late for an appointment, to validate the ID of a user, to properly identify the animal, to view appointment information of the veterinary kiosk, to validate a user's insurance, to monitor the need for the assistant to assist a user via user or veterinary provider request, to monitor the status of the visit by the user (e.g., veterinary kiosk cleaned for user, the user has properly checked in, appointment has started and any initial vitals capture process for the animal has begun, vitals capture process for the animal has been completed, verify that the video consultation by veterinary provider with user has begun, verify that the video consultation with the veterinary provider has been completed, verify that the veterinary provider is completing the user report, verify that the visit by the user in the veterinary kiosk is completed, etc.), to assist in insurance and information processing and/or scheduling of a user, to assist in the payment by the user for veterinary services, to print out reports and/or email reports to user that provide a summary or complete report to the user regarding the visit to the veterinary kiosk, to activate the sanitation system of the veterinary kiosk (e.g., UV sanitation system, mist sanitation system, etc.), to keep a record of when the kiosk was cleaned/sanitized and/or what was cleaned/sanitized by the assistant (e.g., clean user counter, clean user touch screen desk, clean user bench, clean animal counter, clean animal scale, clean entry doors, clean one or more of the medical devices used during the examination of the animal, clean user chair, clean interior walls, clean medical doors and handles, clean floor, clean scale, clean video monitor, clean exterior of the veterinary kiosk, clean the medical assistant desk, clean the check-in screen on the exterior of the veterinary kiosk, clean walk-in mat, clean door tracks, clean UV panel, clean inside ceiling, clean top of veterinary kiosk, clean UV lights, clean medical device compartments, clean medical device retraction system, etc.), to enter information about the operation of the veterinary kiosk, to schedule a service call for the veterinary kiosk, to order parts or accessories for the veterinary kiosk, to verify the start and completion of an appointment, to process comment information by a user, to create and/or send reports regarding the use of the veterinary kiosk, to escort the animal and/or user into and/or out of the veterinary kiosk, to begin the vitals capture of the animal of the user, provide information and/or instructions to a user regarding the veterinary kiosk and/or regarding the proper use of the veterinary kiosk, to assist a potential user in a tour of the veterinary kiosk, etc.

In yet another and/or alternative non-limiting aspect of the invention, the novel method and apparatus for providing veterinary services, diagnoses, health, and/or wellness advice to a user can include the use of an Attendant Application. The Attendant Application includes software and/or hardware that enables the attendant to 1) monitor, modify and/or cancel existing appointments for a veterinary kiosk, 2) monitor whether a user requires assistance, 3) monitor and/or assist a user during registration with the veterinary kiosk, 4) provide procedures and/or check lists for the medical assistant, and/or 5) provide information on the status of the veterinary kiosk. As can be appreciated, the Attendant Application can have other and/or additional functions. In one non-limiting arrangement, the initial Attendant Application's screen displays one or more appointment fields (e.g., time, user name, veterinary provider name, name of animal, status, action, etc.). For example, the time field, when used, can be designed to display the time of upcoming appointments on the veterinary kiosk; the user name field, when used, can be designed to display the name of the user for upcoming appointments on the veterinary kiosk, the animal's name field, when used, can be designed to display the name of the animal for upcoming appointments on the veterinary kiosk; the provider name field, when used, can be designed to display the name of the providers for upcoming appointments on the veterinary kiosk; the status field, when used, can be designed to display the status of upcoming appointments on the veterinary kiosk (e.g., Ready—The veterinary kiosk has been sanitized and is ready for the next user appointment, Checked-In—The user has been checked-in and their appointment is pending, Pre Consult—The appointment has started and vitals capture process is in progress, In Visit—The vitals capture process has been completed and the video consultation with the veterinary provider is in progress, Post Consult—The video consultation with the veterinary provider has been completed and the veterinary provider is completing the visit, Completed—The appointment has been completed, etc.), and the actions field, when used, can be designed to display the availability of the Attendant Application functions. The actions field, when used, can be designed to allow for one or more actions (e.g., "X" Icon, Clock Icon, Printer Icon, Emergency Clean-Up Icon, etc.). The "X" Icon, when used, can be design to perform one or more functions, such as to cancel an upcoming appointment; however, this is not required. The "X" Icon can also allow entry and/or selection of a reason for cancellation (e.g., No Show—This action cancels the appointment, but maintains the user record; Can't Make Appointment (Not Rescheduling)—This action cancels the appointment, but maintains the user record; User Changed Mind—This action cancels the appointment, but maintains the user record; Cancel Cancellation—This action cancels the cancellation; etc.). The "Clock" Icon, when used, can be designed to reschedule an upcoming appointment; however, this is not required. When this Icon is selected, entry and/or selection of one or more types of data can be allowed (e.g., input a date and time to reschedule an appointment, etc.); however, this is not required. The "Printer" Icon, when used, can be designed to print a visit summary and/or some other type of information (e.g., prescription, coupons, follow-up visit information, survey and/or survey results, summary of visit and/or other types of visit information, etc.); however, this is not required. This icon can be designed to only appear after an appointment has been completed and/or scheduled; however, this is not required. The "Emergency Clean-Up" Icon, when used, can be designed to allow the veterinary attendant to associate an emergency clean-up with a user appointment so as to be used for tracking purposes and/or some other purpose; however, this is not required. Upon selection of the "Emergency Clean-Up" Icon, the veterinary attendant can be allowed to type a note regarding the emergency clean-up; however, this is not required.

In still yet another and/or alternative non-limiting aspect of the invention, the novel method and apparatus for providing veterinary services, diagnoses, health, and/or wellness advice to a user can include the use of an Attendant Application that allows the veterinary attendant to 1) view appointment information, 2) validate user IDs, 3) validate the identity of the animal, 4) validate user insurance, 5) reschedule or cancel an appointment, and/or 6) perform the sanitization process for the veterinary kiosk; however, this is not required. In one non-limiting embodiment of the invention, once the user is "Checked-In" via the user registration process, the appointment status changes to "Pending." At that time, the veterinary attendant can be required to validate the user's ID and/or the identity of the animal; however, this is not required. For example, the veterinary attendant can 1) select the records of the animal of the user and/or the user (e.g., from the computer screen or monitor, etc.) and 2) select the "Validate User ID" button or similar type of button or selection; however, this is not required. If the user is a new user and/or the animal is new, the veterinary attendant can be prompted to insert and scan the user's identification for the first time to be saved in the user's electronic file and/or animal's file. If the user is a returning user, the veterinary attendant can be prompted to "Update User ID". If "Update User ID" is selected, the veterinary attendant can be prompted to "Start Scan" of updated user ID. Once the user's ID is validated and scanned, the veterinary attendant may be required to rescan the ID (if image quality is compromised) or save the image in the user's file; however, this is not required. Similar procedures can be done for the animal; however, this is not required. As can be appreciated, other or additional methods can be used to validate an animal and/or the user's ID. In one non-limiting arrangement, the user's identification is validated by use of a valid driver's license, US passport, military ID, and/or photo ID card issued by federal, state, or local government. As can be appreciated, other or additional types of IDs can be used. Various ID systems can optionally be used to verify the identity of the animal (e.g., picture of animal, etc.). If the user is under 18 or some other age designating a minor, the user may be required to be accompanied by a parent or legal guardian; however, this is not required. If the user is not accompanied by a parent or legal guardian, the user may not be allowed to proceed with the visit. The medical assistant may be required to inform the under-18 or minor-age user of certain rights when using the veterinary kiosk (e.g., anyone under 18 years of age needs to have parent or legal guardian to use the veterinary kiosk, etc.); however, this is not required. If a new user indicates that they have insurance or a returning user indicates their insurance information has changed, the user may be prompted to see the veterinary attendant and/or be required to enter the insurance information; however, this is not required. The Attendant Application can prompt the veterinary attendant for entry of a co-pay amount and/or to scan the insurance card into the user record; however, this is not required. As can be appreciated, the user can enter the insurance information without a veterinary attendant and/or make a co-payment without the veterinary attendant; however, this is not required. Once the user's insurance is validated and entered and/or scanned, the veterinary attendant or user may be required to rescan the ID (if image quality is compromised) and/or reenter the information if not entered properly or save the image and/or entered insurance information into the user's file; however, this is not required. If the insurance information is not verified at a first try, the user or veterinary attendant can attempt to reverify the insurance information; however, this is not required. Once the user insurance is saved, the user can be prompted to "Check in" for the next available appointment or select some appointment time and/or day in the future; however, this is not required. Once the user is checked-in for a visit to the kiosk, the appointment status will change to "Pre Consult" or some other statement on the screen of the Attendant Application; however, this is not required. At that time, the veterinary attendant may be required to recite a "Pre-Visit Summary" (e.g., "After your appointment is verified, you will step into the veterinary kiosk with you animal, you may optionally capture vitals for your animal, and you will meet with a veterinary provider over a video connection. The veterinary provider will provide the diagnoses and you may receive a prescription. The prescription can be sent to a pharmacy of your choice or provided at the veterinary kiosk, etc.); however, this is not required. Once the user is checked in and after any optional statement is made to the user, the user and animal can enter the veterinary kiosk. The veterinary attendant may be required to escort the user and animal into the veterinary kiosk to initiate the vitals capture of the animal, if any and/or consultation; however, this is not required. The veterinary attendant and/or user can cause the Provider Application to prompt the veterinary provider to start the medical visit; however, this is not required. Once the veterinary provider completes the appointment via the Provider Application, the appointment status on the Attendant Application for a particular user can be designed to change to "Completed".

Once the user visit has completed the medical visit and exited the veterinary kiosk, the veterinary attendant may be required to perform a sanitization process; however, this is not required. Such sanitation process can include the veterinary attendant 1) selecting the user's and/or animal's record on the screen, and 2) selecting the "Start Sanitization" button or similar labeled button or selection. The veterinary attendant can optionally enter the veterinary kiosk and perform the sanitization process. A screen that includes a check list or a paper check list can be used by the veterinary attendant to check off items that have been sanitized; however, this is not required. For example, a screen inside the veterinary kiosk can include a check list and the medical assistant checks off each item as such item is sanitized by the veterinary attendant; however, this is not required. When all items are sanitized and optionally checked off, the veterinary attendant can select a button on the Attendant Application that the sanitation step is completed; however, this is not required. The veterinary attendant can optionally select "Run UV Light" or some other or additional automated sanitation system, if such option is available; however, this is not required. Areas of the veterinary kiosk that can be cleaned after each visit and/or cleaned at period times based on some protocol are: user counter, user monitor screen, physician monitor screen, user chair, animal bench, animal scale, animal examining area, seat at rear of station, kiosk wall panels, medical devices, medical device doors and handles, interior of kiosk, entry door of kiosk, internal wood surfaces in kiosk, attendant station, walk in door mat, floor of kiosk, door track of kiosk, external display monitor of kiosk, external surfaces of kiosk, UV panel in kiosk, and/or UV lights. The surfaces can be cleaned with wipes (e.g., Virox wipes [towelettes with disinfecting chemicals that kill 99% of viruses and bacteria]), glass cleaner, surface cleaners, floor cleaners, duster, dusting cloth, etc. Upon completion of the sanitization process, the veterinary kiosk status can return to "Ready" on the Attendant Application; however, this is not required. At that point, the veterinary attendant can start validation of the next animal and/or user's ID.

In another and/or alternative non-limiting aspect of the invention, the novel method and apparatus for providing veterinary services, diagnoses, health, and/or wellness advice to individuals can include the use of a user Appointment or Registration Application to navigate the user through the animal's vitals capture process, user consultation, and/or survey; however, this is not required. The User Appointment or Registration Application can contain one or more navigational buttons on the user screen that is located inside the veterinary kiosk (e.g., Back, Next, Cancel, Request Assistance, etc.); however, this is not required. The "Back" button, when used, allows the user to return to the previous screen. The "Next" button, when used, allows the user to proceed to the next screen. The "Cancel" button, when used, allows the user to cancel a process and return to the beginning of the process. The user can optionally receive a request to confirm the cancel procedure; however, this is not required. The "Request Assistance" button, when used, allows the user to request assistance from the veterinary attendant. The selection of this button can be designed to also notify the user that the veterinary attendant will be with them in a moment; however, this is not required. The selection of the "Request Assistance" button by the user can result in the Attendant Application displaying on a screen a notice or generating a warning sound, etc. that the user has requested assistance. For example, when the user initiates the "Request Assistance" button, a pop-up box (e.g., orange box, red box, blue box, etc.) can appear on the veterinary attendant's screen that is labeled "kiosk," colored orange, and indicates the user requires assistance. As can be appreciated, the screen of the Provider Application, when used, can include an "Alert Attendant" button to notify the veterinary attendant that the user requires assistance; however, this is not required. If the veterinary provider initiates the "Alert Attendant" button from the Provider Application, a pop-up box can be designed to appear on the veterinary attendant's screen that indicates the user requires assistance. The pop-up box can be a colored box (e.g., red box, green box, orange box, etc.); however, this is not required. A sound can also or alternatively be generated by the Attendant Application, when used, to notify the veterinary attendant that the veterinary provider has selected the "Alert Attendant" button; however, this is not required. The User Appointment or Registration Application, when used, can be designed to allow the user to 1) capture vitals, 2) perform the provider consultation, and/or 3) perform the survey. As can be appreciated, the User Appointment or Registration Application, when used, can be designed to allow the user to perform other or additional functions. The User Appointment or Registration Application can be designed to appear on the User Screen and/or Provider Screen that are located in the interior of the veterinary kiosk; however, this is not required. The Provider Screen, when used, is the screen that is located above or adjacent to the User Screen; however, this is not required. As can be appreciated, only a Provider Screen can be located in the veterinary kiosk; however, this is not required. The veterinary provider generally appears on the Provider Screen when the consultation starts; however, this is not required. The User Screen, when used, can provide information to the user while located in the kiosk and/or allow the user to enter information (e.g., user receives vitals capture instructions for the animal on the User Screen and enters information as prompted, etc.).

The User Appointment or Registration Application can be designed to capture vitals of the animal of the user. The User Appointment or Registration Application can be designed to require the user to initiate the capture vitals procedure and/or the veterinary attendant to initiate the capture vitals procedure for the animal of the user. The User Appointment or Registration Application can be designed to navigate the user and/or provide instructions to the user for one or more of the vitals capture procedures of the animal; however, this is not required. During the vitals capture process, the user can request that the medical assistant assist the user in one or more of the procedures for capturing the vitals of the animal; however, this is not required. The User Appointment or Registration Application can be designed to require the user to confirm that instructions for a particular vital capture procedure have been read and/or understood before proceeding with the next vitals capture step; however, this is not required. The User Appointment or Registration Application can be designed to have the user enter the animal's height on the Provider Screen and/or User Screen; however, this is not required. The interior of the veterinary kiosk can include a height marker or height tape to enable a user to determine the height of the animal; however, this is not required. The veterinary kiosk can include a camera or some other type of arrangement that can be used to automatically determine the height of the animal of the user while the animal is positioned in the veterinary kiosk, and/or be used to facilitate in the examination of the animal; however, this is not required. The one or more cameras in the kiosk, when used, can be moveable or fixed. The User Appointment or Registration Application can be designed have the user enter the weight of the animal and/or other or additional information about the animal on the Provider Screen and/or User Screen; however, this is not required. The interior of the veterinary kiosk can include a scale (e.g., built-in floor scale, bench scale, examination table scale, etc.) that can be used by the user to determine the weight of the animal; however, this is not required. When a scale is provided in the veterinary kiosk, the weight can be automatically transferred to the User Appointment or Registration Application and/or can be manually entered by the user. As can be appreciated, the scale can be located outside the kiosk; however, this is not required. The scale, when located outside the kiosk, can be brought inside the kiosk and/or used outside the kiosk. The scale, when used, can send information by a wired and/or wireless connection to the kiosk or other locations; however, this is not required. The User Appointment or Registration Application can be designed to have the user obtain the temperature of the animal; however, this is not required. The User Appointment or Registration Application or Provider Application can be designed to open a medical device cabinet that contains a thermometer; however, this is not required. The User Appointment or Registration Application can be designed to provide instructions and/or a video on how to use the thermometer (e.g., a) remove thermometer from open medical cabinet, b) position the thermometer on the animal, c) remove thermometer from the animal after hearing a beep sound or other indicator that indicates procedure is completed, d) return thermometer to medical cabinet, etc.); however, this is not required. The User Appointment or Registration Application can be designed to have the user obtain the blood pressure of the animal; however, this is not required. The User Appointment or Registration Application can be designed to open a medical device cabinet that contains a blood pressure cuff and/or allows the blood pressure cuff to be plugged into the veterinary kiosk; however, this is not required. The User Appointment or Registration Application can be designed to provide instructions and/or a video on how to use the blood pressure cuff; however, this is not required. As can be appreciated, the veterinary attendant can place the blood pressure cuff on the animal prior to or while the animal is located in the veterinary kiosk; however, this is not required. If the blood pressure cuff requires that it be connected to the veterinary kiosk, the veterinary attendant or the user can perform such connection. The user or the veterinary attendant can start the blood pressure reading by selecting a button on the User Appointment or Registration Application; however, this is not required. The blood pressure cuff, when used, can be used to measure the blood pressure/heart rate of an animal. A real-time reading of the blood pressure/heart rate of the animal can be displayed on the User Screen and/or Provider Screen; however, this is not required. The user or veterinary attendant or veterinary provider can stop the process of capturing the blood pressure/heart rate of the user; however, this is not required. After the completion of capturing all the vitals of the animal, if such vitals are collected, the User Appointment or Registration Application can be designed to display on the User Screen and/or Provider Screen a summary of one or more of the captured vitals of the animal. The User Appointment or Registration Application can be designed to allow the user to manually change one or more of the collected vitals, if any such vitals are taken; however, this is not required. Once the vital capture process for the animal is completed, the user can be prompted (e.g., "I'm Ready" button, etc.) to indicate that the user is ready for the conference with the veterinary provider; however, this is not required. The User Appointment or Registration Application can be designed to notify the user that the veterinary provider will be with them shortly; however, this is not required. Once the consultation has begun, the User Appointment or Registration Application can be designed to cause the veterinary provider to appear on one or more portions of the Provider Screen (e.g., lower portion, etc.) and the vitals of the animal can optionally appear on the one or more portions of the Provider Screen (e.g., upper portions, etc.); however, this is not required. As can be appreciated, the full Provider Screen can only include the veterinary provider. The User Appointment or Registration Application can be designed to allow the user to adjust the volume by use of volume buttons on the User Screen; however, this is not required. As can be appreciated, volume control can be located in other or additional locations in the veterinary kiosk. After the completion of the consultation, the User Appointment or Registration Application can be designed to ask the user to complete a survey; however, this is not required. The User Appointment or Registration Application can be designed to allow the user to skip the survey, when used, or to proceed with the survey; however, this is not required. If the user selects the survey, when offered, one or more questions can be displayed on the User Screen and/or Provider Screen; however, this is not required. As can be appreciated, the veterinary attendant can provide the user with a written survey and/or ask verbal survey questions; however, this is not required. At the completion of the survey, or if the user chooses to skip the survey when such survey is offered, the User Appointment or Registration Application can be designed display a final screen thanking the user for his/her visit and/or prompting them to request a visit summary from the veterinary attendant; however, this is not required.

In still another and/or alternative non-limiting aspect of the invention, the novel method and apparatus for providing veterinary services, diagnoses, health, and/or wellness advice to individuals can include the use of a Provider Application that is designed to enable the veterinary provider to navigate through the appoint process during the user appointment. The Provider Application can be designed to allow the veterinary provider to a) display the appointment information, b) display user information, c) display animal's information, d) view and/or modify visit information, e) perform the consultation, and/or f) utilize one or more medical devices in the veterinary kiosk. The Provider Application can be designed to cause screens to appear on the veterinary provider's computer, smart phone, tablet, etc. at the veterinary provider's remote location; however, this is not required. Upon entering the Provider Application by the veterinary provider, the Provider Application can be designed to enable the veterinary provider to view appointments that have been completed by the veterinary provider, that are in progress by the veterinary provider and/or which are future appointments. In one non-limiting arrangement, the Provider Application can be designed to enable the veterinary provider to view appointments that have been completed by the veterinary provider or are in in progress for a certain day (e.g., today, last Monday, etc.). In another non-limiting arrangement, the Provider Application can be designed to enable the veterinary provider to view appointments that have been made for a future time (e.g., two hours from the present, the next day, etc.). For example, the Provider Application can be designed to display on one portion of the screen (e.g., left side, right side, center, etc.) appointments for "Today" and "Future." In one non-limiting arrangement, the "Today" tab can be designed to display one or more types of user appointment information (e.g., Time—Time of appointment, User Name—User name for appointment, Animal's Name—Name of the animal, Status—Status of appointment, Pending—User started the registration process, but has not yet been approved for payment, Checked-In—User has been checked-in, Pre Consult—Appointment has started and vitals are being collected for the animal, In Visit—Vitals have been collected for the animal and the video consultation is in-progress, Post Consult—Video consultation has been completed and veterinary provider completion is pending, Completed—Appointment has been completed, etc.). The "Future" tab can be designed to display one or more types of user appointment information (e.g., Date—Date of appointment, Time—Time of appointment, User Name—User name for appointment, Animal's Name—Animal's name for appointment, etc.). The Provider Application can be designed to enable the veterinary provider to view a selected record on another portion of the screen and/or other screens; however, this is not required. The selected record can provide the veterinary provider one or more types of information (e.g., User name, Animal's name, Animal's date of birth, Type of animal, Breed of animal, Animal's sex, Animal's symptoms, Animal's medical conditions, Date of last visit, Diagnosis, Allergies, Medications, Prior visit record of animal, Medical records of animal, etc.). The Provider Application can be designed to enable the veterinary provider to notify the veterinary attendant that the user requires assistance; however, this is not required. The Provider Application can be designed to enable the veterinary provider to view the appointment and/or user information and/or animal's information prior to the visit and/or prior to the vitals capture process, if any. The Provider Application can be designed to limit access to a user's and/or animal's information until a certain point (e.g., user status is "Checked-In", etc.); however, this is not required. The Provider Application can be designed to enable the veterinary provider to refuse an appointment that has been created for the veterinary provider; however, this is not required. Generally, such refusal should occur prior to the user status of "Checked-In" to enable the system to locate another available veterinary provider; however, this is not required. The Provider Application can be designed to allow the veterinary provider to begin the conference with the user once the user is ready in the veterinary kiosk (e.g., after "Check-In", after "Capture of Vitals", etc.); however, this is not required. The Provider Application can be designed to cause a "Start Visit" button or similar button to appear on the veterinary provider's screen to allow the veterinary provider to begin the consultation with user; however, this is not required. Once the visit or consultation has been initiated, the Provider Application can be designed to update the appointment status to "In Visit"; however, this is not required. Once the visit or consultation has begun, the user and/or animal appears on a portion of the veterinary provider's screen (e.g., right side of screen, center of screen, left side of screen, etc.); however, this is not required. The veterinary provider may greet the user in the veterinary kiosk with a greeting (e.g., "Welcome to HealthSpot's Station at _____, can you see me ok? Can you hear me ok?", etc.); however, this is not required. The Provider Application can be designed to cause an "End Consultation" or similar button to appear on the veterinary provider's screen to terminate the consultation or visit with the user and thereby terminate the video link between the veterinary provider and user in the veterinary kiosk; however, this is not required. Once the consultation or visit with the user is terminated, the Provider Application can be designed to cause the status of the user to change to "Post Consult"; however, this is not required. "Post Consult" means the video consultation has been completed and the veterinary provider is completing the visit summary. Once the veterinary provider has completed the visit summary and written any required prescriptions, the Provider Application can be designed to cause a "Complete Appointment" or similar button to appear on the veterinary provider's screen; however, this is not required. The selection of the "Complete Appointment" button or similar button after completion of the video consultation can result in the status of the user to change to "Completed"; however, this is not required. "Completed" means the veterinary provider has completed input of all information and is ready to commence the next appointment. The Provider Application can be designed to allow the veterinary provider to view the animal's records, including the vitals capture process, if any, that has occurred or is occurring in the veterinary kiosk. The Provider Application can be designed to cause one or more tabs to be displayed on the veterinary provider's screen once an animal's record has been selected (e.g., User information, Animal's information, Current visit, Previous visit, etc.). The "User Information" tab and/or "Animal's Information" tab, when used, can list one or more types of information of the user and/or animal on the veterinary provider's screen (e.g., Personal Information of User, Personal Information of Animal, Medications of Animal, Allergies of Animal, Medical Conditions of Animal, etc.). One or more of these categories of information can be further expanded upon selection by the veterinary provider; however, this is not required. For example, selection of the Personal Information of Animal category can cause further information about the animal to be displayed (e.g., animal's date of birth, animal's sex, type of animal, breed of animal, prior medications used by animal, prior medical conditions of animal, etc.); however, this is not required. The "Current Visit" tab, when used, can list one or more types of information of the animal on the veterinary provider's screen (e.g., Medications, Notes, Vitals, Devices, Visit Summary, Attendant Instruction, etc.). One or more of these categories of information can be further expanded upon selection by the veterinary provider; however, this is not required. For example, selection of the Medications category can cause further information about medications used by the animal (e.g., past medications used, past medications prescribed to animal, current medications used by the animal, etc.). The "Previous Visit" tab, when used, can list one or more types of information of the animal on the veterinary provider's screen (e.g., Symptoms, Notes, Vitals, Visit Summary, etc.). One or more of these categories of information can be further expanded upon selection by the veterinary provider; however, this is not required. For example, selection of the Vitals category can cause further information about the vitals that were captured during a previous visit to the current veterinary kiosk, some other veterinary kiosk, or at some other medical facility. In one non-limiting embodiment of the invention, the Provider Application is designed to cause at least three tabs to be displayed on the veterinary provider's screen once an animal's record has been selected, namely Animal's Information, Current Visit, and Previous Visit. The "Animal's Information" tab can be designed to contain sections for Personal Information, Medications, Allergies, and Medical Conditions; however, it can be appreciated that other or additional tab sections can be included. The "Personal Information" section contains one or more sub-sections, of which some or all the information about the animal was entered by the user during the registration process. This information generally cannot be modified by the veterinary provider; however, this is not required. Non-limiting examples of information that can be displayed in the "Personal Information" section includes Date of Birth, Gender—Male or Female, Type of Animal, Breed of Animal, Eye Color of Animal, Hair Color of Animal, Length/Height of Animal, Address, etc.). The "Medications" section allows the veterinary provider to see previously entered medications, search and select new medications, and/or remove medications the animal is no longer taking. The Provider Application can be designed to allow a veterinary provider to add a medication by having the veterinary provider type in the medication and/or to start typing the medication name in the "Search Medications" drop-down and allow a listing of matching medication names to appear for selection and then to select the proper medication. The Provider Application can be designed to allow a veterinary provider to delete a medication by having the veterinary provider select an "X" next to the medication. As can be appreciated, other or additional arrangements can be used to add and/or delete medications in an animal's record. The "Allergies" section allows the veterinary provider to view allergies of the animal as input by the user. This function allows the veterinary provider to see previously entered allergies, search and select new allergies, and/or remove allergies. The Provider Application can be designed to allow a veterinary provider to add an allergy by having the veterinary provider type in the allergy and/or to start typing the allergy name in the "Add Allergy" drop-down and allow a listing of matching allergy names to appear for selection and then to select the proper allergy. The Provider Application can be designed to allow a veterinary provider to delete an allergy by having the veterinary provider select an "X" next to the allergy. As can be appreciated, other or additional arrangements can be used to add and/or delete allergies in an animal's record. The "Medical Conditions" section allows the veterinary provider to view animal's medical conditions as input by the user. This function allows the veterinary provider to see previously entered medical conditions, search and select new medical conditions, and/or remove medical conditions. The Provider Application can be designed to allow a veterinary provider to add a medical condition by having the veterinary provider type in the medical condition and/or to start typing the medical condition in the "Add Medical Condition" drop down and allow a listing of matching medical condition names to appear for selection and then to select the proper medical condition. The Provider Application can be designed to allow a veterinary provider to delete a medical condition by having the veterinary provider select an "X" next to the medical condition. As can be appreciated, other or additional arrangements can be used to add and/or delete medical conditions in an animal's record. The "Current Visit" tab can contain sections for Symptoms, Notes, Vitals, Devices, Visit Summary, and Attendant; however, it can be appreciated that other or additional tab sections can be included. The "Symptoms" section contains all of the animal's symptoms for the current visit as input by the user. This function allows the veterinary provider to see entered symptoms, search and select new symptoms, and remove symptoms. The Provider Application can be designed to allow a veterinary provider to add a symptom by having the veterinary provider type in the symptom and/or to start typing the symptom in the "Symptoms" drop-down and allow a listing of matching symptom names to appear for selection and then to select the proper symptom. The Provider Application can be designed to allow a veterinary provider to delete a symptom by having the veterinary provider select an "X" next to the symptom. As can be appreciated, other or additional arrangements can be used to add and/or delete symptoms in an animal's record. The "Notes" section allows the veterinary provider to enter notes for the current visit. This information generally does not appear on the Appointment Summary and is intended for internal reference only; however, this is not required. The Provider Application can be designed to allow a veterinary provider to add or delete a note by typing a note in the note text box or by deleting a note in the note text box. As can be appreciated, other or additional arrangements can be used to add and/or delete notes in an animal's record. The "Vitals" section contains the animal's vitals, if any, for the current visit. Such information can optionally be displayed dynamically on the provider's screen as the vitals capture process takes place; however, this is not required. This function allows the veterinary provider to see the vitals prior to starting and during the consultation; however, this is not required. This information is generally only displayed and cannot be updated; however, this is not required. Non-limiting vitals can include Height, Weight, Blood Pressure, Heart Rate, Oxygen Saturation, and Temperature. The "Devices" section contains icons of the medical devices that are located in the veterinary kiosk, if any, and/or can be used with the veterinary kiosk. On the interior of the veterinary kiosk there can be one or more medical cabinets (e.g., 1-10, 2, 4, 6, etc.), wherein one or more can be optionally locked upon user entry into the veterinary kiosk. The veterinary provider has the capability to unlock one or more of the medical cabinets in the veterinary kiosk as necessary; however, this is not required. When the veterinary provider wants to unlock a medical device cabinet, the veterinary provider clicks on or selects the appropriate medical device icon on the veterinary provider's computer screen. This selection can result in the activation of the medical device and/or the opening of the medical cabinet door that includes the selected medical device. An audible sound can be generated (e.g., sound of dropping door, sound of a lock unlocking, etc.) when access to a medical cabinet is granted to a user; however, this is not required. As can be appreciated, a visual indicator can also or alternatively be used to indicate that a user can access a particular medical cabinet; however, this is not required. Non-limiting medical devices included in the veterinary kiosk can be selected by the veterinary provider for use in a user visit (otoscope, dermascope, thermometer, blood pressure monitor, stethoscope, cameras in various positions, microphone, stadiometer/height gauge, grooming tools, other devices as required by the provider, etc.). As can be appreciated, the veterinary attendant can provide one or more medical devices to a user prior to and/or during the visit; however, this is not required. The "Visit Summary" section is can be comprised of one or more sub-sections, some or all of which are input by the veterinary provider (e.g., Current Diagnoses, Treatment Plan, Follow-Up Care, Visit Documents, etc.). The "Current Diagnoses" section, when used, allows for the provider to input diagnoses codes and descriptions for the current visit. The veterinary provider can update and/or enter a diagnosis by entering the name of the diagnoses and/or an ICD code in a drop-down menu and/or search menu. Once the diagnoses name has been entered and/or searched and located, the veterinary provider can add the diagnoses to the animal's record. More than one diagnosis can be added to an animal's record during a single visit. Once the one or more diagnoses are entered, such diagnoses can be optionally displayed under the "Current Diagnoses" section. The "Treatment Plan" section, when used, allows for the veterinary provider to input a treatment plan for the current visit. Such treatment plan can be typed by the veterinary provider into a text box and this information can appear on the Appointment Summary for the user to reference; however, this is not required. The "Follow-Up Care" section, when used, allows for the veterinary provider to input follow-up care for the current visit. Such follow-up care plan can be typed by the veterinary provider into text box; however, this is not required. This information can appear on the Appointment Summary for the user to reference; however, this is not required. The "Visit Documents" section, when used, allows for the veterinary provider to input follow-up care for the current visit. The veterinary provider can include one or more visit documents and/or other types of documents (e.g., documents about fleas, grooming, feeding, discipline, potty training, etc.) which can be provided to the user along with the Appointment Summary; however, this is not required. The "Attendant Instructions" section, when used, allows for the veterinary provider to input attendant instructions for the current visit. Such information can be entered into a text box by the veterinary provider. This information may or may not be provided to the user. The "Previous Visit" tab contains information about prior medical visits by the animal. When the "Previous Visit" tab is selected, a drop-down box appears containing the dates of all previous visits. The veterinary provider can select a previous visit and then review information about the previous visit. In one non-limiting arrangement, when the previous visit date is selected, one or more sections are displayed (e.g., Symptoms, Notes, Vitals, Visit summary, etc.). The "Symptoms" section, when used, allows for the veterinary provider to view all of the animal's symptoms from the previous visit as input by the user and/or veterinary provider. The "Notes" section, when used, allows the veterinary provider to view all notes for the previous visit that were inputted by the veterinary provider in the prior visit. The "Vitals" section, when used, allows for the veterinary provider to view all of the animal's vitals that were captured during a previous visit. The "Visit Summary" section, when used, allows for the veterinary provider to view all visit summary information input during a prior visit. This section can include one or more subsections (e.g., Treatment Plan, Follow-up Care, Visit Documents, etc.).

In yet another and/or alternative non-limiting aspect of the invention, the novel method and apparatus for providing veterinary services, diagnoses, health, and/or wellness advice to individuals can include a method and a kiosk wherein before the video-conference between the veterinary provider and the user begins, the visit starts with a Vitals Check of the animal to capture one or more of the following: Height, Weight, Temperature, Blood Pressure and/or Heart Rate.

In still yet another and/or alternative non-limiting aspect of the invention, the novel method and apparatus for providing veterinary services, diagnoses, health, and/or wellness advice to individuals can include a method and a kiosk wherein the kiosk includes one or more advanced medical device cabinets which are locked upon user entry in the veterinary kiosk; however, this is not required. During the user consultation, the veterinary provider has the capability to unlock and/or open one or more of these cabinets from the Provider Application on the Provider's computer. The following medical devices can be contained within the cabinets, namely a stethoscope, an otoscope, a thermometer, a dermascope, a stadiometer/height gauge, a blood pressure monitor, and/or one or more grooming tools. Other and/or alternative medical devices can be included in the veterinary kiosk (e.g., a scale, height tape, etc.).

The stethoscope, when used, is used for detecting sounds produced in the body of the animal. The veterinary kiosk stethoscope sounds are transmitted from the stethoscope in the medical device (e.g., hardwire, USB™, Bluetooth™, wireless, etc.) to the veterinary provider's stethoscope. On the interior of the veterinary kiosk, the stethoscope can be contained in the first medical device cabinet on the left; however, this is not required. The stethoscope can be activated by the veterinary provider via the Provider Application by the veterinary provider selecting the stethoscope icon on the provider's screen; however, the stethoscope can be activated by other or additional arrangements. In one non-limiting arrangement, when the veterinary provider via the Provider Application selects the stethoscope icon on the provider's screen, the stethoscope in the veterinary kiosk is activated and the cabinet door in the veterinary kiosk for the stethoscope opens or drops down to enable the user in the veterinary kiosk to access the stethoscope; however, this is not required. The veterinary provider can provide instructions to the user on how to use the stethoscope and/or instructions for use of the stethoscope can be provided on the User Screen and/or Provider Screen in the veterinary kiosk; however, this is not required. When the stethoscope is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the stethoscope and/or video camera in the veterinary kiosk for placement in the animal's file; however, this is not required. The veterinary provider via the Provider Application can optionally annotate an image once captured (e.g., use the paint brush and font icons to modify image, etc.) and/or show the captured image to the user; however, this is not required. The veterinary provider via the Provider Application can increase and/or decrease the volume received from the stethoscope; however, this is not required. As can be appreciated, the user can increase and/or decrease the volume from the stethoscope; however, this is not required. The veterinary provider and/or user can request assistance by the medical assistant related to the use of the stethoscope, if so required.

The otoscope, when used, is a device used for examining the internal ear of the animal. The image generated by the otoscope in the veterinary kiosk can be displayed on the User's Screen and/or Provider's Screen in the veterinary kiosk and/or on the screen being used by the veterinary provider; however, this is not required. The transmission of the signal can be by various means (e.g., hardwire, USB™, Bluetooth™, wireless, etc.). On the interior of the veterinary kiosk, the otoscope can be contained in the second medical device cabinet on the left in the veterinary kiosk; however, this is not required. The otoscope can be activated by the veterinary provider via the Provider Application by the veterinary provider selecting the otoscope icon the provider's screen; however, the otoscope can be activated by other or additional arrangements. In one non-limiting arrangement, when the veterinary provider via the Provider Application selects the otoscope icon on the provider's screen, the otoscope in the veterinary kiosk is activated and the cabinet door in the veterinary kiosk for the otoscope opens or drops down to enable the user in the veterinary kiosk to access the otoscope; however, this is not required. The veterinary provider can provide instructions to the user on how to use the otoscope (e.g., Once the user has pulled out the device, request for user to place the otoscope in the appropriate ear or the animal, then adjust the focus dial. The focus dial is on the top of the otoscope. The user can push it to the top and then dial it down to determine to focus. A request can be made to direct the user to maneuver the otoscope for best image capture. Once the device is in the animal's ear canal, the user can be instructed to move the device towards the front, back, bottom, and top of the ear, etc.) and/or instructions for use of the otoscope can be provided on the User Screen and/or Provider Screen in the veterinary kiosk; however, this is not required. When the otoscope is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the otoscope and/or video camera in the medial kiosk for placement in the animal's file; however, this is not required. The veterinary provider via the Provider Application can optionally annotate an image once captured (e.g., use the paint brush and font icons to modify image, etc.) and/or show the captured image to the user; however, this is not required. The veterinary provider via the Provider Application can adjust the focus of the otoscope; however, this is not required. As can be appreciated, the user can adjust the focus of the otoscope; however, this is not required. The veterinary provider and/or user can request assistance by the medical assistant related to the otoscope if so required.

The thermometer, when used, is used for detecting the animal's internal heat. The temperature that is transmitted by the thermometer can be displayed on the User's Screen and/or Provider's Screen in the veterinary kiosk and/or on the screen being used by the veterinary provider; however, this is not required. The transmission of the signal can be by various means (e.g., hardwire, USB™, Bluetooth™, wireless, etc.). On the interior of the veterinary kiosk, the thermometer can be contained in the third medical device cabinet on the left in the veterinary kiosk; however, this is not required. The animal's temperature can be collected during the vitals capture process which is prior to the consultation with the veterinary provider; however, this is not required. If the veterinary providers wants the temperature to be retaken or if the temperature of the animal has not already been taken, the thermometer can be activated or reactivated by the veterinary provider via the Provider Application by the veterinary provider selecting the thermometer icon on the provider's screen; however, the thermometer can be activated by other or additional arrangements. In one non-limiting arrangement, when the veterinary provider via the Provider Application selects the thermometer icon on the provider's screen, the thermometer in the veterinary kiosk is activated and the cabinet door in the veterinary kiosk for the thermometer opens or drops down, if not already open, to enable the user in the veterinary kiosk to access the thermometer; however, this is not required. The veterinary provider can provide instructions to the user on how to use the thermometer (e.g., Once the user has pulled out the device, request for user to turn on the thermometer. The "On" button is on the inside handle of the device. Request for the user to insert the thermometer into the animal's ear and press the button on top of the handle to start the reading. Once the animal's temperature is collected, a beep will sound. Once the beep is sounded to indicate the temperature reading has completed, the user can hit the "Temperature Recorded" button on the user screen, etc.) and/or instructions for use of the thermometer can be provided on the User Screen and/or Provider Screen in the veterinary kiosk; however, this is not required. When the thermometer is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the thermometer and/or video camera in the veterinary kiosk for placement in the animal's file; however, this is not required. The veterinary provider via the Provider Application can optionally annotate an image once captured (e.g., use the paint brush and font icons to modify image, etc.) and/or show the captured image to the user; however, this is not required. The veterinary provider and/or user can request assistance by the medical assistant if so required. In one non-limiting arrangement, the temperature must register between certain values for certain types of animals, or an error will be indicated to request the user to manually enter the temperature, request the user to try again to take a proper temperature, and/or request the veterinary assistant to assist the user in the use of the thermometer; however, this is not required.

The dermascope, when used, is used to visualize body surface, skin, hair, scalp, eyes, and/or throat of the animal with magnification and/or illumination. The image generated by the dermascope in the veterinary kiosk can be displayed on the User's Screen and/or Provider's Screen in the veterinary kiosk and/or on the screen being used by the veterinary provider; however, this is not required. The transmission of the signal can be by various means (e.g., hardwire, USB™, Bluetooth™, wireless, etc.). On the interior of the veterinary kiosk, the dermascope can be contained in the first medical device cabinet on the right in the veterinary kiosk; however, this is not required. The dermascope can be activated by the veterinary provider via the Provider Application by the veterinary provider selecting the dermascope icon on the provider's screen; however, the dermascope can be activated by other or additional arrangements. In one non-limiting arrangement, when the veterinary provider via the Provider Application selects the dermascope icon on the provider's screen, the dermascope in the veterinary kiosk is activated and the cabinet door in the veterinary kiosk for the dermascope opens or drops down to enable the user in the veterinary kiosk to access the dermascope; however, this is not required. The veterinary provider can provide instructions to the user on how to use the dermascope (e.g., Once the user has pulled out the device, request for user to place the dermascope device at the appropriate place on the animal, and then request the user to adjust the focus dial. The focus dial is on the top handle of the dermascope. The user can push it to the top and then dial it down to determine appropriate focus, etc.) and/or instructions for use of the dermascope can be provided on the User Screen and/or Provider Screen in the veterinary kiosk; however, this is not required. When the dermascope is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the dermascope and/or video camera in the medial kiosk for placement in the animal's file; however, this is not required. The veterinary provider via the Provider Application can optionally annotate an image once captured (e.g., use the paint brush and font icons to modify image, etc.) and/or show the captured image to the user; however, this is not required. The veterinary provider via the Provider Application can adjust the focus of the dermascope; however, this is not required. As can be appreciated, the user can adjust the focus of the dermascope; however, this is not required. The veterinary provider and/or user can request assistance by the veterinary assistant in use of the dermascope if so required.

The stadiometer/height gauge, when used, is used for measuring the height of the animal. The information generated by the stadiometer/height gauge in the veterinary kiosk can be displayed on the User's Screen and/or Provider's Screen in the veterinary kiosk and/or on the screen being used by the veterinary provider; however, this is not required. The transmission of the signal can be by various means (e.g., hardwire, USB™, Bluetooth™, wireless, etc.). On the interior of the veterinary kiosk, the stadiometer/height gauge can be contained in the second medical device cabinet on the right in the veterinary kiosk; however, this is not required. The stadiometer/height gauge can be activated by the veterinary provider via the Provider Application by the veterinary provider selecting the stadiometer/height gauge icon on the provider's screen; however, the stadiometer/height gauge can be activated by other or additional arrangements. In one non-limiting arrangement, when the veterinary provider via the Provider Application selects the stadiometer/height gauge icon on the provider's screen, the stadiometer/height gauge in the veterinary kiosk is activated and the cabinet door in the veterinary kiosk for the stadiometer/height gauge opens or drops down to enable the user in the veterinary kiosk to access the stadiometer/height gauge; however, this is not required. The veterinary provider can provide instructions to the user on how to use the stadiometer/height gauge and/or instructions for use of the stadiometer/height gauge can be provided on the User Screen and/or Provider Screen in the veterinary kiosk; however, this is not required. When the stadiometer/height gauge is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture data generated by the stadiometer/height gauge in the medial kiosk for placement in the animal's file; however, this is not required. The veterinary provider and/or user can request assistance by the veterinary assistant related to the use the stadiometer/height gauge if so required.

The blood pressure cuff or monitor, when used, is used to determine the arterial pressure of the systemic circulation of the animal. The information that is transmitted by the blood pressure cuff can be displayed on the User's Screen and/or Provider's Screen in the veterinary kiosk and/or on the screen being used by the veterinary provider; however, this is not required. The transmission of the signal from the scale can be by various means (e.g., hardwire, USB™, Bluetooth™, wireless, etc.). On the interior of the veterinary kiosk, the blood pressure cuff can be contained in the third medical device cabinet on the right in the veterinary kiosk; however, this is not required. Alternatively, the blood pressure cuff can be kept with the veterinary attendant, and the veterinary attendant then assists the user in placing the blood pressure cuff on the animal prior to the animal entering the veterinary kiosk or while the animal is located in the veterinary kiosk; however, this is not required. The animal's blood pressure can be collected during the vitals capture process which is prior to the consultation with the veterinary provider; however, this is not required. If the veterinary providers wants the animal's blood pressure to be retaken or if the animal's has not already been taken, the blood pressure cuff can be activated or reactivated by the veterinary provider via the Provider Application by the veterinary provider selecting the blood pressure cuff icon the provider's screen; however, the blood pressure cuff can be activate by other or additional arrangements. In one non-limiting arrangement, when the veterinary provider via the Provider Application selects the blood pressure cuff icon on the provider's screen, the blood pressure cuff in the veterinary kiosk is activated and the cabinet door in the veterinary kiosk for the blood pressure cuff opens or drops down to enable the user in the veterinary kiosk to access the blood pressure cuff; however, this is not required. As can be appreciated, if the blood pressure cuff is not located in a medical cabinet, that user can obtain the blood pressure cuff from the location in which the blood pressure cuff currently exists in the veterinary kiosk or the medical assistant can provide the blood pressure cuff to the user if the veterinary attendant is retaining the blood pressure cuff. Information to and from the blood pressure cuff, when used, can be transmitted by wire and/or wirelessly to one or more computers, processors, storage devices, etc. in the veterinary kiosk and/or to a location remote from the veterinary kiosk. The blood pressure cuff can be designed to be activated/deactivated by the user and/or remotely by the veterinary provider and/or veterinary kiosk assistant. The veterinary provider can provide instructions to the user on how to use the blood pressure cuff and/or instructions for use of the blood pressure cuff can be provided on the User Screen and/or Provider Screen in the veterinary kiosk; however, this is not required. When the blood pressure cuff is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the blood pressure cuff and/or video camera in the medial kiosk for placement in the animal's file; however, this is not required. The veterinary provider via the Provider Application can optionally annotate an image once captured (e.g., use the paint brush and font icons to modify image, etc.) and/or show the captured image to the user; however, this is not required. The veterinary provider via the Provider Application can start and/or stop the blood pressure operation; however, this is not required. As can be appreciated, the user can start and/or stop the blood pressure operation; however, this is not required. The veterinary provider and/or user can request assistance by the veterinary assistant related to the use of the blood pressure cuff if so required.

The one or more grooming tools (e.g., brush, comb, scissors, nail clippers, electric shaving device, etc.), when used, are used to clean and/or groom the animal and/or to locate fleas, lice, etc. on the animal. The information that is obtained using the one or more grooming tools can be transmitted and displayed on the User's Screen and/or Provider's Screen in the veterinary kiosk and/or on the screen being used by the veterinary provider, and/or viewed by one or more cameras in the veterinary kiosk which can then be displayed on the User's Screen and/or Provider's Screen in the veterinary kiosk and/or on the screen being used by the veterinary provider; however, this is not required. On the interior of the veterinary kiosk, the one or more grooming tools can be contained in one of the medical device cabinets in the veterinary kiosk; however, this is not required. Alternatively, the one or more grooming tools can be kept in other locations in the veterinary kiosk and/or with the veterinary attendant; however, this is not required. In one non-limiting arrangement, when the veterinary provider via the Provider Application selects the grooming device icon on the provider's screen, the cabinet door in the veterinary kiosk for the one or more grooming devices opens or drops down to enable the user in the veterinary kiosk to access the one or more grooming devices; however, this is not required. As can be appreciated, if the one or more grooming devices are not located in a medical cabinet, the user can obtain the one or more grooming devices from the location in which the grooming device currently exists in the veterinary kiosk or the medical assistant can provide the one or more grooming devices to the user if the veterinary attendant is retaining the one or more grooming devices. The veterinary provider can provide instructions to the user on how to use the one or more grooming devices and/or instructions for use of the one or more grooming devices can be provided on the User Screen and/or Provider Screen in the veterinary kiosk; however, this is not required. The veterinary provider via the Provider Application can capture images from the use of the one or more grooming devices on the animal via the one or more cameras in the veterinary kiosk for placement in the animal's file; however, this is not required. The veterinary provider and/or user can request assistance by the medical assistant related to the use of the one or more grooming devices if so required.

The scale, when used, is used to obtain the weight of the animal. The scale can be designed to transmit the weight; however, this is not required. The weight that is transmitted by the scale can be displayed on the User's Screen and/or Provider's Screen in the veterinary kiosk and/or on the screen being used by the veterinary provider; however, this is not required. The transmission of the signal from the scale can be by various means (e.g., hardwire, USB™, Bluetooth™, wireless, etc.). On the interior of the veterinary kiosk, the scale can be located on the floor of the veterinary kiosk, and/or on an animal examination table or at some other location; however, this is not required. The animal's weight can be collected during the vitals capture process which is prior to the consultation with the veterinary provider; however, this is not required. If the veterinary provider wants the animal's weight to be retaken or if the animal's weight has not already been taken, the scale can be activated or reactivated by the veterinary provider via the Provider Application by the veterinary provider selecting the scale icon on the provider's screen; however, the scale can be activated by other or additional arrangements. As can be appreciated, the scale can always be active and/or the user and/or medical assistant can activate the scale, thus not requiring activation by the veterinary provider; however, this is not required. In one non-limiting arrangement, when the veterinary provider via the Provider Application selects the scale icon on the provider's screen, the scale in the veterinary kiosk is activated to enable the user in the veterinary kiosk to obtain the weight of the animal; however, this is not required. The veterinary provider can provide instructions to the user on how to use the scale and/or instructions for use of the scale can be provided on the User Screen and/or Provider Screen in the veterinary kiosk; however, this is not required. When the scale is activated, a video image can be designed to appear on the Provider Application (e.g., veterinary provider's screen) and/or the Provider Screen and/or User Screen that is located in the interior of the veterinary kiosk. If a video image option is available for display on the Provider Screen and/or User Screen that is located in the interior of the veterinary kiosk, the veterinary provider via the Provider Application can turn off such video image on the Provider Screen and/or User Screen; however, this is not required. The veterinary provider via the Provider Application can capture images and/or data generated by the scale and/or video camera in the medial kiosk for placement in the animal file; however, this is not required. The veterinary provider via the Provider Application can optionally annotate an image once captured (e.g., use the paint brush and font icons to modify image, etc.) and/or show the captured image to the user; however, this is not required. The veterinary provider and/or user can request assistance by the medical assistant if so required. The scale can be positioned in any location in the veterinary kiosk (e.g., floor, bench, chair, animal examination table, etc.). In one non-limiting embodiment, the scale can be integrated into the veterinary kiosk in such a way that it is at least partially incorporated in/on the floor of the veterinary kiosk. In one non-limiting design, the scale is positioned flush with the floor so that it poses no safety challenges for the animal or user in the veterinary kiosk; however, this is not required. As can be appreciated, the size, shape, and type of scale are non-limiting. The scale in the floor of the kiosk can also optionally be used as a designated standing location of an animal so that a height of the animal can be obtained by use of one or more cameras and/or other medical devices in the veterinary kiosk; however, this is not required.

In another and/or alternative non-limiting aspect of the invention, the novel method and apparatus for providing veterinary services, diagnoses, health, and/or wellness advice to individuals can include a scheduling application that 1) enables a veterinary provider to input the day and time the veterinary provider is available to conduct a visit with a user in a veterinary kiosk, 2) obtains or collects information on appointments that have been made by one or more users, at one or more veterinary kiosks, and 3) assigns a veterinary provider to a particular appointment that has been made at a particular veterinary kiosk. The scheduling application can be designed to enable a user to select a particular veterinary provider, gender of a veterinary provider, specialty of a veterinary provider, a veterinary provider that can speak a certain language, etc.; however, this is not required. The scheduling application can be designed to allow a veterinary provider to refuse an appointment with a particular user; however, this is not required. If the veterinary provider refuses an appointment, the scheduling application can be designed to attempt to schedule a different appoint for the newly available time slot of the veterinary provider, or can block off such time and not reschedule a new appointment for such time period; however, this is not required. The scheduling application can be designed to select a veterinary provider for a particular appointment based on a set algorithm (e.g., available veterinary provider that has the largest time since last appointment, etc.) and/or by a random process. The scheduling application can be designed to attempt to select a new veterinary provider for a particular appointment if the originally selected veterinary provider is unable and/or unwilling to conduct a visit with a user in the veterinary kiosk; however, this is not required.

In still another and/or alternative non-limiting aspect of the invention, the novel method and apparatus for providing veterinary services, diagnoses, health, and/or wellness advice to individuals can include a medication adherence application; however, this is not required. The medication adherence application can be designed to reduce medication errors. The medication adherence application can include a reminder for user to have the animal take its medication and then optionally the system can automatically log when the animal takes its medication; however, this is not required. The medication adherence application can also include the ability to track a user's compliance to give the animal medication on time and/or provide automatic progress reports; however, this is not required. The medication adherence application can also include the ability to refer the user to a pharmacist to answer any questions and/or for additional consultation; however, this is not required. Each user utilizing the veterinary kiosk can be automatically enrolled in the e-script network, which network sends their prescriptions to the pharmacy of their choice; however, this is not required. The medication adherence application can be used to assist in improving the animal's outcome and/or the satisfaction of the user. The medication adherence application of the present invention can be designed to be used on a screen in the veterinary kiosk, and/or on a computer screen and/or mobile device; however, this is not required. The medication adherence application of the present invention can be designed to generate a screen that includes one or more main buttons (e.g., 1) Speak to a _____ (e.g., Walgreens™, CVS™, Wal-Mart™, Pets Mart™, etc.) Pharmacist now, 2) Change the medications alerts, 3) Learn about controlling _____ (e.g., fleas, ticks, cholesterol, high blood pressure, diabetes, fur balls, urinating on the floor, etc.), 4) Check orders status, 5) Refill Prescriptions, etc., 6) Transfer prescriptions to _____ (e.g., Walgreens™, CVS™, Wal-Mart™, Pets Mart™, etc.), 7) Recommended dosage, 8) Period for taking medications, 9) Frequency for taking medications, 10) Information about medications, 11) Generic brands available for medications, 12) Request appointment to speak with a veterinary provider, 13) Entry of compliance information regarding medication usage by the animal, etc.); however, this is not required. The screen can include additional buttons (e.g., help button, Finish button, etc.); however, this is not required. The screen can include advertising information; however, this is not required. The selection of one or more of the buttons can result in additional screens appearing based on the selected button; however, this is not required. If a user needs further guidance from the pharmacist regarding the prescribed medication, the user can select the first category button to request such information; however, this is not required. The user can be provided a number to call and/or allow the user to send an email, make a phone call, etc. regarding the question. The user can be provided the option to set a new appointment to meet with a veterinary provider regarding the medication; however, this is not required. The user can be provided the option to change the medication alerts; however, this is not required. Such change can be requested by telephone, email, text, phone, etc. The frequency and/or type of alert and/or the manner in which the alert is sent to the user (e.g., email, twitter, phone message, text, etc.) may also be modified by the user; however, this is not required. The user may be provided the option to obtain information about certain medical conditions (e.g., cholesterol, blood pressure, grooming, rabies, heat worms, etc.); however, this is not required. The user may be provided the option to obtain the order status, shipment status, etc. for a particular medication; however, this is not required. If allowable by current medication guidelines and/or medical plans, the user may request to fill their prescriptions directly through the medication adherence application; however, this is not required. The user may be provided the option to change their preferred prescription location; however, this is not required. The user may be provided the option to enter information as to whether the prescribed medications are being timely taken and in the proper amounts; however, this is not required. Periodic reports regarding medication compliance can be generated and provided to the user via phone, email, text, twitter, etc.; however, this is not required. The medication adherence application of the present invention can be used to allow the user to more easily obtain and understand the correct use of the animal's prescriptions. In summary, the medication adherence software application allows a user to 1) speak to a pharmacist, 2) change the animal's medications alerts, 3) learn about certain types of medical conditions, 4) check medication orders status, 5) check medication delivery status, 6) refill a prescriptions, 7) transfer prescriptions to another location, 8) obtain information about recommended medication dosages, 9) obtain information about recommended times to take medications, 10) obtain information about recommended frequency for taking medications, 11) obtain information about medications, 12) obtain information about generic brands available for medications, 13) request an appointment to speak with a veterinary provider, 14) enter information regarding compliance information regarding medication usage by animal, and/or 15) receive compliance reports for user regarding medication usage.

In yet another and/or alternative non-limiting aspect of the invention, the novel method and apparatus for providing veterinary services, diagnoses, health, and/or wellness advice to individuals can include an expandable mounting system for medical devices; however, this is not required. In one non-limiting embodiment of the invention, the veterinary kiosk includes one or more equipment chambers that can be positioned on or near the front interior wall of the veterinary kiosk; however, it can be appreciated that one or more equipment chambers can be positioned in other or additional regions of the veterinary kiosk. The equipment chambers are used to store one or more medical devices (e.g., stethoscope, an otoscope, a thermometer, a dermascope, a stadiometer/height gauge, a blood pressure monitor, and/or one or more grooming tools, etc.). The one or more equipment chambers can also or alternatively be used to include other types of materials (e.g., tissue, Band-Aid™, gauze, cotton ball, disinfecting wipe, cortisone cream, antibiotic cream/ointment, alcohol wipe, cotton swab, fabric wrap, etc.). The one or more equipment chambers generally include a door to limit access to the one or more equipment chambers; however, this is not required. The door, when used on one or more of the equipment chambers, can be manually openable/closeable, and/or the doors can be controllably opened/closed remotely by the veterinary provider and/or veterinary attendant. Generally, one or more of the doors are controllably opened and/or unlocked by the veterinary provider during the examination of the animal in the veterinary kiosk; however, this is not required. After the animal and the user have left the veterinary kiosk, the veterinary attendant can enter the veterinary kiosk, clean the medical equipment that was handled or used by the prior user, and/or dispose of and/or replace items that were used and/or handled by the prior user; however, this is not required. Thereafter, the veterinary attendant can restock, replace, and/or reposition the medical equipment and/or non-medical equipment in the equipment chambers and close the equipment chamber doors prior to the next user entering the veterinary kiosk; however, this is not required.

One or more types of medical equipment can be designed to transmit information by wire and/or wirelessly to electronic components in the veterinary kiosk and/or to the remotely located veterinary provider; however, this is not required. In one non-limiting arrangement, the veterinary kiosk can include one or more equipment chambers having doors on each side of the desk top of the veterinary kiosk. As also can be appreciated, some or all of the equipment chambers can be absent doors. The door on one or more of the equipment chambers can be designed to be unlocked and/or opened remotely by the veterinary provider and/or veterinary attendant; however, this is not required. The doors can be designed to automatically lock when the doors are closed by the veterinary attendant and/or veterinary provider after the user has left the veterinary kiosk; however, this is not required.

One or more or each of the equipment chambers can be designed to include a different piece of medical equipment; however, this is not required. The one or more equipment chambers can also or alternatively be used to include other or additional types of material (e.g., tissue, gauze, disinfecting wipe, cotton ball, tongue depressor, tweezers, cortisone cream, urine sample container, etc.); however, this is not required. The one or more equipment chambers generally include a door to limit access to the one or more equipment chambers; however, this is not required. The door, when used, can be manually openable/closeable, and/or the doors can be controllably open/closed remotely by the veterinary provider or veterinary attendant; however, this is not required.

The expandable mounting system for medical devices can be made of high-strength plastic or any other sufficiently rigid and strong material such as metal, wood, composite materials, and the like. The configuration and/or size of each the equipment chambers can be the same or different. The size and/or shape of the each of the equipment chambers are non-limiting. The size and/or shape of two or more of the equipment chambers can be the same or different. The one or more doors on the expandable mounting system can be manually opened and/or closed and/or remotely opened and/or closed by a veterinary provider and/or veterinary attendant. The one or more medical devices in the one or more chambers or bays can be activated/deactivated remotely by software and/or manually activated/deactivated. The one or more medical devices in the one or more chambers or bays can be connected to a connector in the chambers or bays so as to supply power to the medical device and/or to electronically transmit information between the medical device and a computer, network, storage device, etc.; however, this is not required. The expandable mounting system can include one or more visual indicators (e.g., light, etc.) to indicate to a user which chamber is to be used and/or is active. A veterinary attendant and/or veterinary provider can be used to assist the user in the operation of one or more medical devices; however, this is not required.

In still yet another and/or alternative non-limiting aspect of the invention, the novel method and apparatus for providing veterinary services, diagnoses, health, and/or wellness advice to individuals can include digital signage on the exterior of the veterinary kiosk; however, this is not required. The digital signage, when used, can be displayed through one or more monitors or display screens on the exterior and/or interior of the veterinary kiosk to enable a user/potential user to see one or more of the monitors or display screens. One non-limiting aspect of this invention is that the one or more monitors or display screens can be used to display advertisements that may be arranged by the originating site; however, this is not required. Another non-limiting aspect of this invention is that one or more of the monitors or display screens can be used to display the current wait time for the veterinary kiosk and/or the list of scheduled appointments; however, this is not required. The digital signage application can allow various companies to advertise via the veterinary kiosk, including the business where it is located; however, this is not required. The digital signage application can be tailored to display information for specific users; however, this is not required. The digital signage application can include the ability to display a scrolling message at the bottom of the screen, based upon the business's preference; however, this is not required. The one or more display screens and/or monitors can be used to provide various types of information (e.g., registration information, information input by the user of the veterinary kiosk, advertising information, information about the veterinary kiosk, information about wait time for a veterinary kiosk, information as to the order of users waiting to use the veterinary kiosk, information about whether a veterinary kiosk is available or in use, cable TV, satellite TV, local broadcast TV, infomercial, medical programs, DVD materials, Blu-ray materials, etc.). The users waiting to enter the veterinary kiosk can be displayed on the one or more screens; however, this is not required. The user can see the wait time for their appointment and/or their position in the appointment queue when such information is displayed on the one or more video screens; however, this is not required. Any message necessary for the user to see can also be displayed upon the screen in the interior of the veterinary kiosk; however, this is not required (e.g., "Welcome (User Name)", "Your Veterinary provider (Provider Name) Will Begin Your Visit Once You Have First Captured Some Basic Vitals On Your Pet", etc.). The one or more interior screens are primarily utilized for video conferencing between the user and the veterinary provider, user data input, and user instructions, but it can also be used to display advertisements and/or other information during periods where the veterinary kiosk has no appointment queued; however, this is not required. The digital signage application can allow businesses to display advertisements and/or current promotions in a way that will attract the consumer's attention; however, this is not required. The ability to tailor the signage to individual users and/or population groups makes it very adaptable; however, this is not required. The information on the display can be any language. The information on the display can include subtitles, etc.; however, this is not required.

In another and/or alternative non-limiting aspect of the invention, the novel method and apparatus for providing veterinary services, diagnoses, health, and/or wellness advice to individuals can include an exterior check-in registration station via an integrated touch screen monitor; however, this is not required. The novel method of the present invention can include the use of a veterinary kiosk to enable the user to conveniently communicate with the veterinary provider. In one non-limiting embodiment, the veterinary kiosk has an exterior check-in registration station. The check-in registration station can include a key pad and/or key board for identification and/or data entry, a touch screen for identification and/or data entry, microphone and/ or voice recognition software for identification and/or data entry, fingerprint scanner for identification and/or data entry, and/or retina scanner for identification and/or entry; however, this is not required. As can be appreciated, other or additional devices can be included on the veterinary kiosk for identification and/or data entry. The veterinary kiosk having an exterior check-in registration station can be used by the user to enter/convey basic information about the user. Such information includes, but is not limited to, a) user name, b) user address, c) user contact information, d) animal's name, e) type of animal, f) breed of animal, g) age of animal, h) sex of animal, i) animal's height, j) animal's weight, k) animal's medical history, l) current medicines used by animal, m) reason(s) for visit by animal, n) animal's symptoms, o) user insurance information, p) user payment information, q) consent forms, and/or r) animal's current veterinarian. As can be appreciated, other or additional information can be inputted/conveyed by the user.

The medial kiosk can be designed to provide information to the user prior to and/or during the inputting/conveying of information by the user to the veterinary kiosk. In one non-limiting embodiment of the invention, the veterinary kiosk can include audio and/or visual instructions and/or displays used to provide a) information about the veterinary kiosk, b) how to use the veterinary kiosk, c) how to properly input/convey information to the veterinary kiosk, d) provide instructions and/or interactions with the user during the inputting/conveying of information by the user to the veterinary kiosk, e) the wait time for the user's use of the veterinary kiosk, f) a list of users waiting to use the veterinary kiosk, and/or g) information regarding whether the veterinary kiosk is in use or is available.

In another and/or alternative non-limiting embodiment of the invention, the veterinary kiosk can include light and/or sound indicators to provide information regarding whether the veterinary kiosk is in use or is available; however, this is not required. In still another and/or alternative non-limiting embodiment of the invention, the veterinary kiosk can include a notification system to a user that the veterinary kiosk is available or will soon be available; however, this is not required. Such notification can be sent via email, phone, pager, internet, etc. Such notification system can be useful when the veterinary kiosk is not currently available to the user. The user can input the information into the veterinary kiosk and then go home, run other errands, etc., and then be later notified when the veterinary kiosk is available or will soon be available. The veterinary kiosk and/or notification system can also be used to inform the user when and/or where other veterinary kiosks are available; however, this is not required. This service, when available, can be used to inform the user that a nearby veterinary kiosk has a shorter wait period or is currently available, thus providing the user with the option of traveling to another available veterinary kiosk instead of waiting for the current veterinary kiosk to become available; however, this is not required. This service, when available, can also be used to inform the user when a prescription is ready for pickup and/or for conveying prescription information to the user; however, this is not required. This service, when available, can also be used to inform the user when a follow-up visit is due for the animal and/or scheduled; however, this is not required. As can be appreciated, the notification system can be used for other or additional services. The veterinary kiosk can include an exterior registration station for check-in via a touch-screen monitor (e.g., monitor, etc.). The touch-screen monitor can be mounted at a height and angle that meets ADA compliance and is easily accessible to individuals in wheel chairs; however, this is not required. The touch-screen monitor can include a built in privacy filter for any type of regulatory and/or privacy compliance; however, this is not required. In one non-limiting embodiment, the front panel of the veterinary kiosk includes a registration station. The registration station can include a touch screen, a display screen, and an optional frame to which such components can be mounted; however, this is not required. The shape of the frame, when used, is non-limiting. The frame, when used, can be designed to be easily removed from the front panel to enable the servicing, repair, replacement, etc. of one or more components of the registration station; however, this is not required. As can be appreciated, the registration station can also or alternatively include other or optional features (e.g., additional display screen, additional touch screen, lights, buttons, switches, camera, speakers, microphone, keyboard, scanner, receiver, transmitter, credit card/debit card or other some other card reader, smart phone or other smart device reader/scanner, finger and/or eye scanner, shelf, printer, storage cavity, service access door, motion sensor, sound sensor, temperature sensor, logos, etc.); however, this is not required. The touch screen, when used, is generally used to allow a user to enter information about the user (e.g., age, contact information, animal name, type of animal, breed of animal, age of animal, sex of animal, payment information, medical history of animal, medical issue of animal, etc.); however, this is not required. The touch screen can be substituted for a keyboard; however, this not required. The frame can be designed to mount the touch screen at some angle (e.g., 10-80°) relative to the front plane of the front panel; however, this is not required. The frame optionally includes one or more side sections that can include one or more other or optional features of the registration station; however, this is not required. As can be appreciated, one or more other or optional features of the registration station can also or alternatively be located on other regions of the registration station. The touch screen can display various types of information (e.g., electronic keyboard, instructions on how to register, questions that are displayed during registration, instructions during registration, information displayed to user during registration, various templates, various menus, various lists of information, etc.); however, this is not required. As can be appreciated, the veterinary kiosk can be designed to accept voice commands during the registration process; however, this is not required. The display screen can be used to provide various types of information (e.g., registration information, information input by the user, advertising information, information about the veterinary kiosk, information about wait time for a veterinary kiosk, information as to the order of users waiting to use the veterinary kiosk, information about whether a veterinary kiosk is available or in use, cable TV, satellite TV, local broadcast TV, infomercial, medical programs, DVD materials, Blu-ray materials, etc.). Another display screen can be positioned above the screen used at the registration station and/or at some other location on the exterior of the veterinary kiosk; however, this is not required. This other display screen can be used to display various types of information (e.g., advertising information, information about the veterinary kiosk, information about wait time for a veterinary kiosk, information as to the order of users waiting to use the veterinary kiosk, information about whether a veterinary kiosk is available or in use, cable TV, satellite TV, local broadcast TV, infomercial, medical programs, DVD materials, Blu-ray materials, etc.); however, this is not required. In one non-limiting arrangement, the screen used at the registration station and the one or more other displays can be design to display different types of information (e.g., screen used at the registration station displays information related to the registration process and the one or more other displays are used to display one or more types of information that are different from the information displayed on the screen used at the registration station, etc.); however, this is not required. The size of the screen used at the registration station and the one or more other displays can be the same or different. In one non-limiting arrangement, a user can be allowed to enter payment information at the registration station (e.g., swipes a credit or debit card, manually enters credit or debit card information, transfer payment information via a smart phone or other smart device, etc.); however, it can be appreciated that payment information can also or alternatively be entered inside the veterinary kiosk, at the optional attendant station, wirelessly or over a network via a smart phone or other device or by a computer connected to a network, etc. If a veterinary attendant is available, the veterinary attendant can assist a user during the registration process; however, this is not required. Generally, the veterinary kiosk includes a single registration station; however, this is not required. As can be appreciated, the registration station can alternatively be located inside the veterinary kiosk, at the attendant station, on other panels or sidewalls of the veterinary kiosk, or located remotely from the veterinary kiosk (e.g., central registration center for use with multiple veterinary kiosks, etc.). In one non-limiting arrangement, the exterior check-in registration station can be designed to be easily removed from the front panel of the veterinary kiosk and/or be easily accessed from the interior of the veterinary kiosk to enable servicing, repair, replacement, etc. of one or more components of the registration station; however, this is not required. The check-in system in accordance with the present invention offers a new way for organizations to meet rising consumer expectations for convenience and at the same time improve accuracy and usability of information systems; however, this is not required. The check-in system in accordance with the present invention can result in shorter waiting times for check-in, as well as efficiency gains from increased throughput and fewer errors in keeping user demographic data and/or animal date up to data; however, this is not required. The check-in system in accordance with the present invention can result in the reduction of risk of the animal and/or user misidentification and clerical errors at data entry; however, this is not required. The check-in system in accordance with the present invention can improve accuracy in language access for those not fluent in English by offering multiple language options during the check-in process; however, this is not required.

In still another and/or alternative non-limiting aspect of the invention, the novel method and apparatus for providing veterinary services, diagnoses, health, and/or wellness advice to individuals can include a sanitizing system (e.g., UV system, mist system, etc.) that can be automatically activated and/or be activated by the veterinary attendant and/or veterinary provider prior to and/or after a user has used the veterinary kiosk; however, this is not required. The veterinary kiosk can include a cleaning system designed to clean the interior of the veterinary kiosk and/or kill/neutralize some of or all germs and/or other micro-organisms in the veterinary kiosk; however, this is not required. One non-limiting cleaning system that can be used is an ultraviolet sanitizing system. As can also be appreciated, a mist sanitizer can also or alternatively be used to fully or partially clean/sanitize one or more portions of the veterinary kiosk. As can be appreciated, other or additional cleaning systems can be used. In another and/or alternative non-limiting aspect of the invention, the veterinary kiosk can be made of one or more materials that resist growth of bacteria, viruses and/or other micro-organisms; however, this is not required. In one non-limiting embodiment, the floor, walls and ceiling of the veterinary kiosk include or are fully made of materials that resist or prevent the growth of bacteria, viruses and/or other micro-organisms; however, this is not required. In one non-limiting arrangement, the veterinary kiosk includes an ultraviolet light sanitization system which can be used in the veterinary kiosk and which can be activated through software from a remote location and/or by a kiosk attendant; however, this is not required. The ultraviolet light sanitization system can be activated twice daily to ensure the sanitary environment is maintained; however, it can be appreciated that the ultraviolet light sanitization system can be activated a greater or lesser number of times per day. The location of the ultraviolet light sanitization system, when used, is non-limiting. In one non-limiting arrangement, the ultraviolet light sanitization system can be located in the roof or ceiling of the veterinary kiosk; however, this is not required. For example, the ultraviolet light sanitization system can be connected or positioned adjacent to the ceiling panel and rear panels; however, this is not required. The ultraviolet light sanitization system can be located in the rear of the veterinary kiosk where it will be out of the way of the user utilizing the veterinary kiosk; however, this is not required. The ultraviolet light sanitizing system generally includes one or more ultraviolet lights that are designed to kill some or all of the germs and/or other micro-organisms in the veterinary kiosk. The ultraviolet sanitizing system can optionally include one or more vents that allow air to flow into and/or out of the ultraviolet sanitizing system to facilitate in the cooling of the ultraviolet sanitizing system; however, this is not required. The sanitization system can be built with high-strength plastics and/or any other sufficiently rigid and strong material such as metal and constructed in a way preventing it from being tampered with by users or anyone other than the attendant or other authorized personnel; however, this is not required. Such an arrangement, when used, can facilitate in ensuring that it is not activated incorrectly or at an inopportune time; however, this is not required. The shape, size and/or configuration of the built in sanitization system are non-limiting. The one or more veterinary attendants, when used, can also or alternatively clean and/or sanitize various regions of the veterinary kiosk prior to and/or after being used by a user and/or set up the veterinary kiosk for a new user; however, this is not required. For example, prior to and/or after one or more users have entered the veterinary kiosk, the one or more attendants can clean/sanitize one or more exterior surfaces and/or regions of the veterinary kiosk (e.g., veterinary kiosk door, veterinary kiosk check-in terminal, veterinary kiosk desk top, veterinary kiosk exterior walls, veterinary kiosk touch screen, veterinary kiosk monitors, seating/tables in waiting area near veterinary kiosk, etc.); however, this is not required. In an another and/or additional example, prior to and/or after one or more users have entered the veterinary kiosk, the one or more veterinary attendants can clean/sanitize one or more interior surfaces of the veterinary kiosk (e.g., veterinary kiosk door, veterinary kiosk floor, veterinary kiosk bench, veterinary kiosk chair, veterinary kiosk user terminal, veterinary kiosk interior desk top, veterinary kiosk interior walls, veterinary kiosk touch screen, veterinary kiosk monitors, veterinary kiosk instrument doors, medical devices/instruments used by and/or touched by user when in the veterinary kiosk, examination table, examination scale, any other surface in the interior of the veterinary kiosk, etc.); however, this is not required. In still another and/or additional example, prior to and/or after one or more users have entered the veterinary kiosk, the one or more veterinary attendants can set up the veterinary kiosk for a user (e.g., clean/sanitize interior surfaces of veterinary kiosk; clean/sanitize medical devices/instruments used and/ or touched by a prior user; reposition medical devices/ instruments into device storage areas; replace disposable components on medical devices/instruments; fix, repair and/ or replace fans, UV bulbs, UV devices, etc. in the interior and/or exterior of the veterinary kiosk; refill cleaning and/or sanitizing fluid; etc.); however, this is not required. In still yet another and/or alternative non-limiting aspect of the invention, the veterinary kiosk can include a sanitizing system (e.g., UV system, mist system, etc.) that can be automatically activated and/or activated by the veterinary attendant prior to and/or after a user has used the veterinary kiosk; however, this is not required. As can also be appreciated, a mist sanitizer can also or alternatively be used to fully or partially clean/sanitize one or more portions of the veterinary kiosk. Generally, the germs and/or other microorganisms in the veterinary kiosk are treated when the interior of the veterinary kiosk does not include a user. The sanitizing system can optionally include one or more standard lights that can be used to provide illumination in the veterinary kiosk; however, this is not required. The sanitizing system can optionally include a cooling fan for the one or more components in the sanitation system; however, this is not required. The sanitizing system can optionally include both a UV and a mist sanitizing system; however, this is not required. The sanitizing system can house one or more cameras, speakers, sensors (e.g., temperature sensor, motion sensor, sound sensor, etc.), etc. for use in the veterinary kiosk; however, this is not required. The sanitizing system can include a shroud that includes vent/light/mist openings to house the components of the sanitizing system; however, this is not required. The shape, size and configuration of the shroud, when used, are non-limiting. When a mist sanitizing system is additionally or alternatively used, one or more mist nozzles can be located in one or more regions of the veterinary kiosk so as to direct the sanitizing mist to desired locations in the veterinary kiosk; however, this is not required. The doors to the veterinary kiosk can be closed and/or locked to prevent an animal and/or individual from entering the veterinary kiosk during a sanitizing process; however, this is not required.

In yet another and/or alternative non-limiting aspect of the invention, the novel method and apparatus for providing veterinary services, diagnoses, health, and/or wellness advice to individuals can include a veterinary kiosk that enables a service operator to easily access the various components of the veterinary kiosk for purposes of service, repair, maintenance, upgrade, replacement, etc. In order to offer the comprehensive services the veterinary kiosk is capable of, there are multiple components that must be functioning at all times. The various devices that may need service include, but are not limited to, the display screens, the network connection, various other electronics and wiring, fans, lights, electronic switches, backup power supplies, computers, electronic storage devices, doors on the medical equipment compartments, medical devices, medical device retraction systems, etc. The ability to easily and conveniently access and/or perform maintenance on these components is advantageous to providing the veterinary kiosk services via the veterinary kiosk; however, this is not required. To more easily facilitate the service of these components, the veterinary kiosk can be designed with a moveable front panel; however, this is not required. The front panel can be built on casters, wheel, rail system, etc. to allow the front panel to be easily moved; however this is not required. The front panel can be equipped with a tamperproof lock to prevent unauthorized personnel from accessing the components located behind the front panel; however, this is not required. A portion or the entire front panel can be designed to move in order to ensure that, when there is a problem with one or more components used in the veterinary kiosk, the repair of such components does not require the disassembly of the entire or a substantial portion of the medial kiosk; however, this is not required. The components of the veterinary kiosk that are generally difficult or inaccessible when the veterinary kiosk is fully assemble are 1) the components that form the exterior check-in station, 2) the interior displays or monitors, 3) the interior speakers, 4) the interior cameras, 5) the interior sound jack, 6) the doors on the medical compartments, 7) the interior microphone, 8) the electronics located behind the exterior check-in station, 9) the electronics located behind the interior AV system, and/or 10) the computer and other electronics used for network communication, control and/or storage; however, this is not required. As can be appreciated, there may be other or additional components of the veterinary kiosk that are generally difficult or inaccessible when the veterinary kiosk is fully assembled. Access to one or more of these components can be more easily accessed by the movement of the interior front panel of the veterinary kiosk; however, this is not required.

In still yet another and/or alternative non-limiting aspect of the invention, the novel method and apparatus for providing veterinary services, diagnoses, health, and/or wellness advice to individuals can include a method and a veterinary kiosk that enables the veterinary provider to generate electronic prescriptions and/or for the user to conveniently select and/or order prescription drugs; however, this is not required. In one non-limiting embodiment, this novel method and apparatus will allow user to 1) choose between name brand and generic drugs, 2) choose the supply quantity for the prescription (i.e., 30 day supply, 60 day supply, 90 day supply, etc.), 3) choose between picking the prescription up at the pharmacy and/or pet store of their choice or mail delivery of the prescription, 4) enter medical insurance for partial or full payment of the prescription, 5) enter a credit or debit card information to pay for the prescription, 6) enter information for mail delivery of the prescription, 8) enter information to provide automatic reminders to user regarding refilled and/or follow-up medical visits of the animal, 9) enter information to enable a user to be notified when a prescription has been mailed and/or is ready to be picked-up at the pharmacy (this is not required), 10) obtain a print out and/or electronic version of the prescription written by the veterinary provider, and/or 11) receive information about the issued prescription (e.g., prescribed use, side effects, etc.) in printout and/or electronic form; however, this is not required. Another non-limiting aspect of this method and apparatus will allow the user to select the pharmacy, pet store, etc. where he/she would like to pick-up the prescription; however, this is not required. In one non-limiting embodiment of the invention, the veterinary provider can generate an electronic prescription for a user. The prescription can include both the generic and name brand drugs along with the user copay amount for each; however, this is not required. The electronic prescription can provide additional information (e.g., potential savings for selecting certain medications, the dosage amount, the medication dosage, quantity or strength, name of veterinary provider, help information, etc.), advertising information, etc.; however, this is not required. Once the particular medication brand is selected by the user, another screen can optionally appear; however, this is not required. For example, the second screen can illustrate the brand of medication selected by the user and/or also provide quantity supply options for the medication, etc.; however, this is not required. The second screen can optionally illustrated additional information such as, but not limited to, the copay amount for the selected medication brand and quantity, the monthly, yearly, etc. savings for selecting a particular medication brand and/or quantity, help information, go back option, advertising information, etc.; however, this is not required. The second or a third screen can optionally provide an order confirmation along with the associated savings; however, this is not required. The second or third screen can optionally illustrate additional information such as, but not limited to, the monthly, yearly, etc. savings for selecting a particular medication brand and/or quantity, help information, advertising information, etc. As can be appreciated, other or additional screens can be displayed to the user. This aspect of the invention has the advantage of allowing the user to view and/or select brand or generic drugs thereby allowing the user to decide which drug option is best for the animal and/or user budget; however, this is not required. The veterinary kiosk and method for using the veterinary kiosk can thus include a point-of-purchase prescription workflow application allowing a veterinary provider to generate prescriptions and optionally allowing users to select and/or order prescription drugs; however, this is not required. The veterinary kiosk and method for using the veterinary kiosk can include a point-of-purchase prescription workflow application that allows a user to choose his/her drug brand and/or quantity; however, this is not required. The veterinary kiosk and method for using the veterinary kiosk can include a point-of-purchase prescription workflow application that allows a user to select the pharmacy, pet store, etc. from which to pick up the prescription; however, this is not required.

In another and/or alternative non-limiting aspect of the invention, the novel method and apparatus for providing veterinary services, diagnoses, health, and/or wellness advice to individuals can include headphone jacks. The one or more headphone jacks allow for a hearing impaired user to utilize headphones in order to better understand the veterinary provider's instructions; however, this is not required. The one or more headphone jacks can also be used to enable additional persons in the veterinary kiosk to listen in on the conversation between the veterinary provider and user; however, this is not required. The one or more headphone jacks can also be used to provide additional privacy between the veterinary provider and user; however, this is not required. The headphones may be available from the kiosk and/or the veterinary attendant; however, this is not required. The headphone jack can be placed at a height allowing any person to reach it if necessary; however, this is not required. The headphones generally will be sanitary either through disposable covers or through another form of sanitization; however, this is not required. The headphone jack can be a standard jack to enable a user to use his/her own headphones; however, this is not required. The veterinary kiosk can include a wireless system (e.g., Bluetooth™ technology, IR technology, RF technology, etc.) to transmit sound wirelessly to a user and/or other person located in the veterinary kiosk; however, this is not required. The kiosk can also be equipped with a wheelchair accessible ramp; however, this is not required. The veterinary kiosk can be designed to be fully ADA compliant; however, this is not required. A veterinary kiosk that includes one or more headphone jacks and/or a wheelchair accessible ramp can permit the veterinary kiosk to better serve the public at large; however, this is not required.

In still another and/or alternative non-limiting aspect of the invention, the novel method and apparatus for providing veterinary services, diagnoses, health, and/or wellness advice to individuals can include a veterinary kiosk that utilizes high definition video and/or high quality sound to create a conference link between a user located in the veterinary kiosk and a veterinary provider that is located remotely to the veterinary kiosk. In one non-limiting aspect of the invention, the veterinary kiosk includes the use of one or more high definition cameras, one or more high definition monitor(s) and/or high quality speaker(s) built into the veterinary kiosk; however, this is not required. The one or more cameras located within the veterinary kiosk can be on an adjustable sliding bar allowing camera positioning to create ideal eye contact; however, this is not required. The one or more cameras in the veterinary kiosk can be used to enable a veterinary provider to obtain information about the animal in the veterinary kiosk (e.g., animal height, animal sex, type of animal, breed of animal, animal body cuts, animal body infections, animal body rashes, animal hygiene, animal physical condition, etc.); however, this is not required. In one non-limiting arrangement, one or more monitors and/or display screens can be positioned on the front interior wall of the veterinary kiosk; however, this is not required. The one or more monitors are generally used to view the one or more veterinary providers when the user is located in the veterinary kiosk; however, this is not required. The shape, size, and thickness of the one or more monitors are non-limiting. One or more cameras can be positioned on the front interior wall, be embedded in the one or more monitor/display screens, and/or be located on a sliding bar allowing it to be positioned relative to the animal and/or user to create better eye contact with the user in the veterinary kiosk and/or view of the animal; however, this is not required. The one or more cameras enable pictures of the animal and/or user in the veterinary kiosk to be transmitted to a remotely located veterinary provider; however, this is not required. The remotely located veterinary provider typically has a camera at his/her location so that pictures of the veterinary provider can be transmitted to the one or more medical screens in the veterinary kiosk; however, this is not required. As can be appreciated, a projector can be used as a substitute for one or more monitors in the veterinary kiosk; however, this is not required. One or more speakers can be positioned on the front interior wall of the veterinary kiosk; however, this is not required. As can be appreciated, one or more speakers can be positioned on other or additional locations in the veterinary kiosk; however, this is not required. The speakers can be used to enable a user in the veterinary kiosk to listen to what the veterinary provider is saying; however, this is not required. One or more microphones are generally included in the veterinary kiosk to allow the user to communicate with the veterinary provider; however, this is not required.

In yet another and/or alternative non-limiting aspect of the invention, the novel method and apparatus for providing veterinary services, diagnoses, health, and/or wellness advice to individuals can include a veterinary kiosk that is modular kiosk that is able to be partially or fully broken down; however, this is not required. In one non-limiting embodiment of the invention, the modular veterinary kiosk can be partially or fully broken down so as to fit through a doorway (e.g., standard 36" by 80" doorway, etc.); however, this is not required. The modular design of the veterinary kiosk can enable the veterinary kiosk to be set up in various configurations to enable the veterinary kiosk to be used in various types of spaces; however, this is not required. The modular design of the veterinary kiosk can be designed to not only accommodate multiple configurations of the veterinary kiosk, but can also be designed to facilitate in enabling the veterinary kiosk to be moved into an existing facility and then allowing the assembly of the veterinary kiosk in such facility without having to modifying the entryway into or out of the facility; however, this is not required. The veterinary kiosk can be formed of any number of materials (e.g., plastic, foam, metal, wood, etc.). The modular configuration of the veterinary kiosk can be such that it can be easily assembled and/or disassembled so that the veterinary kiosk can be easily brought into a location and easily set up; however, this is not required. The veterinary kiosk can be designed to include a floor panel; however, this is not required. The floor panel, when used, is generally a one piece unit; however, the floor panel can be formed of multiple pieces. The floor panel, when used, can be formed of a durable material (e.g., plastic, metal, wood, composite material, man-made materials, etc.). The floor panel, when used, can be formed of a slightly compressible material to facilitate in the comfort of walking on the floor panel; however, this is not required. The floor panel can have an oval shape; however, other shapes can be used (e.g., circular, square, rectangular, polygonal, etc.). In one non-limiting design, the maximum length of the floor panel is generally 3-15 feet, typically 4-12 feet, more typically about 6-10 feet, and even more typically about 8-9 feet; however, other lengths can be used. In one non-limiting design, the maximum width of the floor panel is generally 3-10 feet, typically 4-8 feet, and more typically about 4-6 feet; however, other widths can be used. In one non-limiting design, the top surface area of the floor panel is generally 10-150 sq. ft., typically 15-80 sq. ft., and more typically about 50-60 sq. ft.; however, other surface areas of the floor panel can be used. The floor panel can be sized to enable a user in a wheelchair to enter the veterinary kiosk and turn and/or fully maneuver in the veterinary kiosk while sitting in the wheelchair; however, this is not required. In one non-limiting design, the thickness of the floor panel is generally about 0.1-5 inches, and typically about 0.25-3 inches; however, other thicknesses of the floor panel can be used. A ramp can be optionally used to facilitate entry and exiting of the veterinary kiosk; however, this is not required. The shape and size of the ramp are non-limiting. The ramp can be made of a similar material as the floor panel; however, this is not required. The ramp generally includes a sloped surface to facilitate in transitioning from a floor surface to the top surface of the floor panel; however, this is not required. The veterinary kiosk can optionally include one or more benches, stools and/or chairs. When a bench is included in the veterinary kiosk, the bench is generally positioned on the back interior wall of the veterinary kiosk; however, this is not required. The bench can be used to allow a parent, guardian, spouse, relative, friend, etc. to sit in the veterinary kiosk while the user is obtaining veterinary services in the veterinary kiosk. The bench can be designed to enable one or more persons to sit on the bench. The bench can optionally include a storage space under the seat of the bench that can be used to store supplies, equipment, etc. for the veterinary kiosk. A liftable seat section can be used to access the storage space; however, this is not required. When the bench includes a storage space, the bench can include a lock to limit access to the storage space; however, this is not required. As can be appreciated, the veterinary kiosk can include one or more chairs to enable one or more users to sit in the veterinary kiosk while receiving veterinary services in the veterinary kiosk; however, this is not required. The bench is generally about 10-25 inches high, and typically about 16-20 inches high; however, other heights can be used. In one non-limiting arrangement, the veterinary kiosk can include two front panels, two rear panels, one side wall, and one door system; however, this is not required. The front panels, rear panels, side wall, and door system are generally formed of a durable material (e.g., plastic, metal, wood, composite material, man-made materials, etc.). As can be appreciated, the veterinary kiosk can be designed to only include a single front panel and/or a single rear panel. As can also be appreciated, the veterinary kiosk can be designed to include more than two front panels and/or more than two rear panels. As can be appreciated, the veterinary kiosk can be designed to include more than one side wall and/or more than one door system. As can also be appreciated, a side wall can be substituted for another door system; however, this is not required. The general shape and size of the front and rear panels are the same; however, this is not required. The shape of the front and rear panels can be arcuate; however, this is not required. The radius of curvature the front and rear panels can be about 10-100 inches, typically 15-50 inches, and more typically about 20-35 inches; however, other radius of curvatures can be used. The front and rear panels can have an angle of curvature of about 90° or a quarter of a circle; however, it can be appreciated that one or both rear and/or front panels can have different angles of curvature. The general shape and size of the side wall and the door system are generally the same; however, this is not required. The side wall and door system can lie in a generally flat plane; however, this is not required. The front and rear panels and the side wall and door system can form a generally oval shape for the veterinary kiosk; however, this is not required. The two front panels and two rear panels can have the same or similar footprint; however, this is not required. The side wall and the door system can have the same or similar footprint; however, this is not required. The similarity in the shape and footprint of the wall components of the veterinary kiosk, when used, enables the veterinary kiosk to be assembled in a manner that is convenient for the facility that will include the veterinary kiosk. For example, if the door system needs to be positioned on the left side of the veterinary kiosk, instead of the right side, the similarly shaped side wall and door system enables the veterinary kiosk to be assembled in such a manner. Also, if the optional registration station of the medical system needs to be placed on the left side or right side or on the rear end of the veterinary kiosk instead of the front end, the similarly shaped front and rear panels can be easily exchanged to create such configuration for the veterinary kiosk. The modular veterinary kiosk not only accommodates multiple configurations of the veterinary kiosk, it also can facilitate in enabling the veterinary kiosk to be moved into an existing facility and then assembling the veterinary kiosk in such facility without having to modify the entryways into or out of the facility; however, this is not required. The thickness and height of the front panels, rear panels, side wall and door system are non-limiting. In one non-limiting embodiment, the maximum height of the front panels, rear panels, side wall and door system is about 5-12 ft., typically about 6-9 ft., and more typically about 7-8 ft.; however, other heights can be used. In one non-limiting embodiment, the thickness of the front panels, rear panels, side wall and door system is generally about 0.5-10 inches, typically about 1-5 inches, and more typically about 1-2 inches; however, other thicknesses can be used. The front panels, rear panels, side wall and door system can optionally include insulation, sound dampening material, etc.; however, this is not required. The front panels, rear panels, side wall and door system can be designed to be connected together in a variety of ways (e.g., bolted/screwed together, latched together, snap fitted together, press fitted together, etc.). Generally, the arrangement used to connect the front panels, rear panels, side wall and door system together is selected to enable easy connecting and/or disconnecting of the front panels, rear panels, side wall and door system from one another; however, this is not required. One or more of the front panels, rear panels, side wall and door system can include openings, windows, transparent/semi-transparent regions that allow for ventilation, illumination, and/or viewing; however, this is not required. Generally, front panels, rear panels, side wall and door system are mostly or fully formed of opaque or non-transparent materials so as to ensure the privacy of the animal and user in the veterinary kiosk; however, this is not required. The configuration of the door system is non-limiting. The door system can include a frame and two doors; however, it can be appreciated that the door system only includes a single door. Each door can include a handle or grasp cavity on one or both sides of the one or both doors. The one or more doors can be designed to open and close in a variety of ways (e.g., swing open and closed, slide open and closed on a top/bottom rail system, etc.). As can be appreciated, the one or more doors for the veterinary kiosk can also or alternatively be positioned on one or more of the front or rear panels; however, this is not required. In one non-limiting embodiment, the maximum height of the doors is generally about 5-9 ft., and typically about 6-7 ft.; however, other heights can be used. In one non-limiting embodiment, the maximum width of the entry provided by the one or more doors when fully open is generally about 15-60 inches, typically about 25-55 inches, and more typically about 30-50 inches; however, other widths can be used. The door opening is generally selected to enable a standard wheelchair to pass through the opening; however, this is not required. The veterinary kiosk can optionally include an exterior attendant station that is connected to and/or positioned near the veterinary kiosk. The exterior attendant station can be used by one or more veterinary attendants, veterinary providers, etc. A desk can be connected to and/or positioned next to an exterior wall of the veterinary kiosk; however, this is not required. The desk, when used, can be formed of one or more pieces. When the desk is designed to be connected to an exterior wall of the veterinary kiosk, such connection arrangement is not limited (e.g., screw, bolt, clamp, press fit, snap arrangement, etc.). The desk can include a desk top, one or more legs, one or more shelf regions, one or more drawers, etc.; however, this is not required. One or more chairs can be used to allow one or more veterinary attendants, veterinary providers, etc. to sit at the desk; however, this is not required. The desk, when used, can be positioned at or adjacent to one or both front panels; however, this is not required. The desk can be designed to include one or more drawers, shelves, doors, etc. One or more locks can be included on the desk; however, this is not required. The desk can be used to support a monitor, computer, power supply, power strip, printer, router, network switcher, key board, mouse, printer paper, medical supplies, sanitation supplies, refrigerator, freezer, scanner, credit card/debit card reader, data port, lights, desk supplies, etc. The freezer and/or refrigerator, when used, can contain immunizations, medications, urine samples, blood samples, stool samples, etc.

In still yet another and/or alternative non-limiting aspect of the invention, the novel method and apparatus for providing veterinary services, diagnoses, health, and/or wellness advice to individuals can include a veterinary kiosk that includes a ceiling panel. The ceiling panel can be formed of one or more pieces. The ceiling panel can be formed of a transparent or semi-transparent material to allow light to enter and illuminate the interior of the veterinary kiosk; however, this is not required.

In still yet another and/or alternative non-limiting aspect of the invention, the novel method and apparatus for providing veterinary services, diagnoses, health, and/or wellness advice to individuals can include a veterinary kiosk that is made of one or more materials that resist or prevent the growth of bacteria, viruses and/or other micro-organisms; however, this is not required. In one non-limiting embodiment, the floor, walls and ceiling of the veterinary kiosk include or are fully made of materials that resist or prevent the growth of bacteria, viruses and/or other micro-organisms; however, this is not required.

In still another and/or alternative non-limiting aspect of the invention, the novel method and apparatus for providing veterinary services, diagnoses, health, and/or wellness advice to individuals can include a veterinary kiosk that includes a payment center that enables a user to pay for veterinary services, prescriptions, medical equipment, medical accessories, etc. prior to and/or after the user uses the veterinary kiosk; however, this is not required. The payment center can be in any form (e.g., credit card reader, mobile phone scanner, transmitter/receiver device, electronic scanner, cash receiver, etc.). The payment center may include a touch pad, key board, scanner, receiver, transmitter, credit card/debit card or some other card reader, smart phone or other smart device reader/scanner, finger and/or eye scanner, monitor, chair, table, shelf, printer, instructions on how to use the payment center, etc. The payment center can be located on the exterior and/or interior of the veterinary kiosk. Generally, the user is required to register and pay for the veterinary services prior to obtaining veterinary services from the veterinary provider; however, this is not required. In one non-limiting arrangement, the veterinary kiosk includes a registration station on the exterior of the veterinary kiosk (e.g., exterior wall of the veterinary kiosk, on a table exterior to the veterinary kiosk, etc.); however, this is not required. As can be appreciated, a user can be allowed to wirelessly connect to the veterinary kiosk or to some other computer network so as to wirelessly register and/or enter payment information for use of the veterinary kiosk; however, this is not required. In such an arrangement, a user could register to use a veterinary kiosk, enter payment for use of the veterinary kiosk, set an appointment time for use of the veterinary kiosk, select a particular veterinary kiosk to use at some particular location, etc. at some location near or remote from the veterinary kiosk via a smart phone or other smart device, a tablet, a computer, etc.

In yet another and/or alternative non-limiting aspect of the invention, the novel method and apparatus for providing veterinary services, diagnoses, health, and/or wellness advice to individuals can include a veterinary kiosk that includes an interior cavity or room that provides privacy to the user when inputting and/or conveying data to the veterinary kiosk, and/or communicating with a veterinary provider via an audio and/or video link. The size, configuration and/or arrangement of the interior cavity or room are non-limiting. The interior cavity or room can include a) one or more speakers, b) one or more microphones, c) one or more video displays, d) one or more data input devices, e) one or more chairs and/or other types of seating areas, f) one or more tables, g) one or more doors, h) one or more shelves, i) one or more compartments used to contain medical supplies, medical instruments, etc., j) one or more light switches, k) one or more power outlets, l) a sterilization system, m) one or more headphone jacks, n) one or more lights, o) one or more table tops, p) one or more chair and/or benches, q) one or more doors, r) one or more windows, s) one or more walls, a floor and/or a ceiling, t) one or more vents, u) one or more power switches, v) one or more USB and/or data connection outlets, and/or w) one or more fans. As can be appreciated, the interior cavity or room can include other or additional items. The size and configuration of the interior cavity or room can be designed to enable wheelchair access and maneuvering inside the interior cavity or room; however, this is not required. For example, the interior cavity or room can be designed to enable a standard wheelchair to move 90°, 180° and/or 360° while in the veterinary kiosk. The size and configuration of the interior cavity or room can be designed to provide sufficient room for the user so that the user can easily move within the interior cavity or room and/or the user does not feel cramped or claustrophobic when in the interior cavity or room; however, this is not required.

In still yet another and/or alternative non-limiting aspect of the invention, the novel method and apparatus for providing veterinary services, diagnoses, health, and/or wellness advice to individuals can be designed to provide a convenient and low-cost structure (e.g., veterinary kiosk) that can be placed in many different locations, and which enables a user to conveniently access and obtain medical advice and/or care for his/her animal. Veterinary providers that are located locally or throughout the world can be used to communicate with the user accessing the veterinary kiosk. As such, the veterinary services can be offered year around and at all times so long as there is a qualified veterinary provider somewhere in the world that is available and is qualified to provide medical assistance via the veterinary kiosk. Such an arrangement can be more convenient to the veterinary provider since the veterinary provider can work from home or from some other convenient location. The arrangement is also convenient to the user since the user can access medical assistance via the veterinary kiosk at the time and place of choosing. Indeed, in rural areas or smaller communities that do not have a local hospital or local doctors' offices nearby, the installation of a veterinary kiosk in the local drug store, department store, grocery store, etc., results in more accessible and timely medical care for the animal of the user in such communities. The costs associated with providing medical care via the veterinary kiosk may be less than if the user seeks medical assistance from an animal hospital, animal clinic or veterinary office, thus resulting in the user potentially saving money. As can be appreciated, other or additional advantages may exist by the method of the present invention.

In another and/or alternative non-limiting aspect of the invention, the novel method and apparatus for providing veterinary services, diagnoses, health, and/or wellness advice to individuals can include the use of a mobile device (e.g., smart phone, tablet, Ipad™, Ipod™, PDA, etc.) and/or computer (e.g., desktop computer, laptop computer, ultra-light computer, etc.) to enable a user to 1) conveniently locate an available veterinary kiosk, 2) schedule an appointment (e.g., date and/or time), 3) pre-register symptoms and/or reasons for visit, 4) set and/or cancel an appointment, 5) received reminders and/or updates regarding appoints, 6) obtain information about veterinary kiosk availability, 7) obtain information about certain veterinary provider availability, 8) obtain information about the available veterinary provider (e.g., name, specialty, etc.), 9) enable the selection of a certain veterinary provider and/or veterinary provider in a certain field of medicine, 10) obtain map information, address information and/or hours of operation information regarding selected veterinary kiosk, 11) locate closest kiosk and/or kiosk availability for a certain veterinary provider and/or veterinary provider in a certain field of veterinary medicine, 12) presubmit and/or preclear medical insurance, 13) submit payment information, 14) receive information on payment status, 15) receive information on insurance coverage, 16) receive appointment reminders and/or updates, 17) receive prescription information, 18) submit payment information for medical visit and/or prescription, 19) answer surveys regarding the use of the veterinary kiosk, and/or 20) receive medication reminders. The size, shape, configuration and look of the veterinary kiosk are non-limiting. In one non-limiting embodiment, this invention will allow user to schedule appointments using a user portal through a computer and/or mobile device; however, this is not required. Another non-limiting aspect of the application will allow the user to select the kiosk location for their appointment. While selecting their appointment time and/or location, the user can also fill out the symptom survey, select the time of their appointment, and/or select a veterinary provider if they choose; however, this is not required. The application can also allow the user to receive appointment reminders via mobile device, text, phone, cell phone, web-page, and/or email; however, this is not required. The application may also allow for user to cancel or change their appointment; however, this is not required.

In still another and/or alternative embodiment of the invention, the novel method and apparatus for providing veterinary services, diagnoses, health, and/or wellness advice to individuals can include a mobile application for a portable device (e.g., smart phone, PDA, Blackberry™ device, mobile note device, Ipad™, Kindle™ device, Nook™ device, tablet device, etc.) and/or a computer-based application (e.g., desktop computer, laptop computer, ultra-light computer, etc.) that when launched gives the user a series of options that can include, but are not limited to, finding a veterinary kiosk, set medication reminders, visit the home page of the veterinary kiosk operator, etc. As can be appreciated other and/or additional information can be included on the welcome screen of the mobile application and/or computer-based application. The mobile application and/or computer-based application can be designed to enable a user to 1) search or and/or locate veterinary kiosks in one or more communities, towns, cities, states, countries, etc., 2) determine the distance a user is from a veterinary kiosk, 3) obtain the directions to a veterinary kiosk, 4) view the waiting status and/or availability of a particular veterinary kiosk, 5) obtain a map to the selected kiosk, 6) obtain information about the hours available for the veterinary kiosk, 7) obtain information about the actual location picture of the veterinary kiosk, 8) allow a user to make appointment with the veterinary kiosk, 9) provide information on the animal hospital and/or veterinary provider associated with the veterinary kiosk, 10) provide information on which insurance carriers provide coverage for use of the veterinary kiosk, 11) obtain information on whether a particular veterinary provider is part of the veterinary kiosk network of veterinary providers, 12) obtain public comments about the veterinary kiosk, 13) contact a helpdesk that provides information about the veterinary kiosk, 14) schedule an appointment (e.g., date and/or time), 15) pre-register symptoms and/or reasons for visit, 16) enter information required to create an appointment (e.g., personal information, date and time of appointment, particular veterinary kiosk, particular veterinary provider, insurance information, payments, ID verification, insurance card, etc.), 17) set and/or cancel an appointment, 18) receive reminders and/or updates regarding appointments, 19) obtain information about the available veterinary provider (e.g., name, specialty, etc.), 20) enable the selection of a certain veterinary provider and/or veterinary provider in a certain field of medicine, 21) locate closest kiosk and/or kiosk availability for a certain veterinary provider and/or veterinary provider in a certain field of medicine, 22) presubmit and/or preclear medical insurance, 23) submit payment information, 24) receive information on payment status, 25) receive information on insurance coverage, 26) receive appointment reminders and/or updates, 27) receive medication reminders, and/or 28) receive visit summaries; however, this is not required. In one particular non-limiting arrangement, the mobile application and/or computer-based application enables a user to schedule an appointment at a veterinary kiosk. The creation of the appointment can be designed to enable the user to a) select the day and/or the time of the appointment, b) select a particular veterinary provider or type of veterinary provider (e.g., pulmonary doctor, gynecologist, etc.), c) provide a reason for visit and/or provide the animal's symptoms, and/or d) set appointment and medication reminders; however, this is not required. As can be appreciated, other and/or additional information can be inputted by the user when making an appointment (e.g., animal sex, animal age, animal weight, animal height, animal medical history, animal breed, use of current medications, symptom, allergies, etc.). The mobile application and/or computer-based application can be designed to create an appointment confirmation screen along with text and/or email reminder options; however, this is not required. The confirmation screen, when provided, can provide information about the veterinary provider; however, this is not required. The confirmation screen, when provided, can be designed to enable the user to change/cancel the appointment; however, this is not required. Several non-limiting advantages of the present invention include allowing a user to decide which kiosk location is most convenient for the user. The mobile application and/or computer-based application may include an override for "first available" in regards to physician selection; however, this is not required. The user also may be able to check availability of a preferred veterinary provider and/or the kiosk location; however, this is not required.

In yet another and/or alternative embodiment of the invention, the novel method and apparatus for providing veterinary services, diagnoses, health, and/or wellness advice to individuals can include a Provider Application wherein the veterinary provider can contact another veterinary provider during a user visit if a special need or question arises during the user visit wherein the medical provide believes and/or the user request a second opinion and/or an opinion from an animal specialist; however, this is not required. The Provider Application can be designed to enable two or more veterinary providers to be simultaneously viewed and/or heard by the user in the veterinary kiosk; however, this is not required. The Provider Application can be designed to allow only one veterinary provider at a time to be viewed and/or heard by the user in the veterinary kiosk; however, this is not required. The Provider Application can be designed to allow an interpreter to appear to the veterinary provider and/or user (e.g., language translator, sign language translator, etc.); however, this is not required. The Provider Application can be designed to allow a veterinary provider provide to contact another party (e.g., user, guardian, relative, etc.) to obtain information, authorization, etc. about/for a user using the veterinary kiosk; however, this is not required.

In still yet another and/or alternative embodiment of the invention, the novel method and apparatus for providing veterinary services, diagnoses, health, and/or wellness advice to individuals can include an administrator application allowing a medical administrator to remotely access one or more components of the veterinary kiosk; however, this is not required. The administrator application can optionally include one or more functions selected from the group consisting of 1) allowing remote access to one or more medical devices in the veterinary kiosk, 2) allowing remote access to one or more computers in the veterinary kiosk, 3) allowing remote access to one or more routers in the veterinary kiosk, 4) allowing remote access to one or more displays on the veterinary kiosk, 5) allowing remote access to one or more power supplies in the veterinary kiosk, 6) allowing remote access to one or more servers in the veterinary kiosk, 7) allowing remote access to one or more hard drives in the veterinary kiosk, 8) allowing diagnostics to be executed from a remote location on one or more electronic components in the veterinary kiosk (e.g., computer, router, server, battery backup, hard drive, medical devices, electronic locks, fans, displays, speakers, camera, headphone jack, electronic scale, Bluetooth™ devices, lights, pumps, scanners, touch pad, ID verification devices, printer, etc.), 9) allowing the rebooting and/or reinitializing from a remote location of one or more electronic components in the veterinary kiosk, 10) allowing for review of the current and/or past status from a remote location of one or more electronic components in the veterinary kiosk, 11) allowing hardware and/or software updates to be remotely sent and/or loaded onto one or more electronic components in the veterinary kiosk, and/or 12) allowing software to be loaded onto and/or removed from one or more electronic components in the veterinary kiosk.

In another and/or alternative embodiment of the invention, the novel method and apparatus for providing veterinary services, diagnoses, health, and/or wellness advice to individuals can include a pharmaceutical dispensing system that dispenses medications to the user; however, this is not required. The pharmaceutical dispensing system can be located on the veterinary kiosk or be a unit separate from the medical device. The pharmaceutical dispensing system can be designed to allow the user to obtain the medication with or without the assistance of the veterinary attendant. The pharmaceutical dispensing system can be designed to only dispense medication that was authorized by the veterinary provider. In one non-limiting arrangement, the veterinary provider can use the Provider Application to send instructions to the pharmaceutical dispensing system to dispense certain types and/or amounts of medication to the user; however, this is not required. Such information can be stored by the veterinary provider in the animal record of the user; however, this is not required. The veterinary provider can send notification to the veterinary attendant that medication is being dispensed to the user; however, this is not required. The send information can include type and/or quantity of medication; however, this is not required. The payment for medication and/or materials from the pharmaceutical dispensing system can be by mobile device, payment at the veterinary kiosk, payment at attendant's station, and/or payment at the pharmaceutical dispensing system and/or by some other method and/or at some other location.

In still another and/or alternative embodiment of the invention, the novel method and apparatus for providing veterinary services, diagnoses, health, and/or wellness advice to individuals can include a data port and/or wireless receiver that can be used by a user to download and/or upload information to a medical device on a user. Such information can be designed to be viewed by the veterinary provider, and/or data can be sent to the medical device by the veterinary provider; however, this is not required.

In yet another and/or alternative embodiment of the invention, the novel method and apparatus for providing veterinary services, diagnoses, health, and/or wellness advice to individuals can be designed to be transported to various locations to be used as an emergency medical station; however, this is not required. For example, after a natural disaster (e.g., flood, hurricane, tidal wave, earthquake, fire, tornado, etc.), the veterinary kiosk of the present invention can be transported to the area of the incident and then be used as an emergency veterinary medical station. As can be appreciated, the veterinary kiosk can be continuously transported to various locations (e.g., remote rural locations, camp sites, etc.) to enable individuals in such locations to obtain veterinary medical assistance.

In still yet another and/or alternative embodiment of the invention, the novel method and apparatus for providing veterinary services, diagnoses, health, and/or wellness advice to individuals can be designed to allow a user to rate the veterinary provider and/or to view the ratings of veterinary providers that have offered services to other users in the veterinary kiosk; however, this is not required. Such ratings can be used by user to select a certain veterinary provider for a visit, if such option is available.

In another and/or alternative embodiment of the invention, the novel method and apparatus for providing veterinary services, diagnoses, health, and/or wellness advice to individuals can be designed to allow the user to rate the experience received in the veterinary kiosk and/or to view the ratings of other users that have used the veterinary kiosk; however, this is not required.

In still another and/or alternative embodiment of the invention, the novel method and apparatus for providing veterinary services, diagnoses, health, and/or wellness advice to individuals can be designed to automatically order supplies for the veterinary kiosk based on the usage of the medical devices in the veterinary kiosk; however, this is not required. For example, the number of users using the veterinary kiosk can be monitored. If a thermometer was used for every visit, a software program can be used to automatically order the disposable component of the thermometer after a certain number of users have visited the veterinary kiosk; however, this is not required. In another and/or additional example, software can be used to monitor the number of times a medical door for a medical device has been opened. Based on such number of door openings, a software program can be used to automatically order the disposable component of the medical device in a certain medical compartment after a certain number of door openings has been detected; however, this is not required.

In still yet another and/or alternative embodiment of the invention, the novel method and apparatus for providing veterinary services, diagnoses, health, and/or wellness advice to individuals can be designed to generate a fresh scent in the veterinary kiosk; however, this is not required. The type of scent and/or method of scent delivery are non-limiting.

In another and/or alternative embodiment of the invention, the novel method and apparatus for providing veterinary services, diagnoses, health, and/or wellness advice to individuals can be designed to collect information about the user, user retention, and/or user referrals for use in the marketing of the veterinary kiosk and/or to improve/alter/enhance the services provided by the veterinary kiosk; however, this is not required.

In still another and/or alternative embodiment of the invention, the novel method and apparatus for providing veterinary services, diagnoses, health, and/or wellness advice to individuals can designed to print and/or send coupons, advertisements, marketing literature, and/or medical literature to a user that has used the veterinary kiosk and/or has registered with the veterinary kiosk; however, this is not required. Such coupons, advertisements, marketing literature, and/or medical literature can be general in nature and/or targeted to the particular user and/or type of diagnoses for an animal that was received by the user. For example, if a prescription has been written by the veterinary provider, one or more pharmacies and/or pet stores may have a coupon sent to the user to provide the user with a discount, etc. if the user fills the prescription at the pharmacy; however, this is not required.

In yet another and/or alternative embodiment of the invention, the novel method and apparatus for providing veterinary services, diagnoses, health, and/or wellness advice to individuals can utilize a means to register the pet\animal to be examined on the outside of the kiosk enclosure. Registration could be completed using a touch screen mounted to the outside of the kiosk or entered in by an assistant on a computer. A printer may also be present on the outside of the kiosk to print, including but not limited to, registration information, animal information, advertisements, coupons, or visit summary. A scale may be located outside the kiosk to obtain the animal weight or it may be incorporated within the examination table. A credit card reader may be utilized to take payment during registration or after the exam. The kiosk can include an enclosure with one or more entrances/exits. The walls of the kiosk can create an enclosure that will retain the animal within the kiosk during the evaluation. The walls can be of various heights, designs and fabricated using various manufacturing and assembly techniques. The floor will either be the floor of the location the kiosk is assembled on or a water tight floor for easy cleanup. The kiosk may or may not utilize a roof over the kiosk to provide more privacy within the enclosure. If a roof is installed may utilize a ventilation system to maintain a pleasant environment. The kiosk may also utilize various scent-producing techniques to eliminate animal smells. The inside of the kiosk can include a method for the remotely located veterinarian, technician or other qualified person (known as the provider) to communicate with the people within the kiosk. Communication may be through one or more cameras, microphones, speakers, displays and/or touch screens. The examination can utilize a stationary or mobile, adjustable height or stationary height examination table to place the animal in the proper position to complete the examination. The examination can be performed by the remote provider using any combination of the following examination devices: otoscope, dermascope, thermometer, blood pressure monitor, stethoscope, cameras in various positions in the kiosk, microphone, stadiometer/height gauge, grooming tool(s), and/or other devices as required by the veterinary provider. The examination devices can be mounted within the kiosk in medical device cabinets or cubby holes with manually, automatic and/or remotely controlled doors. The doors can be opened or closed by the on-site assistant or by the remote veterinary provider as the tools are needed. These cabinets may be located on any wall or walls of the kiosk and/or may be located in external enclosures that are located within the kiosk. An alternative and/or additional mounting method for the examination devices is to mount one or more medical device directly to the wall or suspend the device overhead. An examination lamp may also be installed within the kiosk to provide better lighting. The veterinary provider can use a computer/laptop/tablet/phone fitted with a camera, microphone and software to communicate remotely with the examination hardware, the kiosk devices, the animal owner and/or technician that is located at or within the kiosk. The veterinary provider can be allowed to communicate with the medical assistant through an interface outside the kiosk; however, this is not required.

It is one non-limiting object of the invention to provide tele-med services for veterinary services that are convenient to a user.

It is another and/or alternative non-limiting object of the invention to provide tele-med services for veterinary services that are cost effective to a user.

It is still another and/or alternative non-limiting object of the invention to provide tele-med services for veterinary services that can be provided to a user via a veterinary kiosk.

It is yet another and/or alternative non-limiting object of the invention to provide tele-med services for veterinary services that can be provided to a user via a modular veterinary kiosk.

It is still yet another and/or alternative non-limiting object of the invention to provide a veterinary kiosk and method for using a veterinary kiosk that is easy to assemble and disassemble.

It is another and/or alternative non-limiting object of the invention to provide a veterinary kiosk and method for using a veterinary kiosk that includes an easy and convenient registration system and payment system.

It is still another and/or alternative non-limiting object of the invention to provide a veterinary kiosk and method for using a veterinary kiosk that provides privacy to a user when obtaining veterinary services.

It is yet another and/or alternative non-limiting object of the invention to provide a veterinary kiosk and method for using a veterinary kiosk that is sized and shaped to accommodate disabled or handicapped users.

It is still yet another and/or alternative non-limiting object of the invention is to provide a veterinary kiosk and method for using a veterinary kiosk that includes medical instruments that can be used by a user, veterinary assistant and/or veterinary provider when obtaining veterinary services.

It is another and/or alternative non-limiting object of the invention to provide a veterinary kiosk and method for using a veterinary kiosk that includes video conferencing capabilities between a user and a veterinary provider.

It is still another and/or alternative non-limiting object of the invention to provide a veterinary kiosk and method for using a veterinary kiosk that provides the option to play back one or more portions of the video conference session to the user after the video conference between the user and veterinary provider has been completed.

It is yet another and/or alternative non-limiting object of the invention to provide a veterinary kiosk and method for using a veterinary kiosk that includes an attendant station, digital signage, and/or a registration station on the exterior of the veterinary kiosk.

It is still yet another and/or alternative non-limiting object of the invention to provide a veterinary kiosk and method for using a veterinary kiosk that includes a Provider Screen and/or User Screen in the interior of the veterinary kiosk.

It is another and/or alternative non-limiting object of the invention to provide a veterinary kiosk and method for using a veterinary kiosk that includes one or more medical device cabinets on the interior of the veterinary kiosk.

It is still another and/or alternative non-limiting object of the invention to provide a veterinary kiosk and method for using a veterinary kiosk that includes the use of a user Appointment or Registration Application, Attendant Application, User Appointment or Registration Application, Provider Application, Administrator Application, User Portal and/or Provider Portal.

It is yet another and/or alternative non-limiting object of the invention to provide a veterinary kiosk and method for using a veterinary kiosk that includes a user Appointment or Registration Application that enables a user to schedule an appointment at a veterinary kiosk.

It is still yet another and/or alternative non-limiting object of the invention to provide a veterinary kiosk and method for using a veterinary kiosk that includes a user Appointment or Registration Application that enables a user to enter insurance information and/or to make a payment and/or co-pay for the medical visit in the kiosk.

It is another and/or alternative non-limiting object of the invention to provide a veterinary kiosk and method for using a veterinary kiosk that includes a User Registration System that enables a user to check-in for a preexisting appointment.

It is still another and/or alternative non-limiting object of the invention to provide a veterinary kiosk and method for using a veterinary kiosk that includes a User Registration System that enables a user to identify the animal's symptoms, medications, allergies, and/or medical conditions.

It is yet another and/or alternative non-limiting object of the invention to provide a veterinary kiosk and method for using a veterinary kiosk that includes registration and/or check-in system that enables a user to request assistance from a veterinary attendant.

It is still yet another and/or alternative non-limiting object of the invention to provide a veterinary kiosk and method for using a veterinary kiosk that includes an Attendant Application that enables a veterinary attendant to monitor past, present and/or future appointments for the veterinary kiosk.

It is another and/or alternative non-limiting object of the invention to provide a veterinary kiosk and method for using a veterinary kiosk that includes an Attendant Application that enables a veterinary attendant to monitor the status of a current visit in the veterinary kiosk.

It is still another and/or alternative non-limiting object of the invention to provide a veterinary kiosk and method for using a veterinary kiosk that includes an Attendant Application that enables a veterinary attendant to cancel and/or reschedule an appointment to a veterinary kiosk.

It is yet another and/or alternative non-limiting object of the invention to provide a veterinary kiosk and method for using a veterinary kiosk that includes an Attendant Application that informs that veterinary attendant that the user requires assistance.

It is still yet another and/or alternative non-limiting object of the invention to provide a veterinary kiosk and method for using a veterinary kiosk that includes an Attendant Application that enables the veterinary attendant to keep track of the clean-up of the veterinary kiosk.

It is another and/or alternative non-limiting object of the invention to provide a veterinary kiosk and method for using a veterinary kiosk that enables the medical assistant to activate an automated sanitation and/or cleaning system of the veterinary kiosk.

It is still another and/or alternative non-limiting object of the invention to provide a veterinary kiosk and method for using a veterinary kiosk that includes an Attendant Application that enables a medical assistant to validate the insurance and/or ID of an animal and/or user.

It is yet another and/or alternative non-limiting object of the invention to provide a veterinary kiosk and method for using a veterinary kiosk that includes a user Appointment or Registration Application that helps the user capture vitals and/or enter the vitals information for the animal during the visit.

It is still yet another and/or alternative non-limiting object of the invention to provide a veterinary kiosk and method for using a veterinary kiosk that includes a user Appointment or Registration Application that enables the user to request assistance from the veterinary attendant.

It is another and/or alternative non-limiting object of the invention to provide a veterinary kiosk and method for using a veterinary kiosk that includes a user Appointment or Registration Application that can assist the user during the consultation with the veterinary provider.

It is still another and/or alternative non-limiting object of the invention to provide a veterinary kiosk and method for using a veterinary kiosk that includes a user Appointment or Registration Application that enables a user to take a survey regarding the consultation with the veterinary provider and/or the use of the veterinary kiosk.

It is yet another and/or alternative non-limiting object of the invention to provide a veterinary kiosk and method for using a veterinary kiosk that includes a Provider Application that assists the veterinary provider in providing veterinary services to the user in the veterinary kiosk.

It is still yet another and/or alternative non-limiting object of the invention to provide a veterinary kiosk and method for using a veterinary kiosk that includes a Provider Application that provides information to the veterinary provider regarding past, current and future appointment that have been scheduled with the veterinary provider.

It is another and/or alternative non-limiting object of the invention to provide a veterinary kiosk and method for using a veterinary kiosk that includes a Provider Application that enables the veterinary provider to view personal information about the animal and/or user that the user has entered regarding the medical visit.

It is still another and/or alternative non-limiting object of the invention to provide a veterinary kiosk and method for using a veterinary kiosk that includes a Provider Application that enables the veterinary provider to view vitals that have been collected on the animal.

It is yet another and/or alternative non-limiting object of the invention to provide a veterinary kiosk and method for using a veterinary kiosk that includes a Provider Application that enables the veterinary provider to request that the veterinary attendant assist the user in the veterinary kiosk.

It is still yet another and/or alternative non-limiting object of the invention to provide a veterinary kiosk and method for using a veterinary kiosk that includes a Provider Application that enables the veterinary provider to control the use and/or access of one or more medical devices in the veterinary kiosk.

It is another and/or alternative non-limiting object of the invention to provide a veterinary kiosk and method for using a veterinary kiosk that includes a Provider Application that enables a veterinary provider to create a visit summary of the user in the veterinary kiosk.

It is still another and/or alternative non-limiting object of the invention to provide a veterinary kiosk and method for using a veterinary kiosk that includes a Provider Application that enables the veterinary provider to update personal information, medical history information and/or symptom information about the animal and/or the user.

It is yet another and/or alternative non-limiting object of the invention to provide a veterinary kiosk and method for using a veterinary kiosk that includes a Provider Application that enables a veterinary provider to select and/or enter a diagnosis for an animal.

It is still yet another and/or alternative non-limiting object of the invention to provide a veterinary kiosk and method for using a veterinary kiosk that includes a Provider Application that enables the veterinary provider to enter notes about the animal and/or user and/or create a treatment plan for the animal.

It is another and/or alternative non-limiting object of the invention to provide a veterinary kiosk and method for using a veterinary kiosk that includes a Provider Application that enable a veterinary provider to view information about past visits by the animal and/or the user.

It is still another and/or alternative non-limiting object of the invention to provide a veterinary kiosk and method for using a veterinary kiosk that includes a mobile application and/or an on-line application that enables a user to 1) conveniently locate an available veterinary kiosk, 2) schedule an appointment (e.g., date and/or time), 3) pre-register symptoms and/or reasons for visit, 4) set and/or cancel an appointment, 5) receive reminders and/or updates regarding appoints, 6) obtain information about veterinary kiosk availability, 7) obtain information about certain veterinary provider availability, 8) obtain information about the available veterinary provider (e.g., name, specialty, etc.), 9) enable the selection of a certain veterinary provider and/or veterinary provider in a certain field of veterinary medicine, 10) obtain map information, address information and/or hours of operation information regarding selected veterinary kiosk, 11) locate the closest kiosk and/or the best kiosk availability for a certain veterinary provider and/or veterinary provider in a certain field of medicine, 12) presubmit and/or preclear medical insurance, 13) submit payment information, 14) receive information on payment status, 15) receive information in insurance coverage, 16) receive appointment reminders and/or updates, and/or 17) receive medication reminders, and the like.

It is yet another and/or alternative non-limiting object of the invention to provide a veterinary kiosk and method for using a veterinary kiosk that includes a scale in the veterinary kiosk.

It is still yet another and/or alternative non-limiting object of the invention to provide a veterinary kiosk and method for using a veterinary kiosk that includes a medication adherence application that allows a user to 1) speak to a pharmacist and/or veterinary provider, 2) change the user's medication alerts, 3) learn about certain types of medical conditions, 4) check medication orders status, 5) check medication delivery status, 6) refill a prescriptions, 7) transfer prescriptions to a another location, 8) obtain information about recommended medication dosages, 9) obtain information about recommended times to take medications, 10) obtain information about recommended frequency for taking medications, 11) obtain information about medications, 12) obtain information about generic brands available for medications, 13) request an appointment to speak with a veterinary provider, 14) enter information regarding compliance information regarding medication usage by animal, and/or 15) receive compliance reports for animal regarding medication usage.

It is another and/or alternative non-limiting object of the invention to provide a veterinary kiosk and method for using a veterinary kiosk that includes a medication adherence application that 1) sends reminders to user to reminder the user give medications to the animal, 2) monitors a user's adherence to giving meds to the animal and/or distributes progress reports to the user, and/or 3) automatically enrolls a user in an electronic prescriptions network which can optionally send a user's prescriptions to their choice of pharmacy, pet store, etc.

It is still another and/or alternative non-limiting object of the invention to provide a veterinary kiosk and method for using a veterinary kiosk that includes one or more headphone jacks in the veterinary kiosk.

It is yet another and/or alternative non-limiting object of the invention to provide a veterinary kiosk and method for using a veterinary kiosk that includes a veterinary kiosk having HD components and an industrial strength design.

It is still yet another and/or alternative non-limiting object of the invention to provide a veterinary kiosk and method for using a veterinary kiosk that includes a veterinary kiosk having a modular configuration and/or a configuration that enables the veterinary kiosk to be brought in to and/or removed from locations having a standard sized doorway.

It is another and/or alternative non-limiting object of the invention to provide a veterinary kiosk and method for using a veterinary kiosk that includes a veterinary kiosk having a check-in registration system positioned on the exterior of the veterinary kiosk.

It is still another and/or alternative non-limiting object of the invention to provide a veterinary kiosk and method for using a veterinary kiosk that includes a veterinary kiosk having one or more medical device cabinets located in the interior of the veterinary kiosk.

It is yet another and/or alternative non-limiting object of the invention to provide a veterinary kiosk and method for using a veterinary kiosk that includes a veterinary kiosk having digital signage on the interior and/or exterior of the veterinary kiosk.

It is still yet another and/or alternative non-limiting object of the invention to provide a veterinary kiosk and method for using a veterinary kiosk that includes a veterinary kiosk having a built-in sanitation system.

It is another and/or alternative non-limiting object of the invention to provide a veterinary kiosk and method for using a veterinary kiosk that allows the user to 1) choose between name brand and generic drugs, 2) choose the supply quantity for the prescription (i.e., 30 day supply, 60 day supply, 90 day supply, etc.), 3) choose between picking the prescription up at the pharmacy, pet store, etc. of their choice or mail delivery of the prescription, 4) enter medical insurance for partial or full payment of the prescription, 5) enter a credit or debit card information to pay for the prescription, 6) enter information for mail delivery of the prescription, 8) enter information to provide automatic reminders to user regarding refilled and/or follow-up medical visits, 9) enter information to enable user to be notified when prescription has been mailed and/or is ready to be picked up at the pharmacy (however, this is not required), 10) obtain a print out and/or electronic version of the prescription written by the veterinary provider, and/or 11) receive information about the issued prescription (e.g., prescribed use, side effects, etc.) in printout and/or electronic form.

It is still another and/or alternative non-limiting object of the invention to provide a veterinary kiosk and method for using a veterinary kiosk that includes a veterinary kiosk having a movable front interior wall panel to enable access to components that are positioned behind the front interior wall of the veterinary kiosk.

These and other objects and advantages will become apparent to those skilled in the art upon reading and following the description taken together with the accompanying drawings.

BRIEF DESCRIPTION OF THE DRAWINGS

Reference may now be made to the drawings which illustrate various preferred embodiments that the invention may take in physical form and in certain parts and arrangement of parts wherein.

DETAILED DESCRIPTION OF NON-LIMITING EMBODIMENTS

Figure 1:
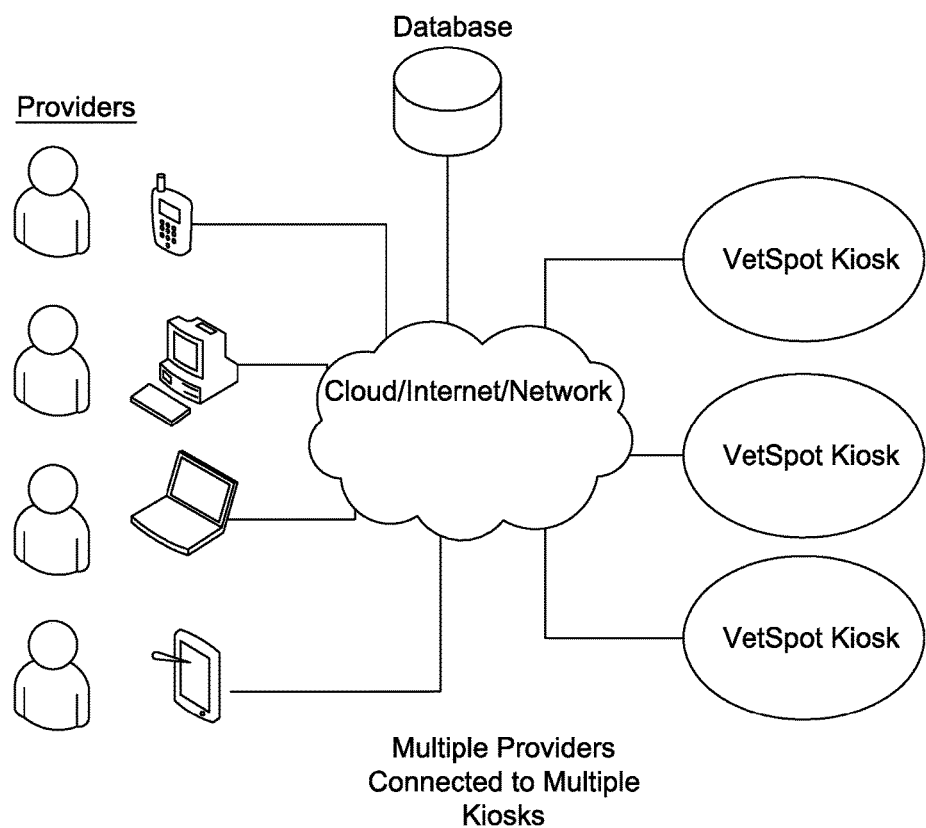
FIG. 1 block diagram of one non-limiting system for providing veterinary services to one or more veterinary kiosks in accordance with the present invention.

Referring now to the drawings wherein the showings are for the purpose of illustrating one non-limiting embodiments of the invention only and not for the purpose of limiting same, FIGS. 1-7 illustrate non-limiting embodiments of the veterinary kiosk and method of use of one or more veterinary kiosks in accordance with the present invention. The veterinary kiosk 100 is designed to be used by a user to obtain veterinary services for one or more animals of a user. The number and/or type of animal is non-limiting. The veterinary services provided via the veterinary kiosk are tele-med services wherein one or more veterinary providers located at a remote location provide veterinary services to one or more users that are using the veterinary kiosk. As can be appreciated, non-tele-med services can also be provided to a user that is using the veterinary kiosk (e.g., obtaining information from veterinary assistant located at veterinary kiosk, obtaining information from a database located at the veterinary kiosk, using an automated diagnosis system located at the veterinary kiosk, etc.).

The shape, size and configuration of the veterinary kiosk are non-limiting. The materials and colors of the veterinary kiosk are also non-limiting. Generally, the materials used to form the veterinary kiosk include materials that resist or prevent microbial growth; however, this is not required. The veterinary kiosk illustrated in FIGS. 2-7 is designed to accommodate about 1-2 adults and 1-4 animals; however, it can be appreciated that the veterinary kiosk can be designed to accommodate additional users and/or animals.

The veterinary kiosk is generally designed to be modular so that it can be easily assembled and disassembled; however, this is not required. The veterinary kiosk generally includes a floor panel 110; however, this is not required. The floor panel, when used, can be a one- or two-piece unit; however, the floor panel can be formed of more than two pieces. A rail system can be positioned about the floor panel to facilitate in connecting other components of the veterinary kiosk to the floor panel; however, this is not required. The rail system, when used, can be connected to the floor panel and/or other components of the veterinary kiosk in a variety of ways. The floor panel is generally formed of a durable material (e.g., plastic, metal, wood, composite material, man-made materials, etc.). The floor panel can be formed of a slightly compressible material to facilitate in the comfort of walking on the floor panel; however, this is not required. The floor panel is illustrated as having an oval shape; however, other shapes can be used (e.g., circular, square, rectangular, polygonal, etc.). The maximum length of the floor panel is generally 3-15 feet, typically 4-12 feet, more typically about 6-10 feet, and even more typically about 8-9 feet; however, other lengths can be used. The maximum width of the floor panel is generally 3-10 feet, typically 4-8 feet, and more typically about 4-6 feet; however; other widths can be used. The top surface area of the floor panel is generally 10-150 sq. ft., typically 15-80 sq. ft., and more typically about 50-60 sq. ft.; however, other surface areas of the floor panel can be used. The floor panel can be sized to enable a user in a wheelchair to enter the veterinary kiosk and turn and/or fully maneuver in the veterinary kiosk while sitting in the wheelchair; however, this is not required. The thickness of the floor panel is generally about 0.1-5 inches, and typically about 0.25-3 inches; however, other thicknesses of the floor panel can be used.

An examination table/weight scale 120 can optionally be positioned in the kiosk. As can be appreciated, the examination table can be absent a weight scale or the weight scale can be located in other regions of the veterinary kiosk (e.g., floor, chair, bench, etc.). The weight scale, when used, provides information about the weight of the animal. The information from the scale can be electronically (e.g., wired, wirelessly) transferred to a veterinary provider and/or displayed to the user and/or veterinary provider. The examination table, when used, can be used for positioning the animal during the examination of the animal. The top portion 122 of the examination table can be supported by one or more legs 124. The one or more legs can function as a part of the scale; however, this is not required. The size, shape and configuration of the examination table is non-limiting. The location of the examination table in the kiosk is non-limiting. Generally, the top surface of the examination table is located above the floor of the kiosk; however, this is not required. One or more lights 130 can be located above the examination table; however, this is not required. The one or more lights, when used, can be connected to articulate arms or other arrangements to enable the one or more lights to be movable; however, this is not required. One or more cameras 140 can be located above the examination table; however, this is not required. The one or more cameras, when used, can be connected to articulate arms or other arrangements to enable the one or more cameras to be movable; however, this is not required. One or more medical devices can be located above the examination table; however, this is not required. The one or more medical devices that are located above the examination table, when used, can be connected to articulate arms or other arrangements to enable the one or more medical devices to be movable; however, this is not required.

A ramp 150 can be optionally used to facilitate entry and exiting of the veterinary kiosk; however, this is not required. The shape and size of the ramp are non-limiting. The ramp can be made of a similar material as the floor panel; however, this is not required. The ramp generally includes a sloped surface to facilitate in transitioning from a floor surface to the top surface of the floor panel; however, this is not required. A ramp connector can be used to connect the ramp to the floor panel; however, this is not required.

The veterinary kiosk can optionally include one or more benches, stools and/or chairs. When a bench is included in the veterinary kiosk, the bench is generally positioned on the back interior wall of the veterinary kiosk; however, this is not required. The bench can be used to allow a user to sit in the veterinary kiosk while waiting for and/or obtaining the veterinary services for the animal in the veterinary kiosk. The bench can be designed to enable one or more persons/animals to sit on the bench. The bench can optionally include a storage space under the seat of the bench that can be used to store supplies, equipment, etc. for the veterinary kiosk. A liftable seat section can be used to access the storage space; however, this is not required. When the bench includes a storage space, the bench can include a door which may or may include a lock to limit access to the storage space; however, this is not required. As can be appreciated, the veterinary kiosk can include one or more chairs, not shown, to enable one or more users to sit in the veterinary kiosk while receiving veterinary services for the animal in the veterinary kiosk.

Figure 2:
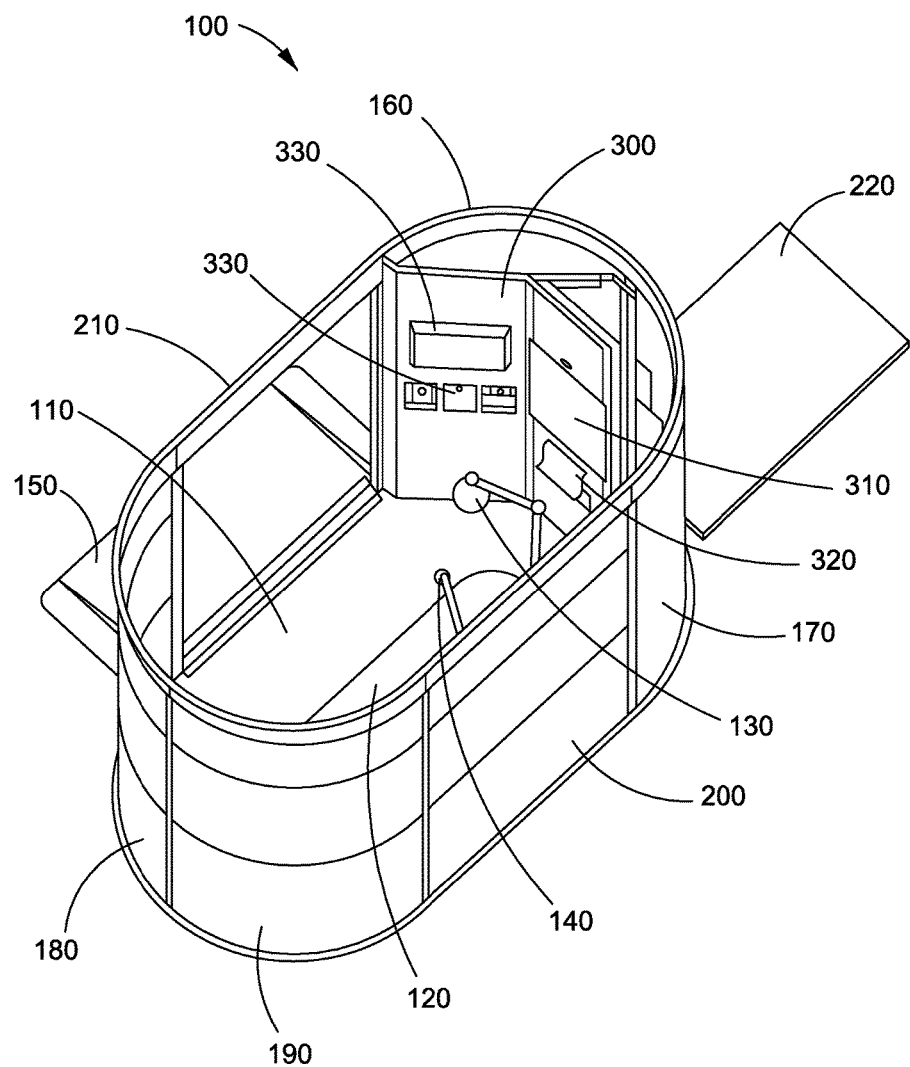
FIG. 2 is a rear-top elevation view of the veterinary kiosk of FIG. 1.
Figure 3:
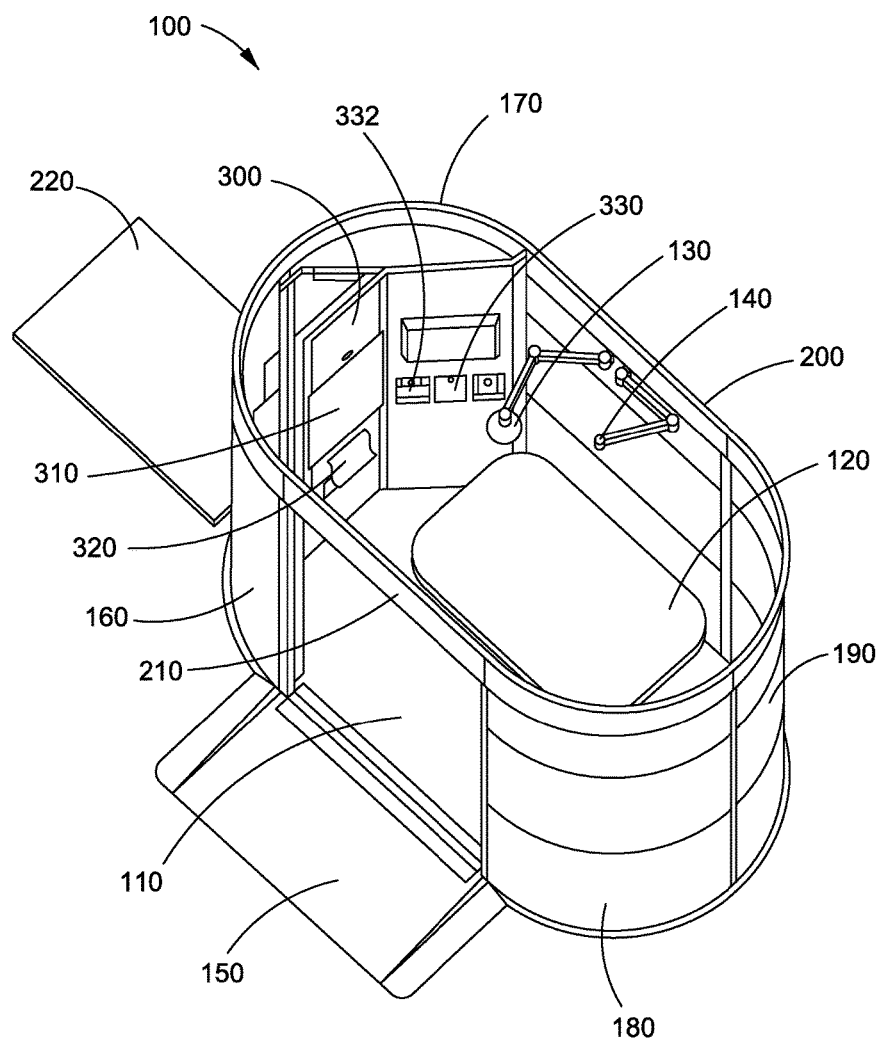
FIG. 3 is a side-top elevation view of the veterinary kiosk of FIG. 1.
Figure 4:
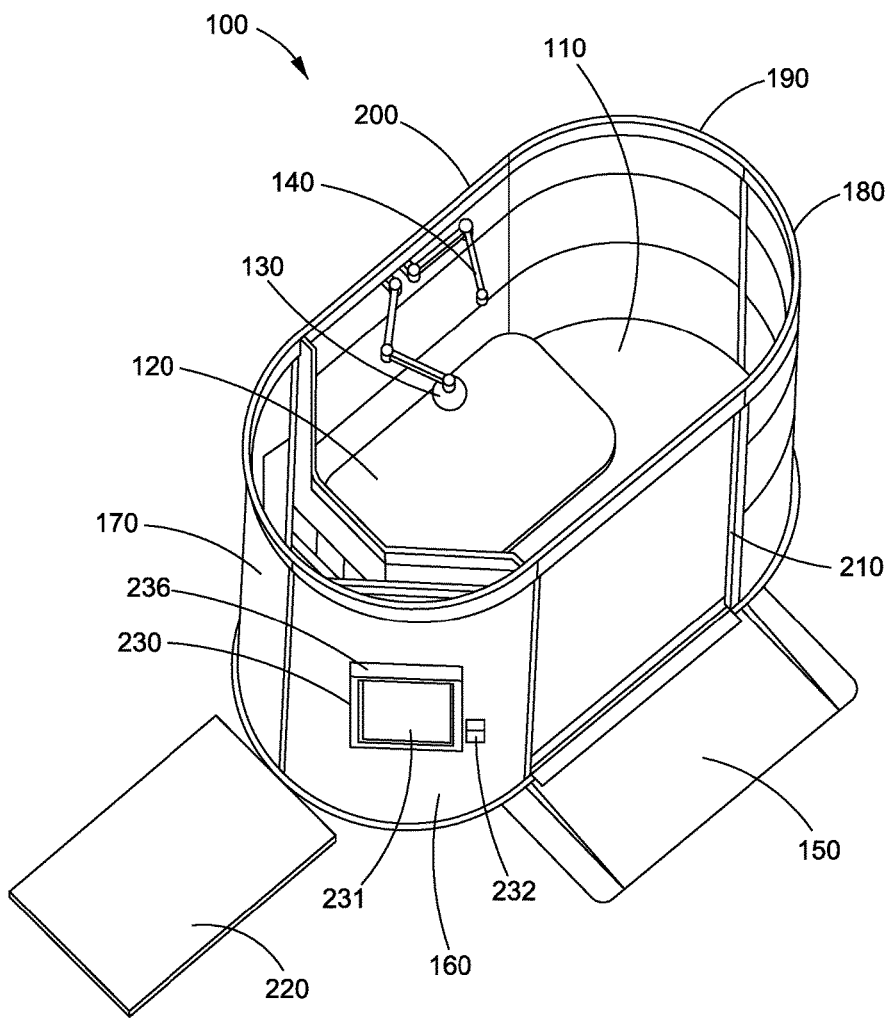
FIG. 4 is a front-top elevation view of the veterinary kiosk of FIG. 1.

The veterinary kiosk is illustrated as having two front panels 160, 170, two rear panels 180, 190, one side wall 200, and one door system 210. The front panels, rear panels, side wall, and door system are generally formed of a durable material (e.g., plastic, metal, wood, composite material, man-made materials, etc.). The front panels, rear panels, side wall can have upper trim; however, this is not required. As can be appreciated, the veterinary kiosk can be designed to only include a single front panel and/or a single rear panel. As can also be appreciated, the veterinary kiosk can be designed to include more than two front panels and/or more than two rear panels. As can be appreciated, the veterinary kiosk can be designed to include more than one side wall and/or more than one door system. As can also be appreciated, a side wall can be substituted for another door system; however, this is not required. The general shape and size of the front and rear panels are the same; however, this is not required. The shape of the front and rear panels is generally arcuate; however, this is not required. The radius of curvature is about 10-100 inches, typically 15-50 inches, and more typically about 20-35 inches; however, other radius of curvatures can be used. As illustrated in FIGS. 2-4, the front and rear panels have an angle of curvature of about 90° or a quarter of a circle; however, it can be appreciated that one or both rear and/or front panels can have different angles of curvature. The general shape and size of the side wall and the door system are generally the same; however, this is not required. As illustrated in FIGS. 2-4, the side wall and door system lie in a generally flat plane; however, this is not required. As illustrated in FIGS. 2-4, the assembly of the front and rear panels and the side wall and door system forms a generally oval shape for the veterinary kiosk; however, other shapes can be formed (e.g., oval, square, rectangle, polygonal, etc.). The two front panels and two rear panels are illustrated as having the same or similar footprint;

however, this is not required. Likewise, the side wall and the door system have the same or similar footprint; however, this is not required. The similarity in the shape and footprint of the wall components of the veterinary kiosk enables the veterinary kiosk to be assembled in a manner that is convenient for the facility that will include the veterinary kiosk. For example, if the door system needs to be positioned on the left side of the veterinary kiosk, instead of the right side, the similarly shaped side wall and door system enables the veterinary kiosk to be assembled in such a manner. Also, if the registration station of the medical system needs to be placed on the left side or right side or on the rear end of the veterinary kiosk instead of the front end, the similarly shaped front and rear panels can be easily exchanged to create such configuration for the veterinary kiosk. The modular veterinary kiosk not only accommodates multiple configurations of the veterinary kiosk, it also facilitates in enabling the veterinary kiosk to be moved into an existing facility and then assembling the veterinary kiosk in such facility without having to modifying the entry ways into or out of the facility. The thickness and height of the front panels, rear panels, side wall and door system are non-limiting. Generally, the maximum height of the front panels, rear panels, side wall and door system is about 5-12 ft., typically about 6-9 ft., and more typically about 7-8 ft.; however, other heights can be used. The thickness of the front panels, rear panels, side wall and door system is generally about 0.5-10 inches, typically about 1-5 inches, and more typically about 1-2 inches; however, other thicknesses can be used. The front panels, rear panels, side wall and door system can optionally include insulation, sound dampening material, etc.; however, this is not required. The front panels, rear panels, side wall and door system can be designed to be connected together in a variety of ways (e.g., bolted/screwed together, latched together, snap fitted together, press fitted together, etc.). Generally, the arrangement is used to connect together the front panels, rear panels, side wall and door system is selected to enable easy connecting and disconnecting of the front panels, rear panels, side wall and door system from one another. One or more of the front panels, rear panels, side wall and door system can include openings, windows, transparent/semi-transparent regions that allow for ventilation, illumination, and/or viewing; however, this is not required. Generally, front panels, rear panels, side wall and door system are mostly or fully formed of opaque or non-transparent materials so as to ensure the privacy of the user in the veterinary kiosk; however, this is not required.

The configuration of the door system 210 is non-limiting. The door system can include a frame and one or two doors. The one or more doors can include a handle or grasp cavity on one or both sides of the one or both doors; however, this is not required. The one or more doors can be designed to open and close in a variety of ways (e.g., swing open and closed, slide open and closed on a top/bottom rail system, etc.). As can be appreciated, the one or more doors for the veterinary kiosk can also or alternatively be positioned on one or more of the front or rear panels; however, this is not required. The maximum height of the doors is generally about 5-9 ft., and typically about 6-7 ft.; however, other heights can be used. The maximum width of the entry provided by the one or more doors when fully open is generally about 15-60 inches, typically about 25-55 inches, and more typically about 30-50 inches; however, other widths can be used. The door opening is generally selected to enable a standard wheelchair to pass through the opening; however, this is not required. The door system can optionally include an indicator (e.g., light, message, etc.) that indicates when the veterinary kiosk is in use or is available. As can be appreciated, the use indicator can be located on other or additional locations on the veterinary kiosk. The door system can optionally include a lock arrangement. The configuration of the lock arrangement is non-limiting. The lock arrangement, when used, can be designed to enable the user to lock the doors to the kiosk medical to prevent access to the interior of the veterinary kiosk while the user is in the veterinary kiosk; however, this is not required. The lock arrangement can also or alternatively be used to lock and prevent access to the interior of the veterinary kiosk when the veterinary kiosk is not in use and/or being cleaned; however, this is not required.

The veterinary kiosk can optionally include an exterior attendant station that is connected to and/or positioned near the veterinary kiosk. The exterior attendant station can be used by one or more attendants, veterinary providers, etc. As illustrated in FIGS. 2-4, a desk 220 can be connected to and/or positioned next to an exterior wall of the veterinary kiosk. The desk can be formed of one or more pieces. When the desk is designed to be connected to an exterior wall of the veterinary kiosk, such connection arrangement is not limited (e.g., screw, bolt, clamp, press fit, snap arrangement, etc.). The desk can include a desk top, one or more legs, one or more shelf regions, one or more cabinet doors, one or more shelves, one or more drawers, etc. The one or more doors and/or drawers, when used, can optionally include a lock. The desk top can optionally include an opening for cables, etc. One or more chairs can be used to allow one or more attendants, veterinary providers, etc. to sit at the desk. The desk can be used to support a computer, printer, files, supplies, medical devices, refrigerator, freezer, medicine, animal blood and/or urine samples, animal stool samples, fur samples, skin samples, phone, monitor, scanner, credit card reader, etc. The one or more one or more attendants, veterinary providers, etc. located at the desk can assist a user in using the veterinary kiosk, maintain and/or clean the veterinary kiosk, provide veterinary services to a user of the veterinary kiosk, etc. The desk is illustrated as positioned at or adjacent to one or both front panels; however, this is not required. Generally, the attendant, when used, is not a veterinary provider; however, this is not required. The attendant, when used, is generally trained to assist a user to use the veterinary kiosk; however, this is not required. The attendant can 1) provide assistance to a user during the registration process and/or payment process, 2) provide assistance to a user about the veterinary kiosk and/or how to use the veterinary kiosk, 3) provide assistance to a user regarding technology in the veterinary kiosk and/or how to use such technology in the veterinary kiosk, 4) provide assistance to a user to enter and/or exit the veterinary kiosk, 5) clean and/or sanitize the veterinary kiosk, 6) answer and/or assist the user in other ways regarding the veterinary kiosk and/or services provided by the veterinary kiosk, 7) assist in the registration, appointment and/or check-in process for a user, etc.

The veterinary kiosk can optionally include a ceiling panel. The ceiling panel can be formed of one or more pieces. The ceiling panel can be formed of a transparent or semi-transparent material to allow light to enter and illuminate the interior of the veterinary kiosk for partial or fully ambient lighting of the veterinary kiosk; however, this is not required. One or more lights can be positioned on the ceiling panel to illuminate the interior of the veterinary kiosk; however, this is not required. The ceiling panel can optionally include one or more vents to enable air to circulate inside the veterinary kiosk; however, this is not required. One or more fans can be positioned on or adjacent to one or more of the vents; however, this is not required. As can be appreciated, the location of the one or more fans, when used, is non-limiting. As can also be appreciated, one or more fan systems, when used, can also or alternatively be positioned on other components of the veterinary kiosk (e.g., front panel, back panel, side wall, door system, floor panel, etc.). One or more fan systems, when used, and/or vents can optionally include a filter system, to partially or fully filter dust, mites, airborne particles, micro-organisms, viruses, etc. from the air prior to the air entering into the veterinary kiosk and/or prior to the air exiting the veterinary kiosk; however, this is not required. The filter can include many different arrangements (e.g., HEPA filter, electronic filter, liquid filter, etc.).

The veterinary kiosk can optionally include a cleaning system that is designed to clean one or more portions of the interior of the veterinary kiosk and/or kill/neutralize some or all germs and/or other micro-organisms in the veterinary kiosk. One non-limiting cleaning system that can be used is a UV sanitizing system. As can also be appreciated, a mist sanitizer can also or alternatively be used to fully or partially clean/sanitize one or more portions of the veterinary kiosk. The UV sanitizing system, when used, can be connected to or positioned adjacent to the ceiling panel and/or rear panels; however, this is not required. The UV sanitizing system generally includes one or more UV lights that are designed to kill some or all of the germs and/or other micro-organisms in the veterinary kiosk. Generally, the germs and/or other micro-organisms in the veterinary kiosk are treated when the interior of the veterinary kiosk does not include a user. The UV sanitizing system can optionally include one or more standard lights that can be used to provide illumination in the veterinary kiosk; however, this is not required. The UV sanitizing system can optionally include one or more vents that allow air drawn into the veterinary kiosk by a fan system to flow into the interior of the veterinary kiosk; however, this is not required. The UV sanitizing system can optionally include a cooling fan for the one or more UV lights and/or optional standard lights; however, this is not required. The UV sanitizing system can optionally include all or a portion of a mist sanitizing system; however, this is not required. The UV sanitizing system can house one or more cameras, speakers, microphones, deodorizers, sensors (e.g., temperature sensor, motion sensor, sound sensor, etc.), etc. for use in the veterinary kiosk; however, this is not required. The shape, size and configuration of the UV sanitizing system are non-limiting. When a mist sanitizing system is additionally or alternatively used, one or more mist nozzles can be located in one or more regions of the veterinary kiosk so as to direct the sanitizing mist to desired locations in the veterinary kiosk. The sanitizing system, when used, can be activated by an attendant and/or a veterinary provider while the veterinary kiosk is not being used by a user. The doors to the veterinary kiosk can be closed and/or locked to prevent a user from entering the veterinary kiosk during a sanitizing process; however, this is not required.

Figure 5:
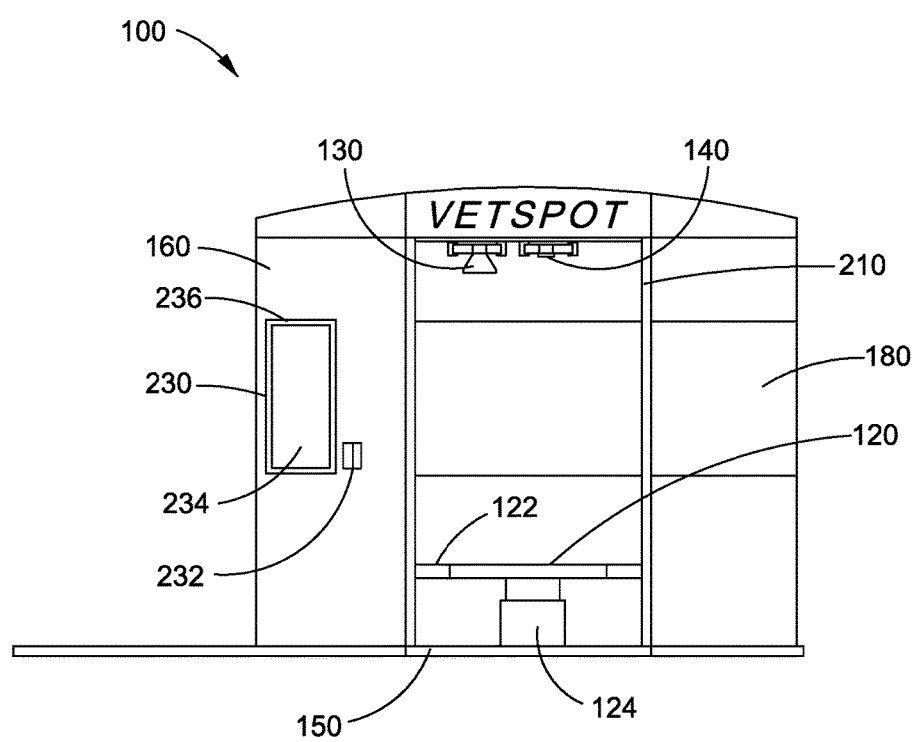
FIG. 5 is a side plan view of the veterinary kiosk of FIG. 1.
Figure 6:
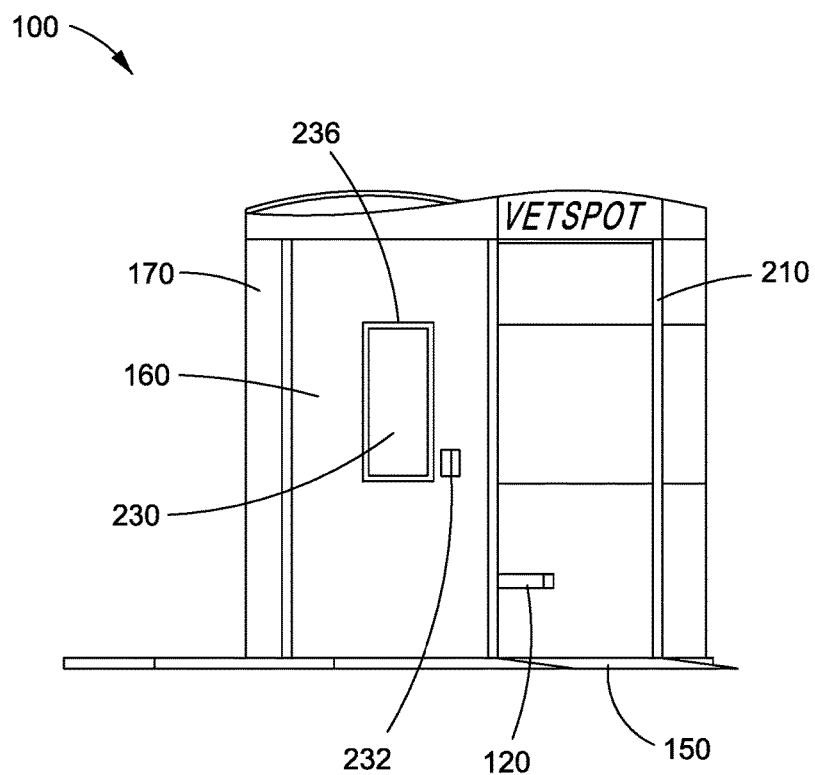
FIG. 6 front plan view of the veterinary kiosk of FIG. 1.

Referring now to FIGS. 4-6, front panel 160 includes a registration station 230. The registration station is illustrated as including a touch screen 232, a display screen 234, and an optional frame 236 upon which such components can be mounted. The shape of the frame, when used, is non-limiting. The frame, when used, can be designed to be easily removed from the front panel to enable servicing, repair, replacement, etc. of one or more components of the registration station; however, this is not required. As can be appreciated, the registration station can also or alternatively include other or optional features (e.g., additional display screen, additional touch screen, lights, buttons, switches, camera, speakers, microphone, keyboard, scanner, receiver, transmitter, credit card/debit card or other some other card reader, smart phone or other smart device reader/scanner, finger and/or eye scanner, shelf, printer, storage cavity, service access door, motion sensor, sound sensor, temperature sensor, logos, etc.). The touch screen is generally used to allow a user to enter in information about the user (e.g., age, sex, contact information, animal name, animal sex, animal breed, animal age, payment information, medical history, medical issue, etc.). The touch screen can be substituted for a keyboard; however, this not required. The frame is designed to mount the touch screen at some angle (e.g., 10-80°) relative to the front plane of the front panel 160; however, this is not required. As can be appreciated, one or more other or optional features of the registration station can also or alternatively be located on other regions of the registration station. The touch screen can display various types of information (e.g., electronic keyboard, instructions on how to register, questions that are displayed during registration, instructions during registration, information displayed to user during registration, various templates, various menus, various lists of information, etc.). As can be appreciated, the veterinary kiosk can be designed to accept voice commands during the registration process; however, this is not required. The display screen can be used to provide various types of information (e.g., registration information, information input by the user, advertising information, information about the veterinary kiosk, information about wait time for a veterinary kiosk, information as to the order of users waiting to use the veterinary kiosk, information about whether a veterinary kiosk is available or in use, cable TV, satellite TV, local broadcast TV, infomercial, medical programs, DVD materials, Blu-ray materials, video streaming, etc.). Generally, a user enters payment information at the registration station (e.g., swipes a credit or debit card, etc.); however, it can be appreciated that payment information can also or alternatively be entered inside the veterinary kiosk, at the optional attendant station, wirelessly or over a network via a smart phone or other device or by a computer connected to a network, etc. If an attendant is available, the attendant can assist a user during the registration process; however, this is not required. Generally, the veterinary kiosk includes a single registration station; however, this is not required. As can be appreciated, the registration station can alternatively be located inside the veterinary kiosk, at the attendant station, on other panels or sidewalls of the veterinary kiosk, or located remotely from the veterinary kiosk (e.g., central registration center for use with multiple veterinary kiosks, etc.).

Referring now to FIGS. 2-4 and 7, a non-limiting interior of the veterinary kiosk is illustrated. As previously discussed, the interior room or cavity of the veterinary kiosk can optionally include a scale, a bench and/or a UV sanitizing system. The interior chamber of the veterinary kiosk includes a front interior panel 300. The front interior panel 300 can be connected to front panels 160 and/or 170. The front interior panel can be pivotally connected to front panel 160 or 170 to enable the front interior panel to be moved away from the interior surface of one or both front panels; however, this is not required. The movement of the front interior panel can be used to allow access to the components (e.g. computer, router, server, battery backup, harddrive, medical devices, electronic locks, fans, displays, speakers, camera, headphone jack, electronic scale, Bluetooth™ devices, lights, pumps, scanners, touch pad, ID verification devices, printer, etc.) that are located between front panels and front interior panel 300; however, this is not required. Such access can be used to facilitate in the service, maintenance, upgrading, replacement, etc. of such components; however, this is not required. The front interior panel can include a lock; however, this is not required.

The front of the front interior panel can include a desk top that is used to support one or more touch screens, touch pads or keyboards positioned on the desk top; however, this is not required. The shape, thickness and size of the desk top are non-limiting. The desk top can be secured to or formed on the front interior panel 300; however, this is not required. The desk top can have one or more support legs; however, this is not required. The one or more touch screens, touch pads, keyboards, etc. on the desk top can be secured to the desk top; however, this is not required. The size, shape and thickness of the one or more touch screens, touch pads, keyboards, etc. are non-limiting. The one or more touch screens, touch pads, keyboards, etc. are designed to be used by a user to enter various types of information (e.g., quality survey, user history, animal medical information, payment information, questions to veterinary provider, vitals, etc.) before, during and/or after receiving veterinary services. As can be appreciated, the one or more touch screens, when used, can additionally or alternatively be used to provide information and/or instructions to the user and/or can provide other uses for the user (e.g., use policy, instructions on how to use the veterinary kiosk and/or medical devices, providing information on next step of medical visit, request assistance, increase/decrease speaker volume, increase/decrease headjack volume, focus medical devices, adjust volume of medical devices, adjust lighting in kiosk, etc.) during use of the veterinary kiosk; however, this is not required. The desk top can optionally include one or more other devices (lights, buttons, switches, camera, speakers, microphone, scanner, receiver, transmitter, credit card/debit card or other some other card reader, smart phone or other smart device reader/scanner, finger and/or eye scanner, shelf, printer, storage cavity, motion sensor, sound sensor, temperature sensor, logos, scanner, etc.); however, this is not required. A chair can be provided to enable the user to sit when using the veterinary kiosk. The chair can be a free standing chair or be connected to the veterinary kiosk.

Figure 7:
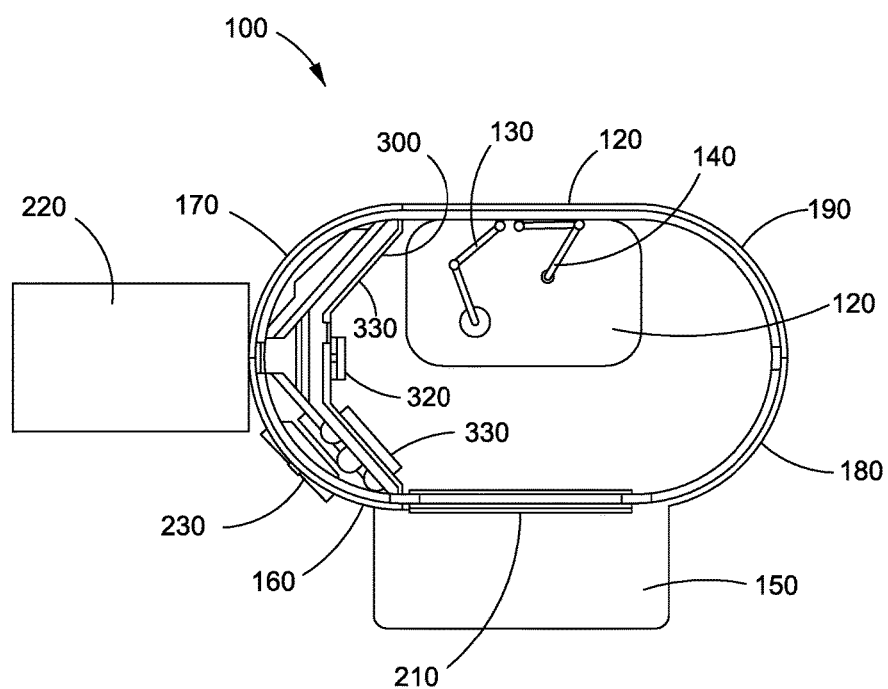
FIG. 7 is a top plan view of the veterinary kiosk of FIG. 1.

As illustrated in FIGS. 2, 3 and 7, the one or more display screens 310 are located on the front interior panel 300. An input key board 320 is illustrated as being located below the display screen 310; however, this is not required. The display screen can be a touch screen; however, this is not required. As can be appreciated, one or more monitors or display screens can be positioned on other or additional locations in the veterinary kiosk. The shape, size and thickness of the one or more monitors are non-limiting. The monitor is generally used to view the one or more veterinary providers when the user is located in the veterinary kiosk. The one or more monitors can also or alternatively display other or additional information (e.g., instructions, questions, general medical information, time, output or results of examination of user, vitals information, results from the medical devices, advertisements, information about the veterinary kiosk, information being displayed and/or entered by the user on the touchscreen, etc.).

One or more cameras (e.g., video camera, etc.) can be positioned on the interior wall panel and/or be embedded in the one or more monitors or display screens. As can be appreciated, one or more cameras can be positioned on other or additional locations in the veterinary kiosk. The one or more cameras enable pictures of the user and/or animal in the veterinary kiosk to be transmitted to a remotely located veterinary provider. The remotely located veterinary provider also typically includes a camera at his/her location so that pictures of the veterinary provider can be transmitted to the one or more monitors or display screens 310 in the veterinary kiosk. Such an arrangement can allow for real-time or near real-time video conferencing between the user and veterinary provider while the user is located in the veterinary kiosk. The one or more cameras can have other or additional functions (e.g., determine height of animal when positioned on examination scale or other locations in the veterinary kiosk, view one or more regions of the animal so as to provide a medical examination of the animal in the veterinary kiosk, monitor occupancy of the veterinary kiosk, provide security monitoring for the veterinary kiosk, etc.). The one or more monitors or display screens in the veterinary kiosk can also be used to replay one or more portions of the video conference between the user and veterinary provider after the session with the veterinary provider has ended; however, this is not required. Such a feature, when available, enables the user to review or again listen to instructions, advice, etc. provided by the veterinary provider to the user. This video playback feature, when available, can be limited to being viewed by the user while the user remains in the veterinary kiosk, or can also or alternatively be accessed by the user after the user exits the veterinary kiosk; however, this is not required. If the user can optionally access the recorded video conference outside the veterinary kiosk, the video file can 1) be accessed from some central server, 2) electronically sent to a personal computer, mobile device, tablet, laptop, etc., and/or 3) mailed to the user (e.g., DVD, Blu-ray disk, video tape, USB jump drive, etc.).

One or more speakers can be positioned on the front interior panel of the veterinary kiosk. As can be appreciated, one or more speakers can be positioned on other or additional locations in the veterinary kiosk. The speakers can be used to enable a user in the veterinary kiosk to listen to what the veterinary provider is saying to the user. One or more microphones are generally included in the veterinary kiosk to enable the user to verbally communicate with the veterinary provider. The veterinary kiosk can optionally include a braille keyboard and/or reader to enable the visually and/or hearing impaired to communicate with a veterinary provider while in the veterinary kiosk. The speakers can also or alternatively be used to play background music, sound an alarm, etc. A headphone jack can be provided on the interior front panel and/or other locations in the veterinary kiosk to enable headphones to be connected to the veterinary kiosk; however, this is not required. The interior front panel and/or other locations in the veterinary kiosk can include one or more data ports (e.g., USB™, Ethernet, Firewire™, etc.) to enable medical devices, storage devices, smart phones, computers, tablets, and/or other devices to be connected to the veterinary kiosk; however, this is not required. For example, the data port could be used by a user, to download and/or upload information to a medical device on an animal (e.g., heart monitor, heart pacemaker, implantable cardioverter defibrillators, etc.).

The front interior panel 300 can optionally include one or more air vents. The one or more air vents, when used, can enable air to enter or exit an interior location positioned between the front wall panels and the front interior panel to thereby provide circulation in the veterinary kiosk. Such interior location can include one or more fans to draw air through the one or more vent and into the interior location;

however, this is not required. The interior location can include one or more computers, routers, servers, battery backups, harddrives, medical devices, electronic locks, displays, speakers, cameras, headphone jacks, Bluetooth™ devices, lights, pumps, devices, printers, etc. Such devices can generate heat during operation, thus the air flow can optionally be used to provide cooling for such devices.

The front interior panel can include one or more equipment chambers 330 can be positioned on or near the front interior wall. The equipment chambers are used to store one or more medical devices (e.g., a stethoscope, an otoscope, a thermometer, a dermascope, a stadiometer/height gauge, a blood pressure monitor, and/or one or more grooming tools, etc.). The one or more equipment chambers can also or alternatively be used to include other types of materials (e.g., tissue, Band-Aid™, gauze, cotton ball, disinfecting wipe, cortisone cream, anti-biotic cream/ointment, cotton swab, fabric wrap, etc.). The one or more equipment chambers generally include a door 332 to limit access to the one or more equipment chambers; however, this is not required. The door, when used, can be manually openable/closeable, and/or the doors can be controllably opened/closed remotely by the veterinary provider and/or attendant. Generally, the doors are controllably opened and/or unlocked by the veterinary provider during the examination of the user in the veterinary kiosk. After the user has left the veterinary kiosk, the attendant can enter the veterinary kiosk, clean the medical equipment that was handled or used by the prior user, and/or dispose of and/or replace items that were used and/or handled by the prior user. Thereafter, the attendant can restock, replace, and/or reposition the medical equipment and/or non-medical equipment in the equipment chambers and close the equipment chamber doors prior to the next user entering the veterinary kiosk. One or more types of medical equipment can be designed to transmit information by wire or wirelessly to electronic components in the veterinary kiosk and/or to the remotely located veterinary provider. As illustrated in FIGS. 2 and 3, six equipment chambers having doors are included in the veterinary kiosk, three on each side of the monitor 310. As can be appreciated, a larger or smaller number of equipment chambers can be used. As also can be appreciated, some or all of the equipment chambers can be absent doors. For example, FIG. 2 illustrates one equipment chamber that is absent a door that is located above three equipment chambers that include doors; however, it can be appreciated that such equipment chambers can include a door and/or one or more of the six equipment chambers can be absent a door. The doors on the six equipment chambers are designed to be unlocked and/or opened remotely by the veterinary provider and/or during the taking of vitals by the user; however, this is not required. The doors are designed to automatically lock when the doors are closed by the attendant after the user has left the veterinary kiosk; however, this is not required. Each of the six equipment chambers is designed to include a different piece of medical equipment, namely a stethoscope, an otoscope, a thermometer, a dermascope, a stadiometer/height gauge, a blood pressure monitor. One or more grooming tools can be located on a chamber without a door and/or be located in another chamber with a door. As can be appreciated, a larger or smaller number of medical equipment can be used in the veterinary kiosk and/or different types of medical equipment can be included in the veterinary kiosk.

As can be appreciated, the veterinary kiosk is not required to be a closed structure. For example, the floor (when used), panels 180, 190, door 200, side wall 190, ceiling (when used), ramp 150, bench (when used) and UV sanitizer (when used) can be absent from the veterinary kiosk. As can also be appreciated, in such a configuration, only a single front panel may be used (e.g., panel 170 is absent, etc.). The attendant desk 220 may also be absent. In this non-limiting arrangement, the veterinary kiosk 100 can be placed in a private room and/or some other location. In this alternative confirmation, the veterinary kiosk can include a registration station that can be the same or similar as the registration station described above. The veterinary kiosk can include front wall panels 160 and 170 or a single wall front wall panel 160. The front wall panel(s) can have the same shape as described above, be flat, or have some other shape. In this alternative confirmation, the veterinary kiosk can include an interior front panel 300 which can be the same or similar to interior front panel 300 as described above. The interior front panel can be pivotally connected to the one or more front wall panels; however, this is not required. The interior front panel may or may not include a monitor or Physician Screen 310. If the interior front panel is the same or similar to interior front panel 300 as described above, then the user can have a teleconference with a veterinary provider. However, if interior front panel does include a monitor or Physician Screen 310 and one or more other components (e.g., speakers, headphone jack, etc.), then the user may only be able to collect one or more vitals and then proceed to another location to visit a veterinary provider. As can also be appreciated, the veterinary kiosk can also be absent the desk top, medical device compartments, medical device retraction system, some or all medical devices, User Screen and the like such that the veterinary kiosk primarily includes the registration station 230 to enable a user to check-in for a visit with a veterinary provider. As can be appreciated, one or more features of the veterinary kiosk of the present invention can be used in other ways to provide veterinary services to a user.

The veterinary kiosk and method for using the veterinary kiosk are a novel and advanced in a veterinary care delivery system wherein users and veterinary providers can engage in real-time interactive consultations, providing convenient and affordable veterinary services. The veterinary kiosk includes the latest technologies in medical devices, video conferencing, and VOIP telephony so that the veterinary kiosk can extend traditional veterinary care to convenient retail locations, pet store locations or other locations in a user's neighborhood, therein enabling a user to see a veterinary provider and obtain veterinary services and a prescription, if required, in a fast and convenient manner.

Some advantageous aspect of the veterinary kiosk and medical method are:
    User portal (cloud-based),
    Provider portal (cloud-based),
    Integrated care station,
    Facilitates efficient delivery of basic veterinary care delivery,
    Automates all aspects of a check-up,
    Easy check-in,
    Vital signs capture of animal,
    Prescription generation,
    Post-care and outcomes,
    Convenient locations where consumers want to be, and
    Video playback of the recorded session between the user and veterinary provider.

The veterinary kiosk and medical method can be used to provide veterinary services in four (4) simple steps:
    Step 1—User begins/completes check-in process via web portal or at the veterinary kiosk. The user can optionally begin the check-in via web portal and then later complete check-in process at the veterinary kiosk; however, this is not required. A veterinary provider can send a reminder to user regarding an appointment and/or begin the check-in process for a user (e.g., follow-up appointment, etc.); however, this is not required.

Step 2—Veterinary provider receives eligible request and accepts and/or is assigned to user.

Step 3—User visits the veterinary kiosk and has a private appointment with a veterinary provider via the User Screen.

Step 4—Visit is completed. The veterinary kiosk and/or veterinary provider can then provide additional care/services that include: prescription, billing information, education, referrals, and/or follow up. The veterinary provider can cause the veterinary kiosk to printout a prescription and/or directly send the prescription request to a pharmacy, pet store, etc. The veterinary kiosk can print out a bill after the veterinary services are provided and/or accept payment prior to or after veterinary services are provided. The veterinary kiosk can be designed to accept and/or process medical insurance information provided by the user. The veterinary kiosk can print out and/or display education materials/information relevant to/requested by the user and/or provided by the veterinary provider. The veterinary kiosk and/or veterinary provider and/or attendant can schedule a follow-up visit for the animal of the user. Email, twitter, Facebook, test, and/or mail reminders can be sent to the user regarding scheduled and/or follow-up visits. The veterinary provider and/or attendant can schedule a visit with another veterinary provider and/or admit the animal to an animal hospital, animal clinic, etc. during or after the visit to the veterinary kiosk. A visit summary can be printed out and/or sent to the user. As can be appreciated, the veterinary kiosk and method for using the veterinary kiosk can have other or additional features.

Advantageous portal features of the veterinary kiosk and associated medical method are:
  Practice management engine.
    Appointments scheduling engine.
    Online eligibility, claims, and billing engine.
    ePrescribing with alerts and reminder engine.
    Medical records interface and cccess.
      Animal Health Record (PHR).
      Electronic Animal Health record (EMR).
      Rules-Based Care Plans.
      Rules-Based Education.
  Check-in pathway to care engine.
  Secure video conferencing engine.
  Documentation module.
    Appointment storage and analysis.
  Education and post-care.

Some non-limiting advantages to users by use of the veterinary kiosk and medical method are:
  Convenient.
    Closer to home.
    Saves time.
    Language and culture friendly.
  Better Access.
    Personal veterinary provider available while traveling.
    Larger selection of veterinary provider.
    Not limited by veterinary provider's visitation schedule.
  More Accurate.
    Review record of appointment.
    Automatic data entry into PHR.

Some non-limiting advantages to veterinary providers by use of the veterinary kiosk and medical method are:
  Higher Revenues.
    More appointments/day.
    Less traveling.
  More Accurate.
    Review record of appointment.
    Automatic data entry into EMR/HER.
  Integrated Care.
    Referral and transfer.
  Load Balancing.
    Appointment load can be shared with other veterinary providers regardless of location.

Some non-limiting advantages to payers by use of the veterinary kiosk and medical method are:
  Change in Status.
    Transition from Payer to Provider.
  Market Leverage.
    New Business Model.
  Efficiency.
    Market Demand.
    Less Overhead.
    Scalability.
    Less Liability.

The method for providing veterinary services via a veterinary kiosk regarding protocols for scheduling, diagnosing, delivering and documenting telemedicine veterinary care can include:

a. Veterinary Provider Application—this application is used by the veterinary provider to provide veterinary services. The application contains all that the veterinary provider requires to diagnose, deliver care and document the veterinary episode. It runs on the veterinary provider's computer and can be integrated with the leading veterinary applications.

b. User Application—this application is used by the user to register with a veterinary kiosk and also captures the animal's medical history and/or vitals. It includes all the information required to administer veterinary services to the animal of the user. This includes financial/billing information and an Electronic Medical Record (EMR), which can be accessed by the user and the veterinary providers.

c. Integrated videoconferencing software—this application supports the live user-clinician interaction required for delivery of the veterinary services. It uses a secure connection to the servers and the provider via an internet connection.

To use a veterinary kiosk, the users/users may go through one or more of the following steps:

a. Go online, register and schedule an appointment at the nearest terminal or walk-in and register at the veterinary kiosk.

b. Use the scheduling engine to select an appointment time.

c. Input insurance, preferred pharmacy location and/or billing information, and remit payment.

d. Complete pre-appointment pathway to care.

e. Visit a veterinary kiosk and see a veterinary provider via the integrated care terminal.

f. Pick up prescription, if indicated, at the pharmacy, pet store, etc. of choice.

g. Optionally use website to manage animal's care until animal is better.

Some of the non-limiting features of the veterinary kiosk are:
  Integrated Medical Devices.
  Exterior Check-In Station.
  User Waiting Area.
  Integrated Wi-Fi™ Hot Spot.

Touch Screen User Interface.
Instant Sterilization.
Video/Audio Conferencing.
Flexible Access.
Modular design.
Small Footprint.
Fully Integrated Interior Design.
Secure PC storage with access.
Open design feels comfortable.
Payment and Signature.
Integrated Medical Devices.
Exterior Check-In Station—A monitor and keyboard is generally mounted on the outside of the veterinary kiosk to allow for new user registration and check in. The station can be designed to take payment and/or a fingerprint. The station generally is located away from the entrance to the veterinary kiosk to allow a degree of separation from the user inside the veterinary kiosk. The attendant can use this station for her work.
User Waiting Area—Can include a small area to put a few chairs outside the veterinary kiosk to act as a waiting area.
Integrated Wi-Fi™ Hot Spot—In order to minimize network connection cost, a Wi-Fi™ hot spot can partner with an ISP of choice (AT&T™, Verizon™, Sprint™, T-Mobile™, etc.).
Touch Screen User Interface—The user can be allowed to interact while inside the veterinary kiosk by use of a touch screen interface.
Security Compliant Design—The veterinary kiosk will generally be sound proof and a passerby cannot see in and see any user information. The veterinary kiosk generally is fully enclosed and lockable, but can allow exterior access in case of emergency.
Instant Sterilization—Because of the many germs and other contaminants that will be inside the veterinary kiosk, a sterilization technology can be used in the veterinary kiosk. One type of sterilization system that can be used is a built-in sanitizing misting system that dispenses from a series of misters between every appointment. Another or additional sterilization system that can be used is a UV lighting system that can be blasted between appointments. Other techniques and technologies can also or alternatively be used. The attendant can have the ability to activate one or more sterilization systems (e.g., via button, computer, etc.). The attendant can be required to keep track of records about the sanitization process and can ensure that the doors to the veterinary kiosk are closed/locked during the sterilization process.
Video/Audio Conferencing—The user will communicate with the veterinary provider via video and audio conferencing technology. This environment can make the user feel as close to the veterinary provider as actually being present as possible. A two-way glass can be used to place the camera in the center of the monitor to keep the user looking head on, versus the Skype and current video conferencing solutions that keep users looking at the camera and back to the monitor.
Flexible Access—The veterinary kiosk should have a large enough door to accommodate a wheel chair.
Modular design for standard door deployment—The veterinary kiosk can be built in a manner that allows it to enter through the door and quickly be assembled.
Small Footprint—Because of the cost of retail space, the veterinary kiosk will be small enough to fit in most locations (e.g., 4-6 ft. wide and 7-10 ft. length).
Fully Integrated Interior Design—The interior of the veterinary kiosk can be designed to be cleaner, sleeker, nicer, more luxurious, than the experience they get at the average veterinary's office.
Expandable Device Rail—The veterinary kiosk can include the latest medical devices and update such medical devices in a more rapid manner than the average veterinary office. The veterinary kiosk can include a mounting rail type system that allows medical devices in the veterinary kiosk to be easily accessed by the user. An indicator, such as a light, can be used to notify which medical device is to be used by the user.
Secure PC storage with access—Because uptime of the software is so important, electronics can be inserted in a compartment in the veterinary kiosk. Such area generally should be secure, cooled, and easily accessible for service.
Open design feels spacious—The veterinary kiosk is generally designed to feel bigger than it is such as by providing a glass window that wraps around the back half of the kiosk.
Payment and Signature—The veterinary kiosk can include an integrated credit card swipe for payment, and a signature pad for medical authorization.
Finger Print Reader—A finger print reader can be included on the veterinary kiosk to confirm user ID under HIPAA.
Integrated Printer—An integrated printer can be included in the veterinary kiosk to print medical and insurance forms and/or receipts and/or prescription. The printer can also print coupons based upon diagnosis to promote product sales. Our software can be included to inform the attendant of low paper in the paper.
Video Playback—The recorded medical session can be partially or fully reviewed by the user to enable the user to again listen to information, instructions and/or advise from the veterinary provider. As can be appreciated, the video playback feature can also or alternatively be used for auditing purposes, compliance purposes, security purposes, quality control purposes, etc.

FIG. 1 illustrates a diagram illustrating one non-limiting arrangement in accordance with the present invention to remote provide veterinary services via a veterinary kiosk. The communication between the one or more remotely located veterinary providers and the one or more veterinary kiosk is illustrated as being established via the cloud, internet, and/or a network. The cloud, internet, and/or a network can be used for data accumulation, interpretation and routing applications, scheduling applications, device control applications, digital signage and marketing management applications, telecommunication application, etc. The veterinary provider can communicate with one or more veterinary kiosks in one or more ways (e.g., smart phone, computer, laptop computer, tablet, etc.). The device used by the veterinary provider can include provider application software, data entry and device control software, examination software, etc. One or more databases can be in communication with the cloud, internet, and/or a network. The one or more databases can be used to maintain information about an animal and/or user, maintain information about the veterinary visit, maintain information about the examination, maintain information about payment information, maintain information about insurance information, maintain information about system records, etc. The veterinary kiosk can include one or more computers, routers, hard drives, etc. to provide examination applications, telecommunication applications, registration applications, payment applications, etc. Also, the veterinary kiosk can include telecommunication equipment, PCs, electronic devices, power system devices, controls, data entry and payment devices, examination equipment, etc.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A veterinary kiosk configured to provide tele-med services for an animal accompanied by a user, said veterinary kiosk including a modular kiosk structure defined by one or more of a floor panel, a front panel, a rear panel and a sidewall, wherein each of said floor panel, front panel, rear panel, and sidewall may be assembled with or disassembled from other such panels and each, when disassembled, is configured to fit through a standard doorway opening, a user display conferencing system, an animal examination table, an animal scale, and one or more medical devices, said user display conferencing system configured to enable the user to have a real-time or near real-time teleconference with a veterinary provider located remotely from said veterinary kiosk, said user video conferencing system including a first video screen and second video screen, a video conference camera, a microphone, a computer system and videoconferencing software, said first display screen configured to display said veterinary provider during said tele-conference between said user and said veterinary provider, said second display screen configured for said user to view information other than information displayed on said first display screen, said first and second display screens positioned on said kiosk structure such that said user can simultaneously view said first and second display screens, said computer system and videoconferencing software including electronic hardware and software to form a video connection between said veterinary kiosk and the remotely-located veterinary provider so that the remotely-located veterinary provider is displayed in real-time or near real-time on said first display screen, said kiosk structure defining at least one medical compartment housing one or more medical devices, said medical compartment including an automatic or remote controlled door which can be opened or closed by the remote veterinary provider; and wherein the kiosk further includes a mobile device application, a network application or combinations thereof, said mobile device application, said network application or combinations thereof configured to allow the user various functions on a mobile device, a personal computer, or combinations thereof, said functions including at least a scheduling function; and further comprising including a medication adherence software application that provides the following functions 1) enabling the user to speak to a pharmacist or veterinary provider, 2) enabling the user to change the animal's medication alerts, 3) enabling the user to learn about certain types of animal medical conditions, 4) enabling the user to check medication order status, 5) enabling the user to check medication delivery status, 6) enabling the user to refill a prescription, 7) enabling the user to transfer prescriptions to another location, 8) enabling the user to obtain information about recommended animal medication dosages, 9) enabling the user to obtain information about recommended times for animals to take medications, 10) enabling the user to obtain information about recommended frequency for animals to take medications, 11) enabling the user to obtain information about medications, 12) enabling the user to obtain information about generic brands available for medications, 13) enabling the user to request an appointment to speak with the veterinary provider, 14) enabling the user to enter information regarding compliance information regarding medication usage by the animal, 15) enabling the user to receive compliance reports for animals regarding medication usage, 16) enabling the user to pay for the prescription, 17) enabling the user to select between a generic and non-generic brand of medication, 18) enabling the user to compare pricing and/or delivery options for various medications, 19) providing reminders for the user to give medications to the animal, 20) monitoring and/or generating progress reports to the user regarding adherence to medication usage for the animal, and 21) enrolling the user in an electronic prescription network which sends prescriptions to the user's choice of pharmacy.

2. The veterinary kiosk as defined in claim 1, including an exterior registration station, said exterior registration station including a user input system configured to enable the user to enter information about the user and animal prior to having said real-time or near real-time tele-conference with a veterinary provider, said user input system includes one or more components selected from the group consisting of a keypad for identification and/or data entry, keyboard for identification and/or data entry, a touch screen for identification and/or data entry, an input system microphone and/or voice recognition software for identification and/or data entry, a fingerprint scanner for identification and/or data entry, a retina scanner for identification and/or entry, an input system camera, an input system speaker, an input system scanner, an input system card reader, an input system printer, a motion sensor, a sound sensor, and a temperature sensor, said exterior registration station is configured for use by the user to perform one or more functions selected from the group consisting of a) enabling the user to enter the name of the user, b) enabling the user to enter the address of the user, c) enabling the user to enter contact information of the user, d) enabling the user to enter the age of the user, e) enabling the user to enter the sex of the user, f) enabling the user to enter animal's name, g) enabling the user to enter breed of animal, h) enabling the user to enter animal's sex, i) enabling the user to enter animal's height, j) enabling the user to enter animal's age, k) enabling the user to enter animal's weight, l) enabling the user to enter the speaking language of the user, m) enabling the user to enter animal's medical history, n) enabling the user to enter current and/or past medicines used by animal, o) enabling the user to enter information on past medical conditions of animal, p) enabling the user to enter reason(s) for visit, q) enabling the user to enter animal's current symptoms, r) enabling the user to enter animal's allergies, s) enabling the user to enter ID number and/or password information, t) enabling the user to enter insurance information, u) enabling the user to enter payment information, v) enabling the user to enter consent forms, w) enabling the user to request assistance from a veterinary attendant, x) enabling the user to enter date and/or time user desires appointment, y) enabling the user to enter information about the current veterinary provider of the user, z) enabling the user to request a specific veterinary provider and/or veterinary provider specialty, aa) providing information to the user about the veterinary kiosk, bb) providing information to the user on how to use the veterinary kiosk, cc) providing information to the user on how to properly input/convey information to the veterinary kiosk, dd) providing information to the user on the wait time for the veterinary kiosk, ee) providing a list of users and/or number of users waiting to use the veterinary kiosk to the user, and ff) providing information to the user regarding whether the veterinary kiosk is available for use.

3. The veterinary kiosk as defined in claim 2, including an exterior registration station, said exterior registration station including a user input system configured to enable the user to enter information about the user and animal prior to having said real-time or near real-time teleconference with a veterinary provider, said user input system includes one or more components selected from the group consisting of a keypad for identification and/or data entry, keyboard for identification and/or data entry, a touch screen for identification and/or data entry, an input system microphone and/or voice recognition software for identification and/or data entry, a fingerprint scanner for identification and/or data entry, a retina scanner for identification and/or entry, an input system camera, an input system speaker, an input system scanner, an input system card reader, an input system printer, a motion sensor, a sound sensor, and a temperature sensor, said exterior registration station is configured for use by the user to perform one or more functions selected from the group consisting of a) enabling the user to enter the name of the user, b) enabling the user to enter the address of the user, c) enabling the user to enter contact information of the user, d) enabling the user to enter the age of the user, e) enabling the user to enter the sex of the user, f) enabling the user to enter animal's name, g) enabling the user to enter breed of animal, h) enabling the user to enter animal's sex, i) enabling the user to enter animal's height, j) enabling the user to enter animal's age, k) enabling the user to enter animal's weight, l) enabling the user to enter the speaking language of the user, m) enabling the user to enter animal's medical history, n) enabling the user to enter current and/or past medicines used by animal, o) enabling the user to enter information on past medical conditions of animal, p) enabling the user to enter reason(s) for visit, q) enabling the user to enter animal's current symptoms, r) enabling the user to enter animal's allergies, s) enabling the user to enter ID number and/or password information, t) enabling the user to enter insurance information, u) enabling the user to enter payment information, v) enabling the user to enter consent forms, w) enabling the user to request assistance from a veterinary attendant, x) enabling the user to enter date and/or time user desires appointment, y) enabling the user to enter information about the current veterinary provider of the user, z) enabling the user to request a specific veterinary provider and/or veterinary provider specialty, aa) providing information to the user about the veterinary kiosk, bb) providing information to the user on how to use the veterinary kiosk, cc) providing information to the user on how to properly input/convey information to the veterinary kiosk, dd) providing information to the user on the wait time for the veterinary kiosk, ee) providing a list of users and/or number of users waiting to use the veterinary kiosk to the user, and ff) providing information to the user regarding whether the veterinary kiosk is available for use.

4. The veterinary kiosk as defined in claim 3, wherein said kiosk structure includes an interior chamber and a cleaning or sanitizing system to clean or sanitize at least a portion of said interior chamber, said cleaning or sanitizing system including one or more systems selected from the group consisting of a UV system and a mist system, said interior chamber including said first and second video screens, said animal examination table, and said animal scale.

5. The veterinary kiosk as defined in claim 1, wherein said kiosk structure includes an interior chamber and a cleaning or sanitizing system to clean or sanitize at least a portion of said interior chamber, said cleaning or sanitizing system including one or more systems selected from the group consisting of a UV system and a mist system, said interior chamber including said first and second video screens, said animal examination table, and said animal scale.

6. The veterinary kiosk as defined in claim 1, including an exterior display screen that can be used to provide one or more types of information selected from the group consisting of advertising information, information about the veterinary kiosk, information about the wait time for a veterinary kiosk, information as to the order of users waiting to use the veterinary kiosk, information about whether the veterinary kiosk is available, cable TV shows, satellite TV shows, local broadcast TV shows, infomercials, medical programs, video materials, video programs, internet programs, and pictures, said exterior display screen positioned on said kiosk structure such that a user is unable to simultaneously view said exterior display screen and said first video screen.

7. The veterinary kiosk as defined in claim 1, wherein said kiosk structure includes an interior chamber, a front interior panel of said interior chamber is a moveable panel that allows access to one or more interior components located behind said moveable panel, said movable panel includes a lock to prevent unauthorized opening of said moveable panel, said movable panel includes a caster, a roller, and/or a rail system to facilitate in the opening and closing of said movable panel, a front face of said movable panel includes said first and second video screens, said one or more interior components including components selected from the group consisting of computer and/or other electronics used for network communication and/or storage.

8. The veterinary kiosk as defined in claim 1, including a prescription drug system that includes one or more functions selected from the group consisting of 1) enabling a veterinary provider to generate electronic prescriptions, 2) enabling the user to select and/or order prescription drugs, 3) enabling the user to choose between name brand and generic drugs, 4) enabling the user to choose the supply quantity for the prescription, 5) enabling the user to choose between picking up the prescription at a location of their choice or mail delivery of the prescription, 6) enabling the user to enter medical insurance information for partial or full payment of the prescription, 7) enabling the user to enter credit or debit card information to pay for the prescription, 8) enabling the user to enter information for mail delivery of the prescription, 9) enabling the user to enter information to provide automatic reminders to the user regarding refilled and/or follow-up medical visits, 10) enabling the user to enter information such that the user is notified when prescription has been mailed and/or is ready to be picked-up at the pharmacy, 11) enabling the user to obtain a print out and/or electronic version of the prescription written by the veterinary provider, 12) enabling the user to receive information about the issued prescription in printout and/or electronic form, and 13) enabling the user to select the location to pick up the prescription.

9. The veterinary kiosk as defined in claim 1, including a mobile device application, a network application or combinations thereof, said mobile device application, said network application or combinations thereof configured to allow the user various functions on a mobile device, a personal computer, or combinations thereof, said functions including one or more functions selected from the group consisting of 1) locating an available veterinary kiosk, 2) scheduling an appointment with the veterinary kiosk, 3) pre-registering symptoms and/or reasons for visit, 4) setting and/or canceling an appointment with the veterinary kiosk, 5) receiving reminders and/or updates regarding appointments for the veterinary kiosk, 6) obtaining information about availability of said veterinary kiosk, 7) obtaining information about certain veterinary provider availability, 8) obtaining information about the available veterinary provider, 9) enabling the selection of a certain veterinary provider and/or veterinary provider in a certain field of medicine, 10) obtaining map information, address information and/or hours of operation information regarding a selected veterinary kiosk, 11) locating the closest veterinary kiosk and/or the veterinary kiosk availability for a certain veterinary provider and/or veterinary provider in a certain field of medicine, 12) presubmitting and/or preclearing medical insurance, 13) submitting payment information, 14) receiving information on payment status, 15) receiving information on insurance coverage, 16) receiving appointment reminders and/or updates, 17) receiving prescription information, 18) answer surveys regarding the use of the veterinary kiosk, 19) entering personal information about user, 20) entering information about the animal, and 21) receiving medication reminders.

* * * * *